(12) United States Patent
Brown et al.

(10) Patent No.: US 8,440,785 B2
(45) Date of Patent: May 14, 2013

(54) COMPOSITIONS, METHODS AND POLYMERS

(75) Inventors: Christopher T. Brown, Pittsburgh, PA (US); Chad Landis, Oakmont, PA (US); Elena E. Sheina, Pittsburgh, PA (US)

(73) Assignee: Plextronics, Inc., Pittsburgh, PA (US)

( * ) Notice: Subject to any disclaimer, the term of this patent is extended or adjusted under 35 U.S.C. 154(b) by 0 days.

(21) Appl. No.: 12/828,121

(22) Filed: Jun. 30, 2010

(65) Prior Publication Data

US 2011/0028644 A1 Feb. 3, 2011

Related U.S. Application Data

(60) Provisional application No. 61/222,053, filed on Jun. 30, 2009, provisional application No. 61/240,137, filed on Sep. 4, 2009, provisional application No. 61/241,813, filed on Sep. 11, 2009, provisional application No. 61/248,335, filed on Oct. 2, 2009, provisional application No. 61/289,314, filed on Dec. 22, 2009, provisional application No. 61/290,844, filed on Dec. 29, 2009, provisional application No. 61/307,387, filed on Feb. 23, 2010.

(51) Int. Cl.
*C08G 75/00* (2006.01)

(52) U.S. Cl.
USPC ............................ 528/377; 528/380; 528/370

(58) Field of Classification Search .................. 528/377, 528/373, 380
See application file for complete search history.

(56) References Cited

U.S. PATENT DOCUMENTS

| | | | |
|---|---|---|---|
| 4,356,429 A | 10/1982 | Tang | |
| 4,539,507 A | 9/1985 | Van Slyke et al. | |
| 4,585,878 A | 4/1986 | Jost et al. | |
| 4,778,899 A | 10/1988 | Pfenninger et al. | |

(Continued)

FOREIGN PATENT DOCUMENTS

| DE | 3435947 A1 | 4/1986 |
|---|---|---|
| EP | 0094911 B1 | 9/1986 |

(Continued)

OTHER PUBLICATIONS

Partial International Search Report in corresponding PCT Application PCT/US2010/040664.

(Continued)

*Primary Examiner* — Shane Fang
(74) *Attorney, Agent, or Firm* — Foley & Lardner LLP

(57) ABSTRACT

A composition comprising a homopolymer or a copolymer comprising bithiophene units for use in, for example, low band gap materials including uses in organic photovoltaic active layers. The band gap and other properties can be engineered by polymerization methods including selection of monomer structure and ratio of monomer components. In addition, a dimer adapted for making alternating copolymers further comprising one first monomer moiety comprising at least one bithiophene moiety compound covalently linked to one second monomer moiety comprising a different bithiophene moiety or at least one moiety that is not a bithiophene. The composition can be copolymerized to form an alternating copolymer that can be further processed to form a polymeric film used in a printed organic electronic device. A series of novel copolymers are designed that would allow fabrication of materials with tailor made electronic and/or mechanical properties that can be easily manipulated through molecules chemical structure and potentially result in long term stability under ambient conditions that can be advantageous for use in organic electronics (e.g., OPVs, OLEDs, OFETs). Improved methods are disclosed for making monomers comprising a benzo[2,1-b:3,4-b']dithiophene moiety that are useful as electronics materials.

52 Claims, 15 Drawing Sheets

U.S. PATENT DOCUMENTS

| | | | |
|---|---|---|---|
| 4,921,566 A | 5/1990 | Stork | |
| 4,931,566 A | 6/1990 | Surber et al. | |
| 5,247,190 A | 9/1993 | Friend et al. | |
| 5,401,827 A | 3/1995 | Holmes et al. | |
| 5,723,873 A | 3/1998 | Yang | |
| 6,166,172 A | 12/2000 | McCullough et al. | |
| 6,369,089 B1 | 4/2002 | Burk et al. | |
| 6,566,153 B1 | 5/2003 | Yang | |
| 6,576,975 B2 | 6/2003 | Yang | |
| 6,602,974 B1 | 8/2003 | McCullough et al. | |
| 6,784,017 B2 | 8/2004 | Yang | |
| 7,166,010 B2 | 1/2007 | Lamansky et al. | |
| 7,368,624 B2 | 5/2008 | Brown et al. | |
| 7,554,111 B2 | 6/2009 | Yang | |
| 7,569,159 B2 | 8/2009 | Hammond et al. | |
| 7,796,320 B2 | 9/2010 | Yang | |
| 7,807,925 B2 | 10/2010 | Zarembo | |
| 2008/0121281 A1 | 5/2008 | Gaudiana et al. | |
| 2008/0248313 A1 | 10/2008 | Seshadri et al. | |
| 2008/0299293 A1 | 12/2008 | Sheina et al. | |
| 2008/0315187 A1 | 12/2008 | Bazan et al. | |
| 2008/0315751 A1 | 12/2008 | Sheina et al. | |
| 2008/0319207 A1 | 12/2008 | Laird et al. | |
| 2009/0065770 A1 | 3/2009 | Miura et al. | |
| 2009/0108255 A1 | 4/2009 | Bazan et al. | |
| 2009/0176994 A1 | 7/2009 | Laird et al. | |
| 2009/0221740 A1 | 9/2009 | Sheina | |
| 2009/0229667 A1 | 9/2009 | Shrotriya et al. | |
| 2009/0256117 A1 | 10/2009 | Seshadri et al. | |
| 2010/0018581 A1 | 1/2010 | Shrotriya et al. | |
| 2010/0043876 A1 | 2/2010 | Tuttle et al. | |

FOREIGN PATENT DOCUMENTS

| | | |
|---|---|---|
| EP | 0133156 B1 | 7/1991 |
| EP | 0181290 B1 | 9/1991 |
| EP | 0302018 B1 | 11/1993 |
| EP | 0672729 B1 | 9/1999 |
| EP | 0962499 A2 | 12/1999 |
| EP | 0962499 B2 | 3/2008 |
| EP | 2006291 A1 | 12/2008 |
| JP | 2007238563 A | 9/2007 |
| WO | WO99/21233 A1 | 4/1999 |
| WO | WO2003/037844 A1 | 5/2003 |
| WO | WO2007/011739 A2 | 1/2007 |
| WO | WO2007/105638 A1 | 9/2007 |
| WO | WO2008/000664 A1 | 1/2008 |
| WO | WO2008/018931 A2 | 2/2008 |
| WO | WO2008/032631 A1 | 3/2008 |
| WO | WO 2009/115413 A2 | 9/2009 |
| WO | WO2010/000669 A1 | 1/2010 |
| WO | WO2010/108873 A1 | 9/2010 |

OTHER PUBLICATIONS

Xiao, S. et al., "Conjugated Polymers Based on Benzo[2,1-b:3,4-b?]dithiophene with Low-Lying Highest Occupied Molecular Orbital Energy Levels for Organic Photovoltaics," 1 ACS App. Mat. Interfaces 1613 (2009).
U.S. Appl. No. 61/108,851, filed Oct. 27, 2008, Seshadri et al.
U.S. Appl. No. 61/115,877, filed Nov. 18, 2008, Seshadri et al.
U.S. Appl. No. 61/116,963, Nov. 21, 2008, Benson-Smith et al.
U.S. Appl. No. 12/874,163, filed Sep. 1, 2010, Sheina et al.
U.S. Appl. No. 12/874,137, filed Sep. 1, 2010, Brown et al.
Avcibasi, N. et al., "Synthesis and in vitro evaluation of dioxopyrrolopyrroles as potential low-affinity fluorescent Ca2+ indicators," 6 Int. J. Photoenergy 159 (2004).
Bao, Z. et al., "Exploration of the Stille Coupling Reaction for the Synthesis of Functional Polymers," 117 J. Am. Chem. Soc. 12426 (1995).
Billmeyer Jr., F., Textbook of Polymer Science,3rd Ed., ch. 5, John Wiley & Sons, Inc. (1984).
Blouin, N. et al., "Toward a Rational Design of Poly(2,7-Carbazole) Derivatives for Solar Cells," 130 J. Am. Chem. Soc. 732 (2008).
Bolognesi, A. et al., "Synthesis and properties of polydithienobenzene," 28 Synth. Met. 521 (1989).
Boymond, L. et al., "Preparation of Highly Functionalized Grignard Reagents by an Iodine—Magnesium Exchange Reaction," 37 Angew Chem. Int. Ed. 1701 (1998).
Bundgaard, E. et al., "Large-area photovoltaics based on low band gap copolymers of thiophene and benzothiadiazole or benzobis(thiadiazole)," 91 Solar Energy Materials and Solar Cells 1019 (2007).
Bundgaard, E. et al., "Low Band Gap Polymers for Organic Photovoltaics," 91 Solar Energy Materials and Solar Cells 954 (2007).
Burgi, L. et al., "High-Mobility Ambipolar Near-Infrared Light-Emitting Polymer Field-Effect Transistors," 20 Adv. Mater. 2217 (2008).
Chen, L. et al., "Recent Progress in Polymer Solar Cells: Manipulation of Polymer:Fullerene Morphology and the Formation of Efficient Inverted Polymer Solar Cells," 21 Adv. Mater. 1434 (2009).
Chen, T. et al., "2D Assembly of Metallacycles on HOPG by Shape-Persistent Macrocycle Templates," 132 J. Am. Chem. Soc. 1328 (2010).
Cho, S. et al., "Bulk heterojunction bipolar field-effect transistors processed with alkane dithiol," 9 Organic Electronics 1107 (2008).
Coates, N. et al., "1,8-octanedithiol as a processing additive for bulk heterojunction materials: Enhanced photoconductive response," 93 App. Phys. Lett. 072105 (2008).
Crouch, D. et al., "Thiophene and Selenophene Copolymers Incorporating Fluorinated Phenylene Units in the Main Chain: Synthesis, Characterization, and Application in Organic Field-Effect Transistors," 17 Chem. Mater. 6567 (2005).
Elias, H., An Introduction to Polymer Science, ch. 2, VCH (1997).
Facchetti, A. et al., "n-Type Building Blocks for Organic Electronics: A Homologous Family of Fluorocarbon-Substituted Thiophene Oligomers with High Carrier Mobility," 15 Adv. Mater. 33 (2003).
Farina, V. et al., "Large rate accelerations in the stille reaction with tri-2-furylphosphine and triphenylarsine as palladium ligands," 113 J. Am. Chem. Soc. 9585 (1991).
Gamota, D., ed., et al., Printed Organic and Molecular Electronics (2004).
Gladysz, J., ed., et al., Handbook of Fluorous Chemistry, Wiley (2004).
Gronowitz, S. et al., "Benzodithiophenes. A General Method of Synthesis," 12 Chem. Scripta 57 (1977).
Hirsch, A. et al., Fullerenes Chemistry and Reactions, Wiley-VCH Verlag, Weinheim (2005).
Hoppe, H. et al., "Polymer Solar Cells," 214 Adv. Polymer Sci. 1 (2008).
Hou, J. et al., "Bandgap and Molecular Energy Level Control of Conjugated Polymer Photovoltaic Materials Based on Benzo[1,2-b:4,5-b']dithiophene," 41 Macromol. 6012 (2008).
Huo, L. et al., "Bandgap and Molecular Level Control of the Low-Bandgap Polymers Based on 3,6-Dithiophen-2-yl-2,5-dihydropyrrolo[3,4-c]pyrrole-1,4-dione toward Highly Efficient Polymer Solar Cells," 42 Macromol. 6564 (2009).
Hwang, I. et al., "Carrier generation and transport in bulk heterojunction films processed with 1,8-octanedithiol as a processing additive," 104 J. Appl. Phys. 033706 (2008).
Iovu, M. et al., "Experimental Evidence for the Quasi-"Living" Nature of the Grignard Metathesis Method," 38 Macromolecules 8649 (2005).
Kang, B. et al., "Fluoropolymer indium-tin-oxide buffer layers for improved power conversion in organic photovoltaics," 93 Appl. Phys. Lett. 133302 (2008).
Koeckelberghs, G. et al., "Influence of the Substituent and Polymerization Methodology on the Properties of Chiral Poly(dithieno[3,2-b:2',3'-d]pyrrole)s," 40 Macromol. 4173 (2007).
Kraft, A. et al., "Electroluminescent Conjugated Polymers—Seeing Polymers in a New Light," 37 Angew. Chem. Int. Ed. 402 (1998).
Kroschwitz, J., ed., Concise Encyclopedia of Polymer Science and Engineering, "Copolymerization" and "Alternating Copolymers," Wiley (1990).
Kuwano, R. et al., "Aqueous Hydroxide as a Base for Palladium-Catalyzed Amination of Aryl Chlorides and Bromides," 67 J. Org. Chem. 6479 (2002).

Lee, J. et al., "Processing Additives for Improved Efficiency from Bulk Heterojunction Solar Cells," 130 *J. Am. Chem. Soc.* 3619 (2008).

Li, Z., ed., et al., *Organic Light-Emitting Materials and Devices*, CRC Press, Taylor and Francis Group, LLC, Boca Raton (2007).

Li et al., 96 *Polymeric Materials Science and Engineering (PMSE) Preprints* 757 (2007).

Liang, Y. et al., "Development of New Semiconducting Polymers for High Performance Solar Cells," 131 *J. Am. Chem. Soc.* 56 (2009).

Liu, J. et al., "Highly Disordered Polymer Field Effect Transistors N-Alkyl Dithieno[3,2-b2',3'-d]pyrrole-Based Copolymers," 130 *J. Am. Chme. Soc.* 13167 (2008).

Liu, K. et al., "Novel 1,4-diketo-3,6-diphenyl pyrrolo[3,4-c]pyrrole (DPP)-based copolymers with large Stokes shift," 111 *J. App. Polymer Sci.* 1976 (2009).

Loewe, R. et al., "A Simple Method to Prepare Head-to-Tail Coupled, Regioregular Poly(3-alkylthiophenes) Using Grignard Metathesis," 11 *Adv. Mater.* 250 (1999).

McCullough, R., "The Chemistry of Conducting Polythiophenes," 10 *Adv. Mater.* 93 (1998).

McCullough, R. et al., "Design, synthesis, and control of conducting polymer architectures structurally homogeneous poly(3-alkylthiophenes)," 58 *Org. Chem.* 904 (1993).

McCullough, R., "Regioregular, Head-to-Tail Coupled Poly(3-alkylthiophene) and its Derivatives," *Handbook of Conducting Polymers*, 2nd Ed. 225-258 (1998).

Miyaura, E., *Cross-Coupling Reactions A Practical Guide* (2002).

Negishi, E., *Handbook of Organopalladium Chemistry for Organic Synthesis* (2002).

Nielsen, C. et al., "New Regiosymmetrical Dioxopyrrolo- and Dihydropyrrolo-Functionalized Polythiophenes," 6 *Org. Letters* 3381 (2004).

Niu, Y. et al., "Enhancing the Performance of Polymer Light-Emitting Diodes by Integrating Self-Assembled Organic Nanowires," 20 *Adv. Mater.* 964-969 (2008).

Ogawa, K. et al., "N-Functionalized Poly(dithieno[3,2-b2',3'-d]pyrrole)s Highly Fluorescent Materials with Reduced Band Gaps," 39 *Macromolecules* 1771 (2006).

Peet, J. et al., "Efficiency enhancement in low-bandgap polymer solar cells by processing with alkane dithiols," 6 *Nat. Mater.* 497 (2007).

Peet, J. et al., "Small molecule sensitizers for near-infrared absorption in polymer bulk heterojunction solar cells," 93 *Appl. Phys. Lett.* 163306 (2009).

Petrova-Koch, V., ed., et al., *High-Efficient Low-Cost Photovoltaics*, Springer (2009).

Pomerantz, M et al., "Ester substituted bithiophenes. Abnormally low dihedral angle and rotation barrier due to dipolar stabilization," 40 *Tetrahedron Lett.* 3317 (1999).

Pomerantz, M., "Planar 2,2'-bithiophenes with 3,3'- and 3,3',4,4'-substituents. A computational study," 44 *Tetrahedron Lett.* 1563 (2003).

Pomerantz, M et al., "Studies of planar poly(3,4-disubstituted-thiophenes)," 135-136 *Synth. Met.* 257 (2003).

Pope, M. et al., *Electronic Processes in Organic Crystals and Polymers*, $2^{nd}$ ed., Oxford University Press (1999).

Rieger, R. et al., "Rational Optimization of Benzo[2,1-b;3,4-b']dithiophene-Containing Polymers for Organic Field-Effect Transistors," 22 *Adv. Mater.* 83 (2009).

Schmidt, R. et al., "High-Performance Air-Stable n-Channel Organic Thin Film Transistors Based on Halogenated Perylene Bisimide Semiconductors," 131 *J. Am. Chem. Soc.* 6215 (2009).

Smith, M., ed., et al., *March's Advanced Organic Chemistry: Reactions, Mechanisms, and Structure*, 6th ed, Wiley (2007).

Song, C., et al., "Reactive Conducting Thiepin Polymers," 75 *J. Org. Chem.* 999 (2010).

Stille, J., "The Palladium-Catalyzed Cross-Coupling Reactions of Organotin Reagents with Organic Electrophiles [New Synthetic Methods (58)]," 25 *Angew. Chem. Int. Ed.*, Engl. 508 (1986).

Sun, S., ed., et al., *Organic Photovoltaics: Mechanisms, Materials, and Devices*, CRC Press (2005).

Tamayo, A. et al., "A Low Band Gap, Solution Processable Oligothiophene with a Diketopyrrolopyrrole Core for Use in Organic Solar Cells," 112 *J. Phys. Chem. C* 11545 (2008).

Tamayo, a. et al., "A low band gap, solution processable oligothiophene with a dialkylated diketopyrrolopyrrole chromophore for use in bulk heterojunction solar cells," 94 *App. Phys. Lett.* 103301 (2009).

Tantiwiwat, M. et al., "Oligothiophene Derivatives Functionalized with a Diketopyrrolopyrrolo Core for Solution-Processed Field Effect Transistors: Effect of Alkyl Substituents and Thermal Annealing," 111 *J. Phys. Chem C* 17402 (2008).

Tovar, J. et al., "Poly(naphthodithiophene)s: Robust, Conductive Electrochromics via Tandem Cyclization—Polymerizations," 13 *Adv. Mater.* 1775 (2001).

Tovar, J. et al., "Functionalizable Polycyclic Aromatics through Oxidative Cyclization of Pendant Thiophenes," 124 *J. Am. Chem. Soc.* 7762 (2002).

Usta, H. et al., "Dithienosilole- and Dibenzosilole-Thiophene Copolymers as Semiconductors for Organic Thin-Film Transistors," 128 *J. Am. Chem. Soc.* 9034 (2006).

Vala, M. et al., "Comparative Studies of Diphenyl-Diketo-Pyrrolopyrrole Derivatives for Electroluminescence Applications," 18 *J. Fluorescence* 1181 (2008).

Watanabe, H. et al., "esis of Alkylated Benzo[2,1-b:3,4-b']dithiophenes by Annulative Coupling and Their Direct Arylation under Palladium Catalysis," 36 *Chem. Letters* 1336 (2007).

Wei, Q. et al., "Self-Organized Buffer Layers in Organic Solar Cells," 20 *Adv. Mater.* 2211 (2008).

Wienk, M. et al., "Narrow-Bandgap Diketo-Pyrrolo-Pyrrole Polymer Solar Cells: The Effect of Processing on the Performance," 20 *Adv. Mat.* 2556 (2008).

Wobkenberg, P. et al., "Fluorine containing C60 derivatives for high-performance electron transporting field-effect transistors and integrated circuits," 92 *Appl. Phys. Lett.* 143310 (2008).

Xiao, S. et al., "Conjugated Polymers of Fused Bithiophenes with Enhanced π-Electron Delocalization for Photovoltaic Applications," 41 *Macromolecules* 5688 (2008).

Xu, Z. et al., "Vertical Phase Separation in Poly(3-hexylthiophene): Fullerene Derivative Blends and its Advantage for Inverted Structure Solar Cells," 19 *Adv. Functional Mater.* 1227 (2009).

Yamamoto, T. et al., "Preparation π-conjugated poly(thiophene-2,5-diyl), poly(p-phenylene), and related polymers using zerovalent nickel complexes," 25 *Macromolecules* 1214 (1992).

Yokoyama, A. et al., "Chain-Growth Polymerization for Poly(3-hexylthiophene) with a Defined Molecular Weight and a Low Polydispersity," 37 *Macromolecules* 1169 (2004).

Yoshida, S. et al., "Novel Electron Acceptors Bearing a Heteroquinonoid System. 4. Syntheses, Properties, and Charge-Transfer Complexes of 2,7-Bis(dicyanomethylene)-2,7-dihydrobenzo[2,1-b:3,4-b']dithiophene, 2,7-Bis(dicyanomethylene)-2,7-dihydrobenzo[1,2-b:4,3-b']dithiophene, and 2,6-Bis(dicyanomethylene)-2,6-dihydrobenzo[1,2-b:4,5-b']dithiophene," 59 *J. Org. Chem.* 3077 (1994).

Zhang, Q. et al., "Alternating Donor/Acceptor Repeat Units in Polythiophenes. Intramolecular Charge Transfer for Reducing Band Gaps in Fully Substituted Conjugated Polymers," 120 *J. Am. Chem. Soc.* 5355 (2008).

Zhang, Q. et al, "Low Optical Bandgap Polythiophenes by an Alternating Donor/Acceptor Repeat Unit Strategy," 119 *J. Am. Chem. Soc.* 5065 (1997).

Zhu, Y., *New Diketopyrrolopyrrole(DPP)-Based Conjugated Polymers Prepared upon Palladium Catalyzed Polymerization and Electropolymerization Reactions*, Dissertation, University of Koln (2006).

R: ethylhexyl

R: ethylhexyl

Figure 7: Donors
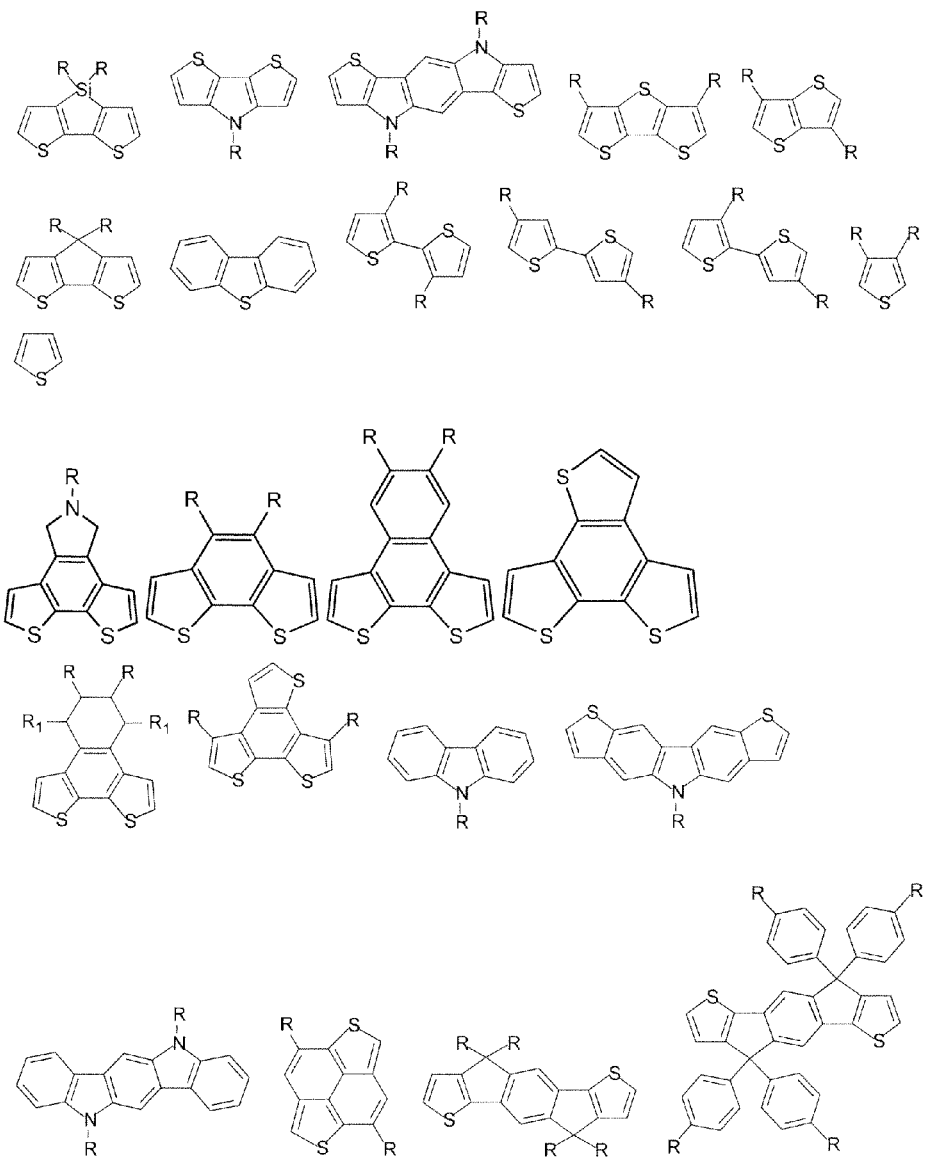

Figure 8: Acceptors
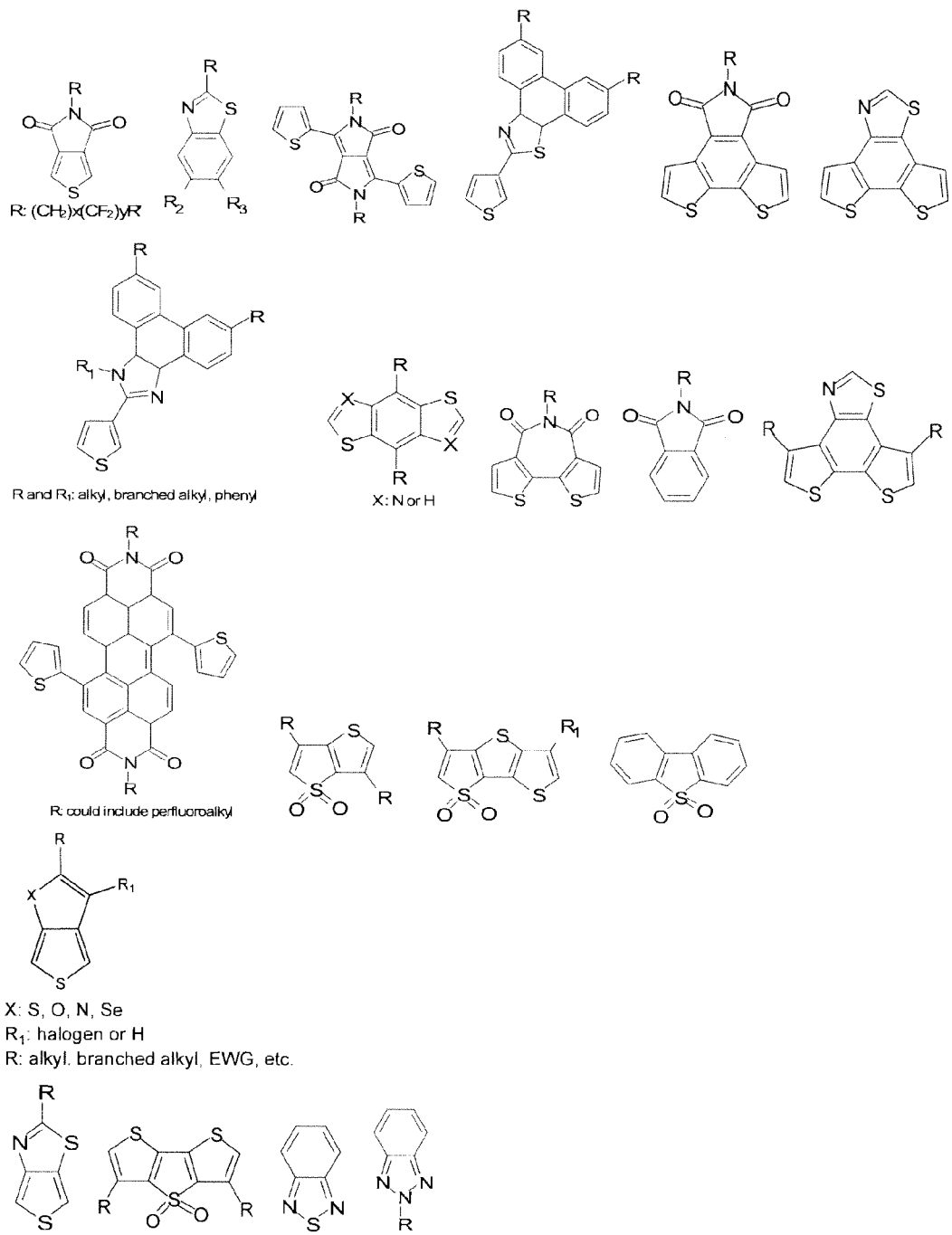

COMPOSITIONS, METHODS AND POLYMERS

RELATED APPLICATIONS

This application claims priority to U.S. provisional application Ser. Nos. 61/222,053 filed on Jun. 30, 2009; Ser. No. 61/240,137 filed Sep. 4, 2009; 61/241,813 filed Sep. 11, 2009; 61/248,335 filed Oct. 2, 2009; 61/289,314 filed Dec. 22, 2009; 61/290,844 filed Dec. 29, 2009; and 61/307,387 filed Feb. 23, 2010, which are each hereby incorporated by reference in its entirety.

BACKGROUND

Conjugated organic polymers, or intrinsically conductive polymers, have become an economically important class of conductive material in a variety of applications such as, for example, organic light-emitting diodes (OLEDs), field effect transistors (FET), photovoltaic devices (OPVs), and printed electronics generally. Commercial interest arises in part due to the advances in the ability to control the optical and electronic properties of the polymers. In particular, an important aspect of conjugated polymers is the ability to tune the band gap of the polymer, and a particular need exists in the development of new polymeric architectures with specifically designed electronic and optical properties, including lower band gaps, with commercially useful properties. See, for example, Bundgaard et al., "Low Band Gap Polymers for Organic Photovoltaics," *Solar Energy Materials and Solar Cells*, 91 (2007), 954-985.

In addition, as production processes for these materials are scaled-up, there is a growing need to improve the methods for making these materials including monomers, oligomers, and polymers. In particular, there is a need for methods which are easy and cost-effective and produce monomers having improved purity.

SUMMARY

Embodiments described herein include, among other things, compositions, compounds, devices, methods of making, and methods of using.

For example, one embodiment provides a composition comprising at least one donor acceptor copolymer, said at least one copolymer comprising at least one first bithiophene repeat unit represented by (I):

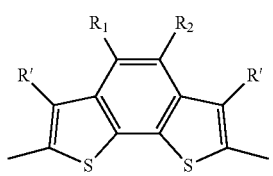

(I)

wherein $R_1$, $R_2$ and R' are solubilizing groups or hydrogen. In this formula, the short lines at the left and right sides of the formula represent linkage of the repeat unit to the copolymer backbone, not methyl groups. The copolymer can be, for example, a donor acceptor polymer and the bithiophene repeat unit can be, for example, part of the donor moiety of the donor acceptor polymer.

In one embodiment, R' are each hydrogen. In one embodiment, $R_1$ and $R_2$ are solubilizing groups. In one embodiment, R' are each hydrogen and $R_1$ and $R_2$ are each solubilizing groups. In one embodiment, $R_1$ and $R_2$ form a ring. In one embodiment, $R_1$ and $R_2$ form an aromatic ring. In one embodiment, $R_1$ and $R_2$ form a benzene ring. In one embodiment, $R_1$ and $R_2$ form a heterocyclic ring. In one embodiment, $R_1$ and $R_2$ each comprise one or more optionally substituted alkyl, optionally substituted aryl, optionally substituted heteroaryl, or optionally substituted cycloalkyl moieties.

In one embodiment, said at least one bithiophene repeat unit is represented by:

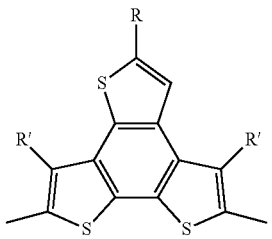

and further wherein R and R' are solubilizing groups or hydrogen.

In one embodiment, said at least one bithiophene repeat unit is represented by:

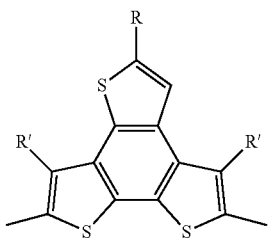

and further wherein R' is hydrogen and R is a solubilizing group.

In one embodiment, said at least one bithiophene repeat unit is represented by:

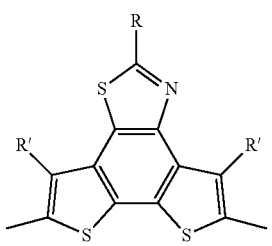

and further wherein R and R' are solubilizing groups or hydrogen.

In one embodiment, said at least one bithiophene repeat unit is represented by:

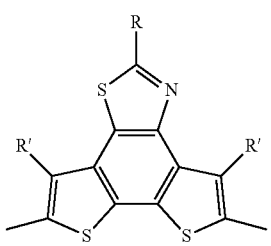

and further wherein R is a solubilizing group and R' is hydrogen.

In one embodiment, said at least one bithiophene repeat unit is represented by:

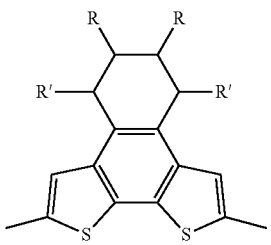

and further wherein R and R' are solubilizing groups or hydrogen.

In one embodiment, at least one bithiophene repeat unit is represented by (III):

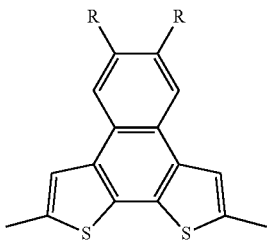

(III)
and further wherein R are solubilizing groups or hydrogen.

In one embodiment, at least one bithiophene repeat unit is represented by:

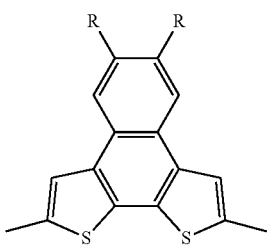

and further wherein R are solubilizing groups.

In one embodiment, at least one bithiophene repeat unit is represented by:

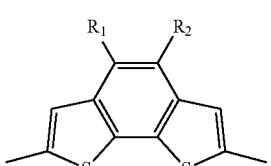

and further wherein $R_1$ and $R_2$ comprise branched alkyl groups or hydrogen.

In one embodiment, said least one bithiophene repeat unit is represented by:

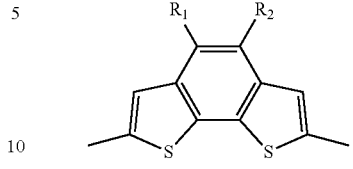

and further wherein $R_1$ and $R_2$ comprise branched alkyl groups.

In one embodiment, said at least one bithiophene repeat unit is represented by:

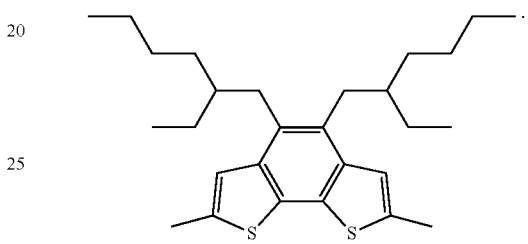

In one embodiment, said at least one bithiophene repeat unit is represented by:

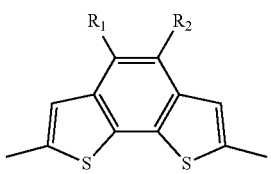

and further wherein $R_1$ and $R_2$ comprise alkyleneoxy or alkoxy groups.

In one embodiment, said at least one bithiophene repeat unit is represented by:

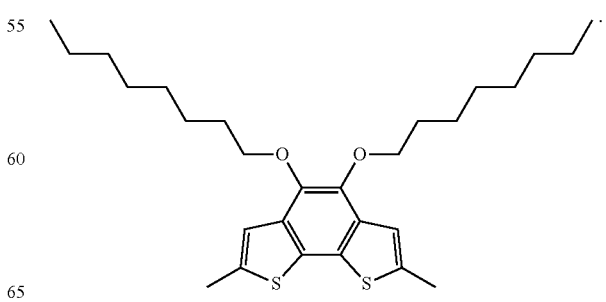

In one embodiment, said at least one bithiophene repeat unit is represented by at least one of the following:

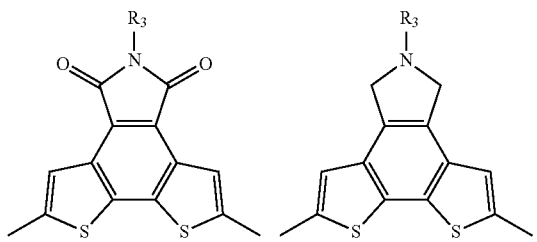

wherein R₃ is a solubilizing group.

In one embodiment, the structure (I) provides a donor to the donor acceptor copolymer. In one embodiment, said at least one copolymer is an alternating copolymer.

In one embodiment, wherein said at least one copolymer comprises repeating dimer units, said repeating dimer units comprising said at least one first bithiophene repeat unit (I) and a second repeat unit.

In one embodiment, said at least one copolymer comprises repeating dimer units, said repeating dimer units comprising said at least one first bithiophene repeat unit (I) and a second repeat unit, said second repeat unit comprising at least one ring structure.

In one embodiment, said at least one copolymer comprises repeating dimer units, said dimer units comprising said at least one first bithiophene repeat unit (I) and a second repeat unit, said second repeat unit comprising at least one fused ring structure.

In one embodiment, said at least one copolymer comprises repeating dimer units, said dimer units comprising said at least one first bithiophene repeat unit (I) and a second repeat unit, said second repeat unit comprising at least one aromatic ring structure.

In one embodiment, said at least one copolymer comprises repeating dimer units, said dimer units comprising said at least one first planarized bithiophene repeat unit (I) and a second repeat unit, said second repeat unit comprising at least one thiophene ring structure.

In one embodiment, said at least one copolymer comprises repeating dimer units, said dimer units comprising said at least one first bithiophene repeat unit (I) and a second repeat unit, said second repeat unit being represented by at least one of the following:

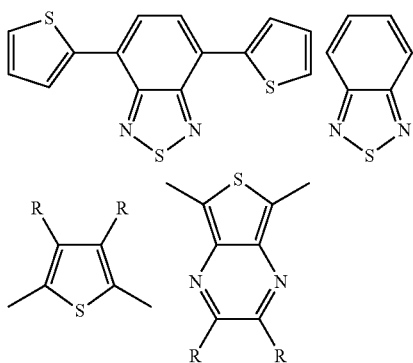

-continued

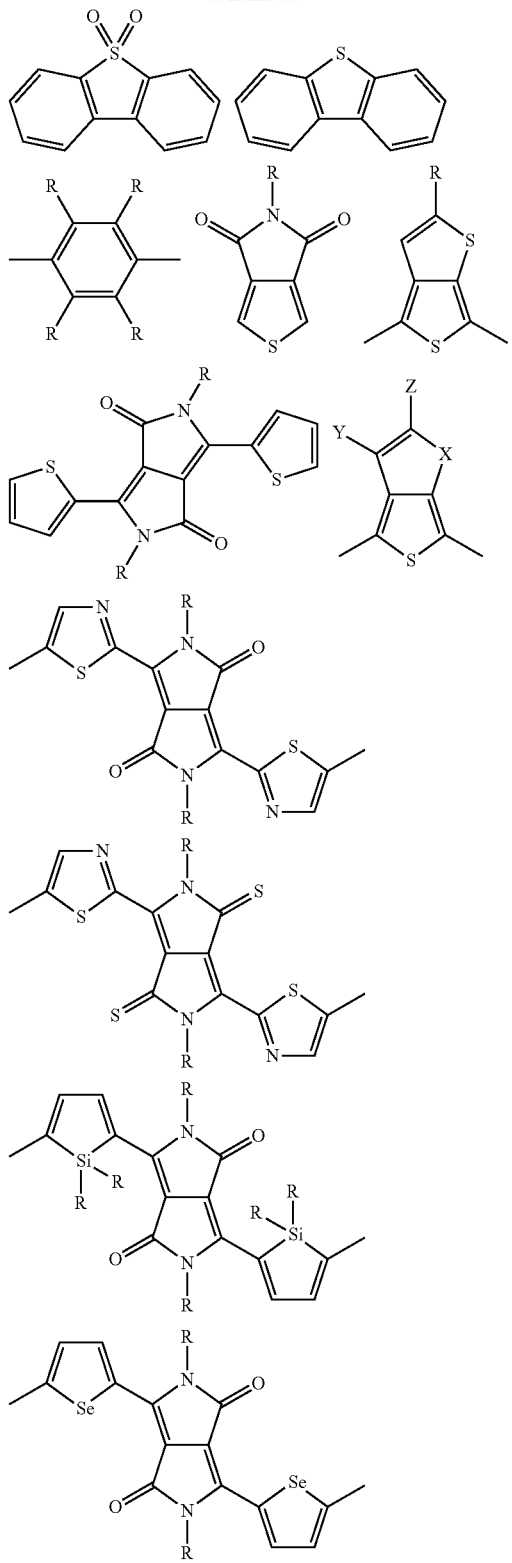

wherein R are solubilizing groups, X is sulfur, oxygen, or nitrogen, or selenium. Y is a halogen or hydrogen, and Z is alkyl or branched alkyl.

In one embodiment, said at least one copolymer comprises repeating dimer units, said dimer unit comprising said at least one first bithiophene repeat unit (I) and a second repeat unit, said second repeat unit being represented by at least one of the following:

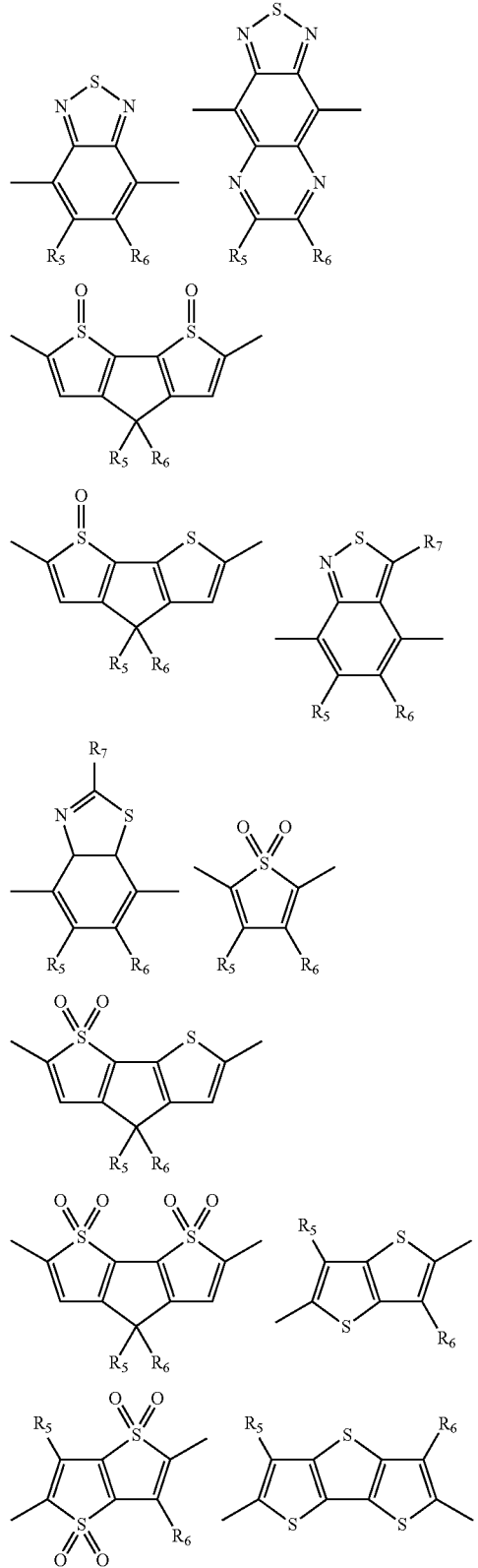

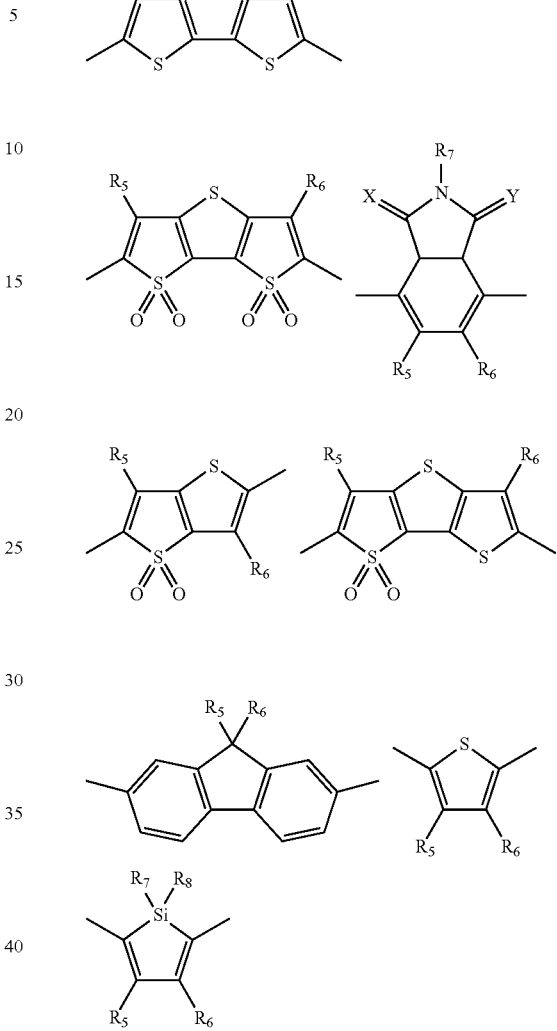

wherein $R_5$, $R_6$, $R_7$, and $R_8$ are solubilizing groups and X and Y are independently $CH_2$, O, or S.

In one embodiment, said at least one copolymer comprises repeating dimer units, said dimer units comprising at least one first bithiophene repeat unit (1) and a second repeat unit, said second repeat unit being represented by at least one of the following:

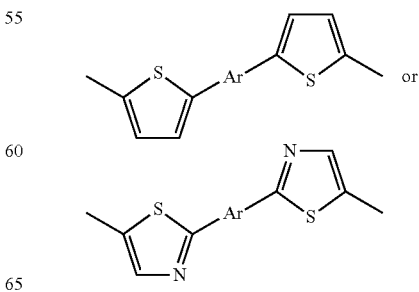

wherein Ar is represented by:

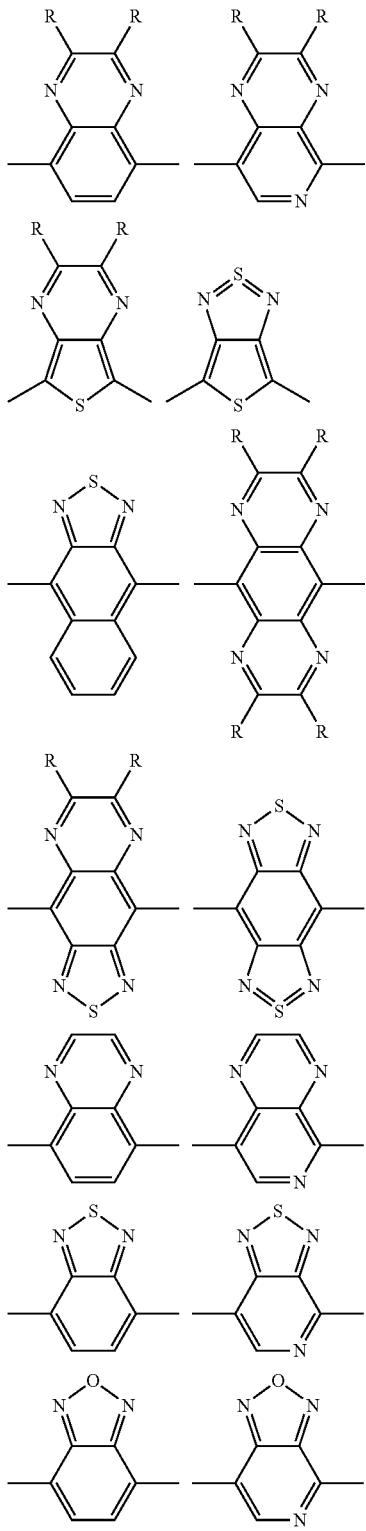

and further wherein R are solubilizing groups.

In one embodiment, said at least one copolymer further comprises a silole moiety. In one embodiment, said at least one copolymer further comprises a moiety represented by:

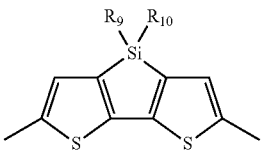

wherein $R_9$ and $R_{10}$ are independently optionally substituted alkyl, optionally substituted aryl or heteroaryl, optionally substituted alkenyl, or optionally substituted alkynyl.

In one embodiment, said at least one copolymer further comprises at least one second planarized repeat unit represented by:

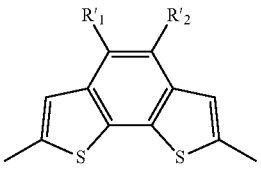

wherein $R_1'$ and $R_2'$ are solubilizing groups or hydrogen, and further wherein said at least one first bithiophene repeat unit and said at least one second bithiophene repeat unit are not identical.

In one embodiment, the copolymer has a degree of polymerization of 5 to 100,000. In one embodiment, the copolymer has a degree of polymerization of 10 to 10,000.

In one embodiment, the copolymer comprises at least two different donors, or the copolymer comprises at least two different acceptors. In one embodiment, the copolymer is prepared by an alternating copolymerization of at least two monomers.

Another embodiment provides a composition comprising at least one donor acceptor copolymer, said at least one copolymer comprising at least one first bithiophene repeat unit represented by:

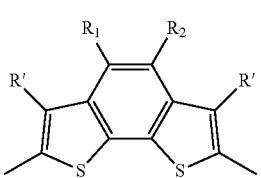

wherein $R_1$ and $R_2$ and $R'$ are solubilizing groups or hydrogen, further wherein said at least one copolymer does not comprise poly[2,6-(4,4-dioctyl-4H-cyclopenta[2,1-b:3,4-b']dithiophene)-alt-2,7-(4,5-dioctylbenzo[2,1-b:3,4-b']dithiophene)], poly[2,6-(4,4-dioctyl-4H-cyclopenta[2,1-b:2,4-b']dithiophene)-alt-2,9-(5,6-dioctylnaphtho[2,1-b:3,4-b']dithiophene)], or poly[2,6-(4,4-dioctyl-4H-cyclopenta[2,1-b:3,4-b']dithiophene)-alt-6,9-(2,3-bis((S)-2,6-dimethylheptyl)ditheno[3,2-f:2',3'-h]quinoxaline].

Another embodiment provides a composition comprising at least one donor acceptor copolymer, said at least one copolymer comprising at least one repeat unit represented by (II):

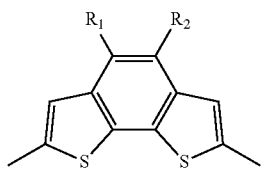

(II)

wherein $R_1$ and $R_2$ each comprise one or more optionally substituted alkyl, optionally substituted alkyleneoxy, optionally substituted alkoxy, optionally substituted aryl, optionally substituted heteroaryl, or optionally substituted cycloalkyl moieties, or optionally form an optionally substituted ring.

Another embodiment provides a composition comprising at least one donor acceptor copolymer, said at least one copolymer comprising as donor at least one first bithiophene repeat unit (I) represented by:

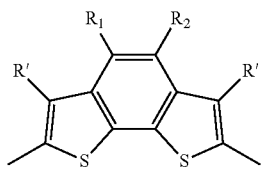

(I)

wherein $R_1$, $R_2$ and $R'$ are solubilizing groups or hydrogen, wherein the copolymer further comprises at least one repeat moiety represented by:

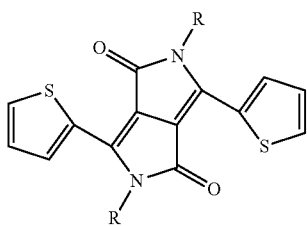

wherein R is a solubilizing group.

Another embodiment is a composition comprising at least one donor acceptor copolymer, said at least one copolymer comprising as donor at least one first bithiophene repeat unit represented by:

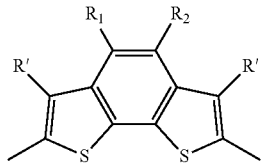

wherein $R_1$, $R_2$ and $R'$ are solubilizing groups or hydrogen, wherein the copolymer further comprises at least one repeat moiety represented by:

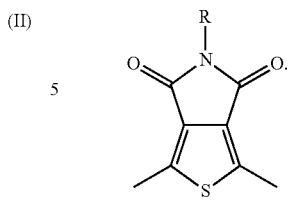

Another embodiment is a composition comprising at least one donor acceptor copolymer, said at least one copolymer comprising as donor at least one first bithiophene repeat unit (I) represented by:

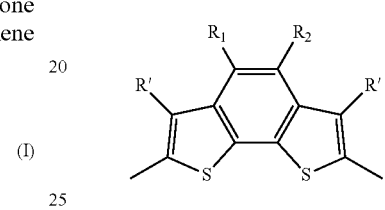

(I)

wherein $R_1$, $R_2$ and $R'$ are solubilizing groups or hydrogen, wherein the copolymer further comprises at least one additional repeat moiety which is an acceptor.

Still further, another embodiment is a composition comprising at least one donor acceptor copolymer, said at least one copolymer comprising as donor at least one first bithiophene repeat unit represented by:

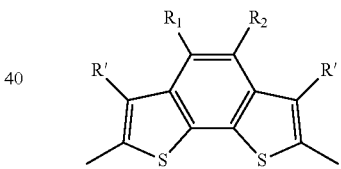

wherein $R_1$, $R_2$ and $R'$ are solubilizing groups or hydrogen, wherein the copolymer further comprises at least one repeat moiety represented by structure VIII and substructure IX:

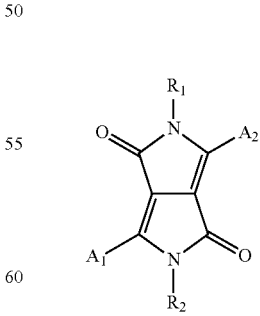

(VIII)

wherein A1 and A2 each independently comprise a fused ring system comprising at least two fused rings directly covalently linked to the substructure of VIII represented as substructure IX:

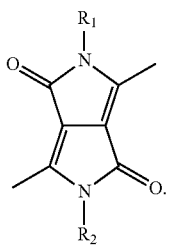

(IX)

Another embodiment provides a composition comprising at least one donor acceptor conjugated copolymer, wherein the polymer comprises at least one first donor, at least one first acceptor, and at least one second donor or second acceptor different from the first donor or first acceptor, and wherein the polymer comprises at least one benzo[2,1-b:3,4-b'] dithiophene moiety in the polymer backbone.

Another embodiment provides a composition comprising a mixture comprising: (i) at least one p-type material, (ii) at least one n-type material, wherein the at least one p-type material comprises at least one donor acceptor copolymer, said at least one copolymer comprising as donor at least one first bithiophene repeat unit represented by:

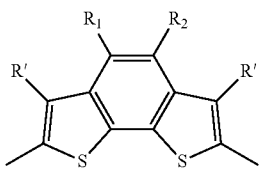

(I)

wherein $R_1$, $R_2$, and $R'$ are solubilizing groups or hydrogen.

Another embodiment comprises a composition comprising at least one donor acceptor dimer or trimer, said at least one donor acceptor dimer or trimer comprising at least one first structure as donor represented by:

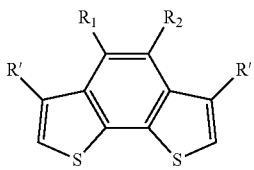

wherein $R_1$, $R_2$, and $R'$ are solubilizing groups or hydrogen. Other higher order oligomers can be prepared with, for example, four, five, or six repeat units.

Another embodiment provides a method comprising: providing at least one compound comprising at least one first thiophene ring which comprises a substituent at the 3 position, wherein the substituent comprises a C2 linkage group which links the first thiophene ring to a second thiophene ring at the 4 position of the second thiophene ring, reacting the compound so that ring closure occurs to form a benzo[2,1-b: 3,4-b']dithiophene moiety, wherein the reacting step is carried out in the presence of a Lewis or Bronsted acid and an oxidant.

In one embodiment, the C2 linkage is part of an aromatic ring, including a benzene ring. It can be part of a heterocyclic ring.

In one embodiment, the Lewis acid is selected from the group consisting of $BF_3$, $BF_3 \cdot (C_2H_5)_2O$, $BCl_3$, $AlCl_3$, $Al(CH_3)_3$, $TiCl_4$, $ZrCl_4$, $SnCl_4 \cdot 5H_2O$, $SnF_4$, $VCl_4$, $SbF_5$, $ScCl_3$, $ScCl_3 \cdot 6H_2O$, $Sc(CF_3SO_3)_3$, $La(CH_3CO_2) \cdot xH_2O$, $LaCl_3$, $LaCl_3 \cdot 7H_2O$, $LaF_3$, $La(NO_3)_3 \cdot 6H_2O$, $La(C_2O_4)_3 \cdot xH_2O$, $La(SO_4)_3 \cdot xH_2O$, $La(CF_3SO_3)_3$, $ZnCl_2$, $ZnBr_2$, $ZnF_2$, $Zn(CH_3CO_2)_2$, $Zn(CH_3CO_2)_2$, $Zn(CH_3CO_2)_2 \cdot 2H_2O$, $ZnSiF_6 \cdot xH_2O$, $Zn(NO_3)_2 \cdot xH_2O$, $Zn(C_2O_4)_2 \cdot xH_2O$, and $Nd(CF_3SO_3)_3$.

In one embodiment, the Bronsted acid is selected from the group consisting of $CF_3SO_3H$, $C_6H_5SO_3H$, $CH_3SO_3H$, $CF_3CO_2H$, $CCl_3CO_2H$, $CHCl_2CO_2H$, $CFH_2CO_2H$, $CClCH_2CO_2H$, $HCO_2H$, $C_6H_5CO_2H$, $CH_3CO_2H$, $HBF_4$, $H_2SO_4$, $FSO_3H$, and $HPF_6$.

In one embodiment, the oxidant is an organic oxidant. In one embodiment, the oxidant is a quinone oxidant. In one embodiment, the oxidant is a quinone oxidant selected from the group consisting of 2,3-dichloro-5,6-dicyanobenzoquinone, 1,4-benzoquinone, 1,2-benzoquinone, o-tetrafluorobenzoquinone, p-tetrafluorobenzoquinone, tetracyanobenzoquinone, o-chloranil, p-chloronil, 1,4-naphthoquinone, anthraquinone, 2,6-diphenylbenzoquinone, and 2,6-di-tert-butylbenzoquinone.

In one embodiment, the oxidant is at least one hypervalent iodine compound, CoF3/trifluoroacetic acid, vanadyloxide, quinone imine, quinine diimine, nitroarene, triarylammonium salt.

In one embodiment, the ring closure is the primary reaction over oligomerization or polymerization of the thiophene. In one embodiment, the ring closure reaction is carried out in the absence of transition metals.

Another embodiment provides a method comprising cyclizing a compound of formula II,

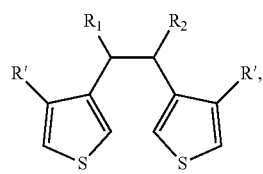

(IV)

in the presence of a Lewis or Bronsted acid and an oxidant to produce the compound of formula I,

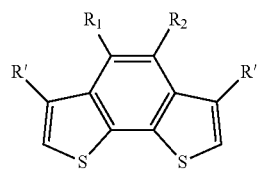

(V)

wherein $R_1$ and $R_2$ each comprise one or more optionally substituted alkyl, optionally substituted alkoxy, optionally substituted aryl, optionally substituted heteroaryl, optionally substituted cycloalkyl and optionally substituted heterocyclyl group, or form an optionally substituted ring, and R' are solubilizing groups or hydrogen.

In one embodiment, $R_1$ and $R_2$ form a benzene ring.

In one embodiment, the compound of formula IV has the formula IVA,

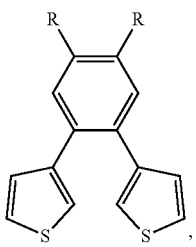

(IVA)

and the compound of formula V has the formula VA,

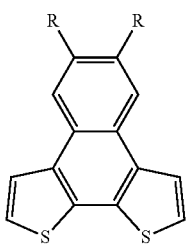

(V-A)

wherein R are solubilizing groups.

In one embodiment, the Lewis acid is selected from the group consisting of $BF_3$, $BF_3.(C_2H_5)_2O$, $BCl_3$, $AlCl_3$, $Al(CH_3)_3$, $TiCl_4$, $ZrCl_4$, $SnCl_4$, $SnCl_4.5H_2O$, $SnF_4$, $VCl_4$, $SbF_5$, $ScCl_3$, $ScCl_3.6H_2O$, $Sc(CF_3SO_3)_3$, $La(CH_3CO_2).xH_2O$, $LaCl_3$, $LaCl_3.7H_2O$, $LaF_3$, $La(NO_3)_3.6H_2O$, $La(C_2O_4)_3.xH_2O$, $La(SO_4)_3.xH_2O$, $La(CF_3SO_3)_3$, $ZnCl_2$, $ZnBr_2$, $ZnF_2$, $Zn(CH_3CO_2)_2$, $Zn(CH_3CO_2)_2$, $Zn(CH_3CO_2)_2.2H_2O$, $ZnSiF_6.xH_2O$, $Zn(NO_3)_2.xH_2O$, $Zn(C_2O_4)_2.xH_2O$, and $Nd(CF_3SO_3)_3$.

In one embodiment, the Bronsted acid is selected from the group consisting of $CF_3SO_3H$, $C_6H_5SO_3H$, $CH_3SO_3H$, $CF_3CO_2H$, $CCl_3CO_2H$, $CHCl_2CO_2H$, $CFH_2CO_2H$, $CClCH_2CO_2H$, $HCO_2H$, $C_6H_5CO_2H$, $CH_3CO_2H$, $HBF_4$, $H_2SO_4$, $FSO_3H$, and $HPF_6$.

In one embodiment, the oxidant is an organic oxidant. In one embodiment, the oxidant is a quinone oxidant. In one embodiment, the oxidant is a quinone oxidant selected from the group consisting of 2,3-dichloro-5,6-dicyanobenzoquinone, 1,4-benzoquinone, 1,2-benzoquinone, o-tetrafluorobenzoquinone, p-tetrafluorobenzoquinone, tetracyanobenzoquinone, o-chloranil, p-chloronil, 1,4-naphthoquinone, anthraquinone, 2,6-diphenylbenzoquinone, and 2,6-di-tert-butylbenzoquinone.

In one embodiment, the oxidant is at least one hypervalent iodine compound, CoF3/trifluoroacetic acid, vanadyloxide, quinone imine, quinine diimine, nitroarene, or triarylammonium salt.

In one embodiment, the method further comprises use of a solvent selected from the group consisting of dichloromethane, di chloroethane, toluene, propionitrile, trifluoroacetic acid, methanesulfonic acid, carbon tetrachloride, chlorobenzene, tetrachloroethane, hexafluoroisopropanol, perfluorinated solvent, and partially fluorinated solvent.

In one embodiment, the Lewis and Bronsted acid and the oxidant are not $FeCl_3$, palladium acetate, hypervalent iodine, or $CoF_3$.

In one embodiment, the method further comprises functionalizing the reaction product to form a polymerization monomer.

Another embodiment provides a method comprising: providing a first thiophene compound, said first thiophene compound comprising a first thiophene ring, said first thiophene ring having a first halogen attached to its 2-position and a first carbon attached to its 3-position; providing a second thiophene compound, said second thiophene comprising a second thiophene ring, said second thiophene ring having a second halogen attached to its 2-position and a second carbon attached to its 3-position; forming a first bond between said first carbon and said second carbon; and dehalogenating said first halogen and said second halogen to form a second bond between said first thiophene ring and said second thiophene ring, thereby forming a product comprising said first thiophene ring and said second thiophene ring.

Other embodiments provides an ink composition comprising the compositions described herein including copolymer composition, and including p-type and n-type materials, and including solvents. These compositions can be also disposed in electronic devices such as a photovoltaic cell including the active layer.

Examples of one or more advantages for at least some embodiments can be: better reaction control during monomer preparation, reduction of impurities in final product during monomer preparation, reduction of side products during reaction to form monomer, fine control of copolymer microstructure (including, for example, structural homogeneity and regiospecificity), ability to tune the electronic properties of the copolymer, reduced band gap in the conjugated polymer, improved mobility, improved photovoltaic cell efficiency, stable oxidation state, improved environmental stability, good solubility, good processability, and/or long term resistance to oxidation. While not limited by theory, it is also believed that the benzo[2,1-b:3,4-b']dithiophene moiety can facilitate better side group alignment and surface presentation of side groups compared to use of, for example, the benzo[2,1-b:4,5-b']dithiophene moiety. An advantage can in some cases be found with blending the benzo[2,1-b:3,4-b'] dithiophene moiety with the benzo[2,1-b:4,5-b']dithiophene moiety in a copolymer microstructure.

BRIEF DESCRIPTION OF THE FIGURES

FIG. 8 provides examples of acceptor structures in a donor acceptor copolymer.

DETAILED DESCRIPTION

Introduction

Figure 1:
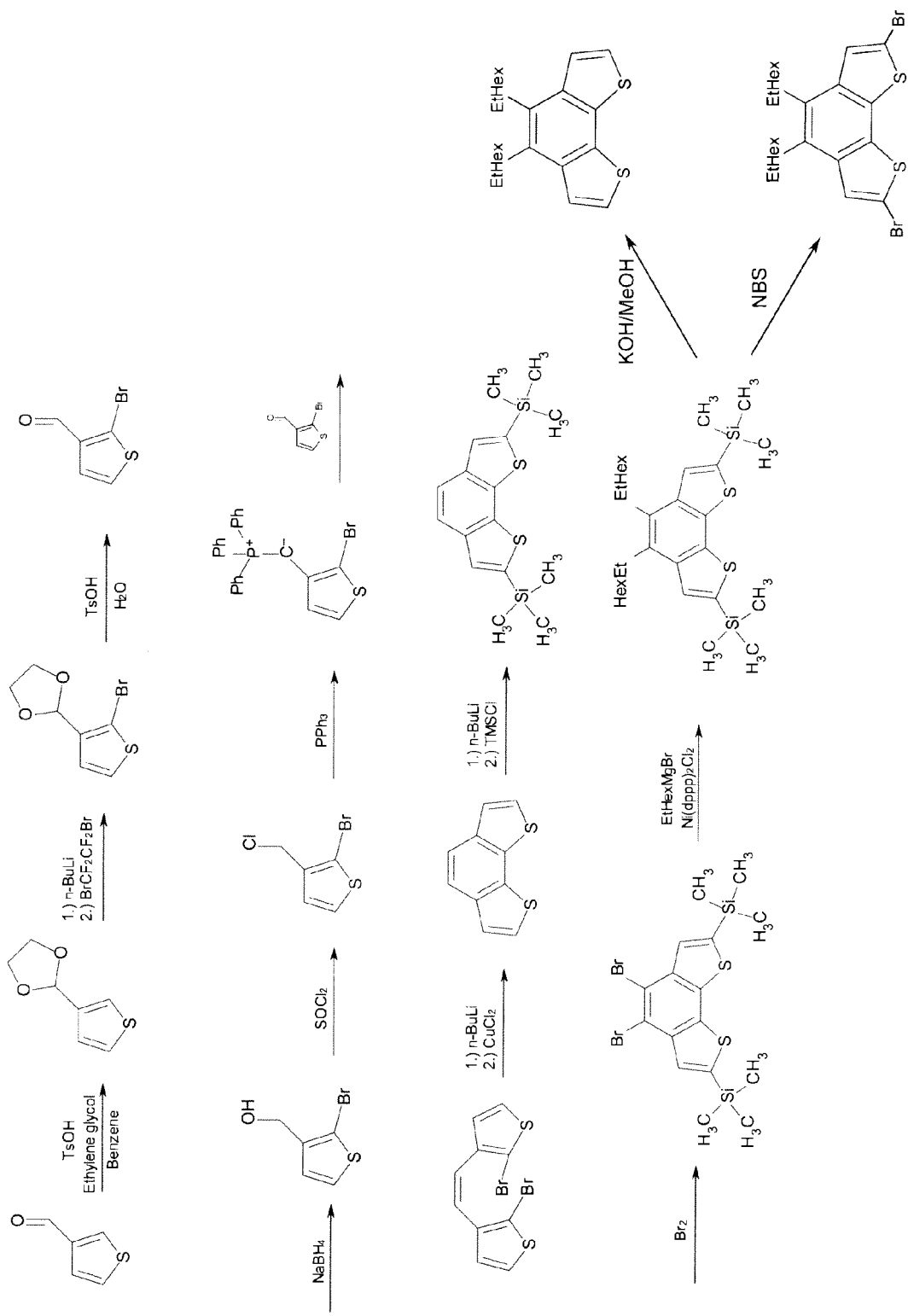
FIG. 1 illustrates synthesis of repeat units.

All references cited herein are incorporated by reference in their entirety.

US provisional priority filing Ser. No. 61/222,053 filed Jun. 30, 2009 is incorporated by reference in its entirety.

The following provisional applications are also incorporated by reference in their entireties: Ser. No. 61/240,137 filed Sep. 4, 2009; 61/241,813 filed Sep. 11, 2009; 61/248,335 filed Oct. 2, 2009; 61/289,314 filed Dec. 22, 2009; 61/290,844 filed Dec. 29, 2009; and 61/307,387 filed Feb. 23, 2010, particularly for embodiments which include making and characterizing monomers, oligomers, and polymers comprising the benzo[2,1-b:3,4-b']dithiophene moiety, including donor-acceptor polymers, ink formulations, film formation, and devices, including organic photovoltaic devices. Examples of donors for donor acceptor polymers and acceptors for donor acceptor polymers can be found in FIGS. 7 and 8, respectively.

Methods for synthesizing benzo[2,1-b:3,4-b']dithiophene monomers are known in the art. See for example (a) Tovar et al., *J. Am. Chem. Soc.,* 2002, 124, 7762-7769, (b) Huo et al., *Macromol.,* 2009, 42(17), 6564-6571, (c) Niu et al., *Adv. Mater.,* 2008, 20, 964-969, (d) Chen et al., *J. Am. Chem. Soc.,* 2010, 132, 1328-1333, (e) Swager et al., *Adv. Mater.,* 2001, 13, 1775, (f) Song et al., *J. Org. Chem.,* 2010, 75, 999-1005, (g) Xiao et al., *Macromolecules,* 2008, 41, 5688-5696, (h) Rieger et al., *Adv. Mater.,* 2009, 21, 1-4; (i) US Pat. Pub. 2009/0065770. See also, WO 2010/000669 (BASF). It appears that these processes often use ferric chloride as the oxidant for ring closure. However, $FeCl_3$, has a much greater oxidizing strength and is more likely to form of a variety of impurities such as chlorinated products or oligomerization or polymerization products. Typically, such reactions require a large excess of $FeCl_3$ and result in products which are contaminated with chlorinated impurities. Moreover, $FeCl_3$ can provide for formation of an undesired Bronsted Acid (e.g., HCl) and thus is a less clean reaction. Consequently isolation of products and recycling of reagents is generally difficult in such reactions. Other methods such as electrochemical cyclization, may be in some cases an alternative on the lab scale, but it is not in many cases practicable on an industrial scale.

Homopolymers are generally known in the art. See for example Elias, *An Introduction to Polymer Science*, VCH, 1997, Chapter 2. Copolymers and copolymer architecture are also generally known in the art. See, for example, Billmeyer, *Textbook of Polymer Science,* $3^{rd}$ Ed, 1984 (e.g., Chapter 5); *Concise Encyclopedia of Polymer Science and Engineering*, (Kroschwitz, Ed.), 1990 "Copolymerization" and "Alternating Copolymers." As an example, copolymers include block copolymers, segmented copolymers, graft, alternating copolymers, random copolymers, and the like. Copolymers include polymers with two or more different types of repeat groups, including terpolymers.

Conjugated polymers are also generally known in the art. The homopolymers and copolymers described herein are examples. Other examples include polythiophenes (including regioregular polythiophene derivatives), polypyrroles, poly(phenylene vinylenes), polyanilines, and the like.

U.S. Pat. No. 6,166,172 describes the GRIM method of forming, for example, a regioregular poly (3-substituted thiophene) from a polymerization reaction. The method proceeds by combining, for example, a soluble thiophene having at least two leaving groups with an organometal, e.g., organomagnesium, reagent to form a regiochemical isomer intermediate, and adding thereto an effective amount of, for example, Ni(II) complex to initiate the polymerization reaction.

U.S. patent application Ser. No. 12/371,556 filed Feb. 13, 2009 to Sheina, incorporated by reference in its entirety, describes compositions, methods, and polymers comprising, for example, dithieno[3,2-b:2',3'-d]pyrrole repeat units.

Organic electronic devices are known in the art.

P-type donor material and n-type materials for use in OPV active layers are described in U.S. patent application Ser. No. 11/745,587 to Laird et al., filed May 2, 2007, and U.S. patent application Ser. No. 12/340,587 to Laird et al., filed Dec. 19, 2008, both of which are incorporated by reference in their entirety.

Additional description of methods may be found in, for example, McCullough et al., *J. Org. Chem.,* 1993, 58, 904-912, and U.S. Pat. No. 6,602,974, including formation of block copolymers, to McCullough, et al.

Additional description can be found in the articles, "The Chemistry of Conducting Polythiophenes," by Richard D. McCullough, *Adv. Mater.* 1998, 10, No. 2, 93-116, and references cited therein, and Lowe, et al., *Adv. Mater.* 1999, 11, 250, which are hereby incorporated by reference in its entirety. The Handbook of Conducting Polymers, 2nd Ed., 1998, Chapter 9, by McCullough, et al., "Regioregular, Head-to-Tail Coupled Poly(3-alkylthiophene) and its Derivatives," pages 225-258, is also hereby incorporated by reference in its entirety.

For preparing polymers, Grignard metathesis reactions are known in the art, an example of which is described by L. Boymond et al., *Angew. Chem. Int. Ed.,* 1998, 37, No. 12, pages 1701-1703, which is incorporated herein by reference in its entirety. Additionally, broader range of metal mediated coupling reactions may be considered: (a) *Cross-Coupling Reactions: A Practical Guide*, Ed. Miaura, 2002, (b) *Handbook of Organopalladium Chemistry for Organic Synthesis*, Ed. Negishi, 2002, (c) Kuwano, R., Utsunomia, M., Hartwig, J. F., *J. Org. Chem.,* 2002, 67, 6479-6486, (d) Yu et a., *J. Am. Chem. Soc.,* 2009, 131, 56, (e) Yang et al., *Macromol.,* 2008, 41, 6012, (f) LeClerc et al., *J. Am. Chem. Soc.,* 2008, 130, 732, (g) Swager et al., *Adv. Mater.,* 2001, 13, 1775, (h) Koeckelberghs et al., *Macromol.,* 2007, 40, 4173. If a side group on a monomer is reactive with the organomagnesium reagent, a protective group can be coupled with the side group to prevent side group from taking part in the synthesis. The use of protective groups is well known in the art, as described by Greene and Greene, *"Protective Groups in Organic Synthesis,"* John Wiley and Sons, New York (1981), which is incorporated herein by reference. One skilled in the art can use protective groups and deprotection synthetic strategies in order to introduce certain functional groups which may otherwise be undesirably reactive under certain desired reaction conditions. See, for example, March's *Advanced Organic Chemistry, Reactions, Mechanisms, and Structure,* $6^{th}$ Ed, 2007.

"Optionally substituted" groups refers to functional groups that may be substituted or unsubstituted by additional functional groups. When a group is unsubstituted by an additional group it may be referred to as a group name, for example alkyl or aryl. When a group is substituted with additional functional groups it may more generically be referred to as substituted alkyl or substituted aryl, respectively.

"Aryl" refers to, for example, an aromatic carbocyclic group of from 6 to 20 carbon atoms having a single ring (e.g., phenyl) or multiple condensed rings (e.g., naphthyl or anthryl) which condensed rings may or may not be aromatic provided that the point of attachment is at an aromatic carbon atom. Preferred aryls include, for example, phenyl, naphthyl, and the like.

"Alkyl" refers to, for example, straight chain and branched alkyl groups having from 1 to 20 carbon atoms, or from 1 to 15 carbon atoms, or from 1 to 10, or from 1 to 5, or from 1 to 3 carbon atoms. This term is exemplified by groups such as, for example, methyl, ethyl, n-propyl, iso-propyl, n-butyl, t-butyl, n-pentyl, ethylhexyl, dodecyl, isopentyl, and the like.

"Substituted" groups refer to, for example, a group having from 1 to 3, and preferably 1 to 2, substituents selected from the group consisting of alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Alkoxy" refers to, for example, the group "alkyl-O—" which includes, by way of example, methoxy, ethoxy, n-propyloxy, iso-propyloxy, n-butyloxy, t-butyloxy, n-pentyloxy, 1-ethylhex-1-yloxy, dodecyloxy, isopentyloxy, and the like. Another example of alkoxy is alkoxyalkoxy or alkoxyalkoxyalkoxy, and the like.

"Substituted alkoxy" refers to, for example, the group "substituted alkyl-O—."

"Alkenyl" refers to, for example, alkenyl group preferably having from 2 to 6 carbon atoms and more preferably 2 to 4 carbon atoms and having at least 1 and preferably from 1-2 sites of alkenyl unsaturation. Such groups are exemplified by vinyl, allyl, but-3-en-1-yl, and the like.

"Substituted alkenyl" refers to, for example, alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic with the proviso that any hydroxyl substitution is not attached to a vinyl (unsaturated) carbon atom.

"Aryloxy" refers to, for example, the group aryl-O— that includes, by way of example, phenoxy, naphthoxy, and the like.

"Alkynyl" refers to, for example, an alkynyl group preferably having from 2 to 6 carbon atoms and more preferably 2 to 3 carbon atoms and having at least 1 and preferably from 1-2 sites of alkynyl unsaturation.

"Substituted alkynyl" refers to, for example, an alkynyl group having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Aryloxy" can be for example the group aryl-O— that includes, by way of example, phenoxy, naphthoxy, and the like.

"Substituted aryloxy" can be, for example, substituted aryl-O— groups.

"Alkylene oxide" or "alkyleneoxy" or "polyether" can be, for example, the group —O($R^a$—O)$_n$—$R^b$ where $R^a$ is alkylene and $R^b$ is alkyl or optionally substituted aryl and n is, for example, an integer from 1 to 6, or from 1 to 3. Alkylene oxide can be, for example, based on such groups as ethylene oxides or propylene oxides. Alkylene oxide can, for example, include a variety of alkylene segments in the same chain, for example:

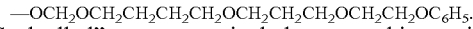

—OCH$_2$OCH$_2$CH$_2$CH$_2$CH$_2$OCH$_2$CH$_2$CH$_2$OCH$_2$CH$_2$OC$_6$H$_5$.

"Cycloalkyl" groups can include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments, the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Substituted cycloalkyl groups may be substituted one or more times with non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

"Heterocyclyl" (or heterocyclic) groups can include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups." Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2, 3-, 4-, 5-, or 6-substituted, or disubstituted with various substituents such as those listed above.

"Heteroaryl" groups can be aromatic ring compounds containing 5 or more ring members, of which one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl(pyrrolopyridinyl), indazolyl, benzimidazolyl, imidazopyridinyl(azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

"Salt" can be for example derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

"Conjugated polymer" refers to, for example, polymers comprising at least some conjugated unsaturation in the backbone.

"A polythiophene" or "polythiophene" refers to, for example, polymers comprising a thiophene in the backbone including polythiophene, derivatives thereof, and copolymers and terpolymers thereof.

"Regioregular polythiophene" refers to, for example, polythiophene having high levels of regioregularity including for example at least 80%, or at least 90%, or at least 95%, or at least 98%, or at least 99%.

Solubilizing groups are known in the art which can be used as side groups in polymers and copolymers, wherein the polymer or copolymer is relatively difficult to dissolve because of the backbone. For example, if the backbone is very rigid, a flexible side group can help facilitate solubility. One skilled in the art can determine the type and amount of solubilizing groups which facilitate solubility. Hydrogen is not usually a solubilizing group.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to—substituted aryl-(substituted aryl)-substituted aryl.

Similarly, it is understood that the above descriptions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

Part I

Polymers and Copolymers (Co-)Polymers Comprising Planarized Bithiophene Repeat Units Copolymers and homopolymers are known in the art. They can be used in such electronic devices as photovoltaic cells. See, for example, US Patent Publication 2008/0121281 published May 29, 2008. Copolymers and homopolymers comprise repeat groups and end groups. The degree of polymerization n is not particularly limited but can be for example 2 to 500,000 or 5 to 100,000 or 10 to 10,000, or 10 to 1,000, or 10 to 100. In many cases, molecular weight is suitable to allow for solubility.

Of particular interest are copolymers and homopolymers that comprise planarized bithiophene repeat units. Such repeat units may comprise two thiophene rings connected by a bridging segment. Such bridging segments may comprise benzo, naphtho, or quinoxalino segments.

Examples of planarized bithiophene repeat units may be represented by the structure (II):

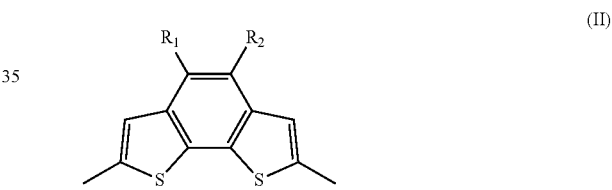

where $R_1$ and $R_2$ are solubilizing groups. The presence of such solubilizing groups can enhance copolymer or homopolymer solubility. Such groups can be, for example, any group which is compatible with the synthesis of planarized bithiophene units and compatible with subsequent polymerization and copolymerization steps. (In this and the following formulae, the bonds attached to the periphery of the structure represent linkages to adjoining repeat groups or end groups.) Protective groups can be used as appropriate. Solubilizing groups may enhance resistance to oxidation. $R_1$ and $R_2$ may be the same group or may be different groups. $R_1$ and $R_2$ may also represent a single moiety twice attached to the phenyl ring, exemplified by these structures:

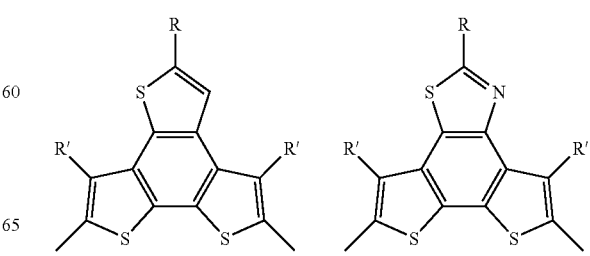

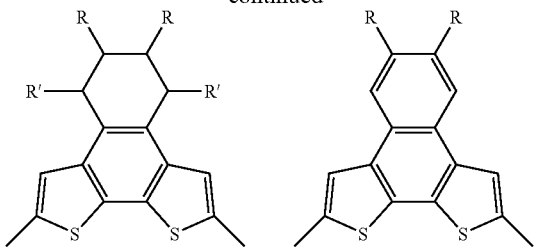

where R and R' are chosen independently in the same manner as for $R_1$ or $R_2$, generally.

$R_1$ and $R_2$ can be, for example, independently alkyl groups including linear or branched alkyl groups including, for example, hexyl, octyl, decyl, octadecyl, t-butyl, 2-ethylhexyl, and p-hexylphenyl. The carbon range for $R_1$ and $R_2$ can be, for example, C5-C18, or C6-C15. The group $R_1$ or $R_2$ can have a chiral center if desired.

In a preferred embodiment, either or both of groups $R_1$ and $R_2$ can comprise branched alkyl groups including, for example, ethylhexyl. The groups optionally may be substituted. Branched alkyl groups, both substituted and unsubstituted, are known in the art. See, for example, US Patent Publication 2008/0315751 published Dec. 25, 2008 by Sheina et al., which is hereby incorporated by reference in its entirety. An example is the structure:

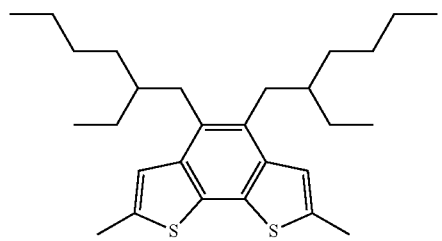 [SMILES: CCCCC(CC)Cc1c(CC(CC)CCCC)c2cc(C)sc2c2sc(C)cc12]

These groups $R_1$ and $R_2$ can be, for example, optionally substituted hydrocarbon moieties. In some cases, one can introduce one or more heteroatoms, such as oxygen, into the $R_1$ and $R_2$ groups. Examples include hexyl, octyl, decyl, octadecyl, t-butyl, 2-ethylhexyl, p-hexylphenyl, n-butoxy, t-butoxy, sec-butoxy, n-pentoxy, and the like. Examples can comprise mixed aryl and alkyl substituents. Examples can include C6-C24 moieties. Other examples for $R_1$ and $R_2$ include C1-C20 alkyl, C1-C20 alkoxy, aryl, heteroaryl, C3-C20 cycloalkyl, and C3-C20 heterocycloalkyl.

More particularly, $R_1$ and $R_2$ can be, for example, an optionally substituted alkyl, an optionally substituted aryl, an optionally substituted alkenyl, an optionally substituted alkynyl, and the like. In some cases, $R_1$ or $R_2$ can be hydrogen.

In a preferred embodiment, either or both of $R_1$ and $R_2$ can comprise alkyleneoxy groups including, for example, n-octyloxy. Such an embodiment is exemplified by the structure:

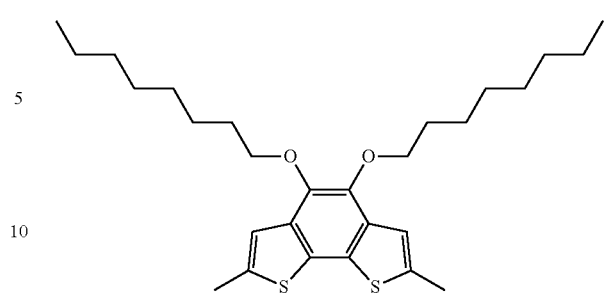

In another embodiment, the planarized bithiophene repeat unit can be represented by one of the structures:

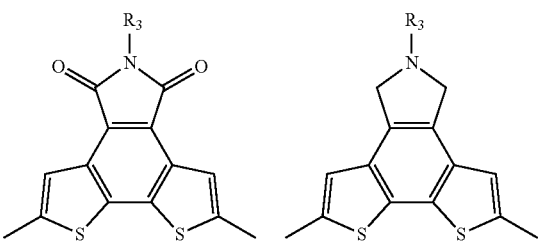

wherein $R_3$ is a solubilizing group that can be chosen as described for $R_1$ and $R_2$, above.

In some embodiments, the formula V(a) can function as an acceptor moiety in a donor acceptor polymer structure.

The copolymer can comprise at least one planarized bithiophene unit, or can comprise a plurality of planarized bithiophene units, different from each other, such as, for example, at least two different planarized bithiophene units.

The copolymer can also comprise repeat units that are not planarized bithiophene units, as described further below.

In one embodiment, the copolymer comprises only planarized bithiophene units.

In another embodiment, the copolymer comprises at least one planarized bithiophene unit and at least one repeat unit that is not a planarized bithiophene repeat unit.

In one embodiment, two different comonomers are copolymerized including at least one planarized bithiophene comonomer. The two different comonomers can comprise a dimer.

In one embodiment, the dimer can comprise one unit which functions as a donor, and a second unit which functions as an acceptor relative to the donor. For example, the planarized bithiophene moiety can be an electron donor. The other moiety can be an electron acceptor.

In the copolymer, more than one donor moiety can be present. For example, a first donor moiety can be a planarized bithiophene, and a second donor moiety can be a donor that is not a planarized bithiophene. Examples for such donors can be found in Usta et al., *J. Am. Chem. Soc.*, 2006, 128, 9034-9035, which is hereby incorporated by reference in its entirety including structures and schemes. In particular, siloles can be used including a silicon-containing moiety TS6T1. The units can be represented by:

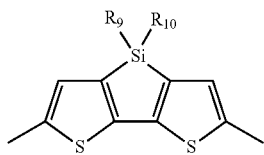

wherein $R_9$ and $R_{10}$ can be chosen independently as described for $R_1$, $R_2$, and $R_3$ above for planarized bithiophene units. For example, $R_9$ and $R_{10}$ can be an alkyl such as hexyl (or branched alkyl).

Structure A-I:

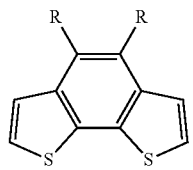

Structure A-IV:

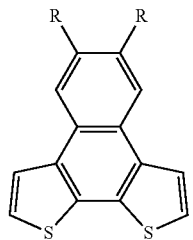

R in Structure A-I and Structure A-IV is described elsewhere herein and can be a solubilizing group, for example. Additional references below in regards to Structure A-I, in particular, further enable making and using polymers, compositions, and embodiments described herein.

1. WO 2007/105638 A1 Sep. 20, 2007 (Sumitomo Chemical company, JP in Japanese)
2. JP2007238563A (in Japanese)
3. JP2007238563A (translated)
4. Yoshida, S. et al. *J. Org. Chem.*, 1994, 59, 3077. Novel Electron Acceptors Bearing a Heteroquinonoid System. 4.'Syntheses, Properties, and Charge-Transfer Complexes of 2,7-Bis (dicyanomethylene)-2,7-dihydrobenzo[2,1-b:3,4-b']dithiophene, 2,7-Bis(dicyanometbylene)-2,7-dihydrobenzo[1,2-b:4,3-b] dithiophene, and 2,6-Bis(dicyanomethylene)-2,6-dihydrobenzo[1,2-h4,5-b]dithiophene
5. Rieger, R. et al. *Adv. Mater.* 2009, 21, 1. Rational Optimization of Benzo[2,1-b;3,4-b']dithiophene-Containing Polymers for Organic Field-Effect Transistors.
6. DE03435947 A1 (in German)
7. Watanabe, H.; Kumagai, J.; Tsurugi, H.; Satoh, T.; Miura, M. *Chem. Letters*, 2007, 36, 1336. Synthesis of alkylated benzo[2,1-b:3,4-b']dithiophenes by annulative coupling and their direct arylation under palladium catalysis.

Oligomers, Trimers, and Dimer Comprising Planarized Bithiophene, and Alternating Copolymers Also provided are oligomers such as dimers, trimers, tetramers, and the like which comprise structures such as:

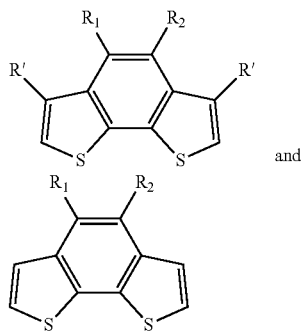

where these structures are linked into the oligomer at, for example, the 2- and 5-positions of the thiophene rings. $R_1$, $R_2$, and R' can be solubilizing groups or hydrogen. A trimer can be represented as A-B-A or B-A-B, wherein the benzo[2,1-b:3,4-b']thiophene can be A or B.

In another embodiment, a dimer can be first formed with units of two different monomers, and then an alternating copolymer can be formed from polymerization of the dimer. For example, a dimer which can be represented as -A-B— can be subjected to polymerization to form an alternating copolymer which can be represented by -[A-B]$_n$— wherein A represents at least one planarized bithiophene repeat unit and B represents a repeat unit that is not a planarized bithiophene repeat unit, or wherein A represents at least one first planarized bithiophene unit and B represents at least one second different planarized bithiophene unit. The B unit can itself be a dimer, or a trimer, or a tetramer, and the like.

In some embodiments, the dimer can be also represented as below:

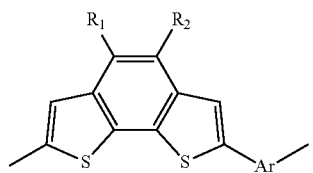

wherein Ar in this formula can be another moiety that is not a planarized bithiophene, as described further below including a moiety that comprises an aromatic unit, where $R_1$ and $R_2$ are as defined herein above.

Other Acceptor Moieties

In some embodiments, the moiety that is not a planarized bithiophene (the "other moiety") may comprise conjugated bonds and may function as an acceptor moiety. Such moieties can comprise one or more ring structures including, for example, one or more aromatic rings, heterocyclic rings, heteroaryl rings, heterocyclic rings, fused rings, thiophene rings, substituted aromatic rings, and/or substituted thiophene rings, wherein the structures include linking sites to the copolymer chain.

For example, in some embodiments, alternating donor-acceptor copolymers may be polymerized using organometallic mediated coupling reactions, sometimes referred to as Ullmann reactions. For example, each donor segment might be functionalized with two active groups (AGs), such as $Sn(R)_3$, $ZnX_2$, $MgX_2$, $MnX_2$, $B(OR)_2$, X, or silyl, where R represents an alkyl moiety and X represents a halogen or pseudohalogen moiety, and each acceptor segment functionalized with two halide or pseudohalide groups. Suitable halogen or pseudo halogen moieties may comprise I, F, Br, Cl, or triflate. Subjecting these segments to such coupling reactions as Stille, Negishi, Suzuki, or the like, results in a copolymer comprising alternating donor and acceptor segments. Such reactions are described in the following references, each of which is incorporated by reference in its entirety: *Cross-Coupling Reactions: A Practical Guide*, Ed. Miyaura, 2002; *Handbook of Organopalladium Chemistry for Organic Synthesis*, Ed. Negishi, 2002; Kuwano, R, Utsunomiya, M., Hartwig, J. F., *J. Org. Chem.*, 2002, 67, 6479-6486; Yu et al., *J. Am. Chem. Soc.*, 2009, 131, 56; Yang Yang et al., *Macromol.* 2008, 41, 6012; LeClerc et al., *J. Am. Chem. Soc.*, 2008, 130, 732; Swager et al., *Adv. Mater.*, 2001, 13, 1775; Koeckelberghs et al., *Macromol.*, 2007, 40, 4173.

Examples include any of the following; the linking bonds to adjoining repeat groups or end groups are shown for monomers VI(c), VI(d), VI(g), VI(i), and VI(i)-(o) only:

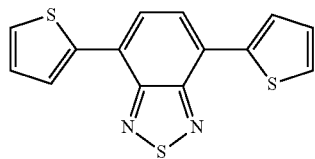

Formula VI(a)

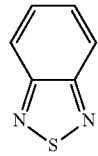

VI(b)

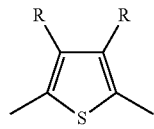

VI(c)

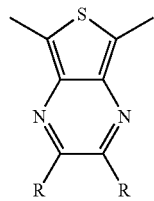

VI(d)

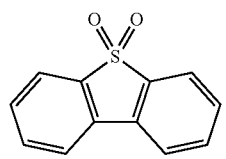

Formula VI(e)

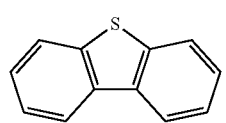

VI(f)

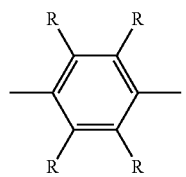

VI(g)

-continued

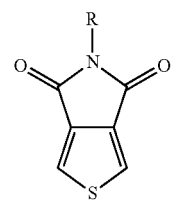

Formula VI(h)

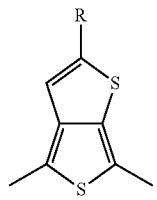

VI(i)

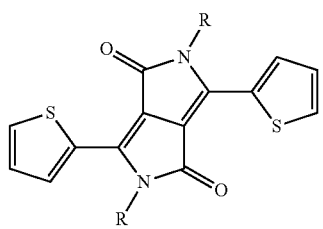

VI(j)

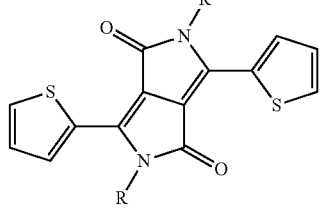

Formula VI(k)

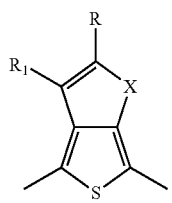

VI(l)

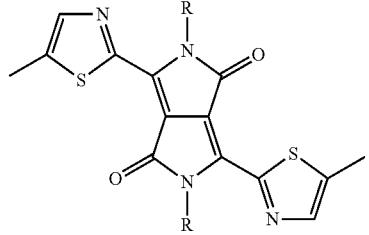

X = S, O, N, Se
R = alkyl, branched alkyl
$R_1$ = halogen (e.g., F) or H

In monomers VI(c)-(d), VI(h)-(j), and VI(l)-(o), the R groups can be independently the same structures as described above for $R_1$, $R_2$, and $R_3$. In monomer VI(g), the R groups can be one of the halogens, such as fluorine. All R groups can be fluorine. Monomers VI(a)-(f) can be further substituted as desired. In monomer VI(e), R can be, for example, a group as described above for $R_1$, $R_2$, and/or $R_3$.

Figure 4:
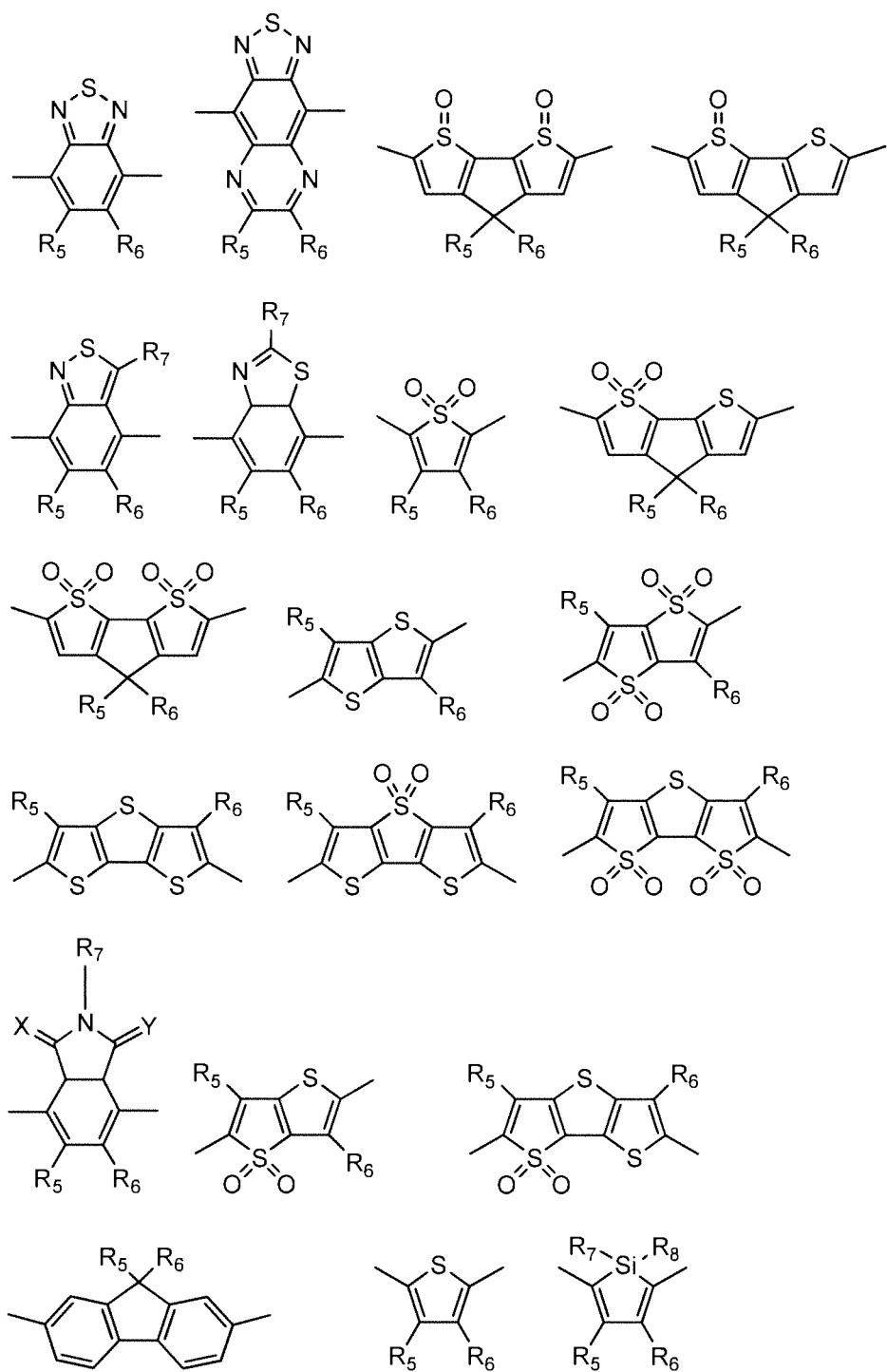
FIG. 4 illustrates examples of types of repeat units that are not planarized bithiophenes.

Other moieties are described in, for example, WO 2007/011739 (see structures XI, XII, XIII, XIV, XV, or XVI), which is hereby incorporated by reference in its entirety. See also structures in FIG. 4. The various R groups shown in FIG. 4 including $R_5$, $R_6$, $R_7$, and $R_8$ can be independently as described above for $R_1$, $R_2$, and $R_3$. X and Y can be independently $CH_2$, O, or S.

Figure 3:
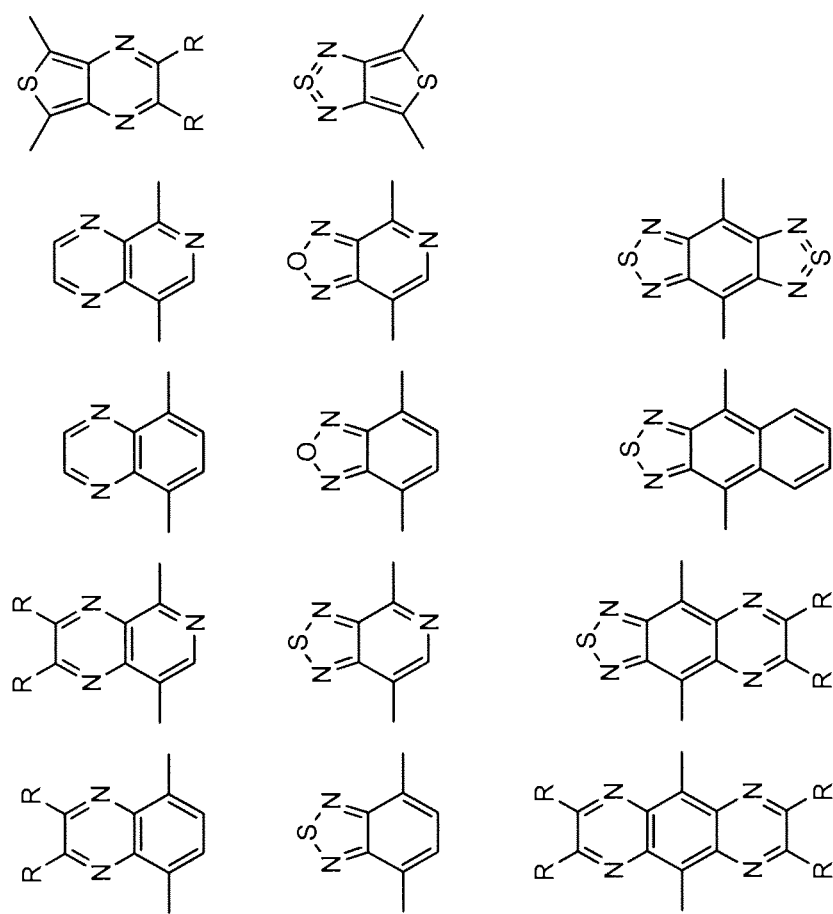
FIG. 3 illustrates examples of X groups in a T-X-T moiety, where T is thiophene.

Another example for the other moiety can be represented by T-X-T wherein T represents a heterocyclic group such as, for example, a thiophene moiety which is covalently linked to an X group, and X can be a variety of groups including, for example, one or more aromatic groups, or heterocyclic groups, or bicyclic groups. Examples of X are shown in FIG. 3. See also, for example, Blouin et al., *J. Am. Chem. Soc.*, 2008, 130, 732-742, which is hereby incorporated by reference in its entirety. In the following representation, the T unit is a thiophene, including a substituted thiophene, and the X unit is a heterocyclic or aromatic moiety. The substituted thiophene can have solubilizing substituents such as, for example, alkyl. Ar can be a moiety as shown in FIG. 3, wherein the various R groups shown in FIG. 3 can be independently as described above for $R_1$, $R_2$, and $R_3$.

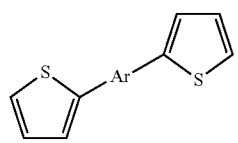

Another example can be represented as:

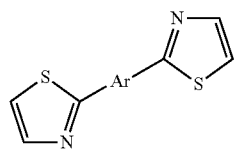

Again, Ar can be a moiety as shown in FIG. 3. Ar can be also, for example, a halogenated aromatic.

Representative structures with use of Formula VI(b), a thiadiazole, are shown below, including random and alternating copolymers:

Formula VII

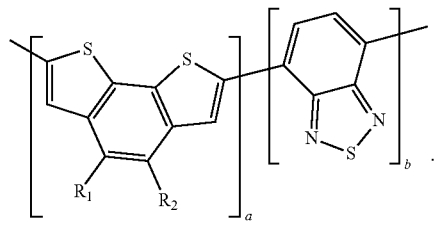

In Formula VII, "a" represents the number of repeat units for the planarized bithiophene structure, and "b" represents the number of repeat units for the other structure. The ratio of "a" and "b" can be varied by one skilled in the art.

In one embodiment, one n-type (acceptor) monomer moiety and one p-type (donor) monomer moiety can be coupled to form a dimer, which can be represented by

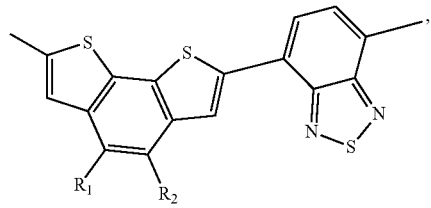

which can be copolymerized to form an alternating copolymer, which can be represented by

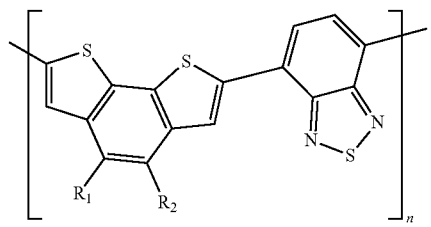

wherein n is the number of repeat units in the alternating copolymer chain.

Other monomers and polymers can be prepared using organic synthesis and polymer chemistry. See, for example, March's *Advanced Organic Chemistry, Reactions, Mechanisms, and Structure*, 6th Ed, 2007, which is incorporated by reference in its entirety. Also, synthetic strategies for preparing monomers and copolymers are described in, for example, Bundgaard et al., "Low Band Gap Polymers for Organic Photovoltaics," *Solar Energy Materials and Solar Cells*, 91 (2007), 954-985 and Koeckelberghs et al., *Macromolecules*, 2007, 40, page 4173, as well as references cited in each, are incorporated by reference in their entirety. The synthetic methods described in U.S. Pat. No. 6,369,089 and Gronowitz, S. et al., *Chem. Scripta*, 1977, 12, 57 are also incorporated by reference in their entirety.

In one embodiment, for example, a monomer bearing a planarized bithiophene moiety can be formed by the reaction scheme depicted in FIG. 1. The monomers can be adapted with linking functional groups, generating nucleophilic and electrophilic sites, for polymerization including, for example, halogen groups or tin groups.

In another embodiment, monomers can be prepared which comprise fluorinated phenylene moieties. For example, the synthesis of the oligothiophenes bearing, for example, a central tetrafluorophenylene unit and their dibromo derivatives is described in the literature (Crouch, D. J. et al., *Chem. Mater.* 2005, 17, 6567-6578). In addition, corresponding copolymers of, for example, planarized bithiophenes and oligothiophenes with incorporated fluorinated phenylene units can be prepared by Stille coupling methodology utilizing literature references cited herein and procedure below.

Examples for preparing homopolymers or copolymers by organic synthesis are known. See, for example, Blouin et al., *J. Am. Chem. Soc.*, 2008, 130, 732-742.

Polymerization and Copolymerization Reactions

Known polymerization and copolymerization methods can be used including those that form aromatic to aromatic carbon-carbon bonds including thiophene-to-thiophene bonding as known in the art. For example, a plurality of monomers can be copolymerized including, for example, at least two monomers or at least three monomers. Alternatively, one monomer moiety can be combined with another monomer moiety to form a dimer, which then can be polymerized to form an alternating copolymer.

Polymerization reactions are known in the art including, for example, electrochemical or oxidative chemical polymerization (Bolognesi, A., et al., *Synth. Met.*, 1989, 28, C521), or metal promoted cross-coupling polymerizations, e.g., Stille coupling ((a) Stille, J. K. *Angew. Chem. Int. Ed. Engl.* 1986, 25, 508. (b) Farina, V. et al. *J. Am. Chem. Soc.* 1991, 113, 9585. (b) Bao, Z. et al. *J. Am. Chem. Soc.* 1995, 117, 12426.), and Yamamoto-type polymerization (Yamamoto, T. et al. *Macromolecules* 1992, 25, 1214.).

Another example of polymerization is the Grignard Metathesis (GRIM) method, which is generally known in the art. For a more detailed description of this method, see, for example, Lowe, R. S. et al., *Adv. Mater.*, 1999, 11, page 250; Iovu, M. C. et al., *Macromolecules* 2005, 38, 8649; Yokoyama et al., *Macromolecules*, 2004, 37, page 1169, which hereby are incorporated by reference in their entirety.

Alternating donor-acceptor copolymers may be polymerized using organometallic mediated coupling reactions, sometimes referred to as Ullmann reactions. For example, each donor segment might be functionalized with two active groups (AGs), such as $Sn(R)_3$, $ZnX_2$, $MgX_2$, $MnX_2$, $B(OR)_2$, X, or silyl, where R represents an alkyl moiety and X represents a halogen or pseudohalogen moiety, and each acceptor segment functionalized with two halide or pseudohalide groups. Suitable halogen or pseudo halogen moieties may comprise I, F, Br, Cl, or triflate. Subjecting these segments to such coupling reactions as Stille, Negishi, Suzuki, or the like, results in a copolymer comprising alternating donor and acceptor segments. Such reactions are described in the following references, each of which is incorporated by reference in its entirety: *Cross-Coupling Reactions: A Practical Guide*, Ed. Miyaura, 2002; *Handbook of Organopalladium Chemistry for Organic Synthesis*, Ed. Negishi, 2002; Kuwano, R, Utsunomiya, M., Hartwig, J. F., *J. Org. Chem.*, 2002, 67, 6479-6486; Yu et al., *J. Am. Chem. Soc.*, 2009, 131, 56; Yang Yang et al., *Macromol.* 2008, 41, 6012; LeClerc et al., *J. Am. Chem. Soc.*, 2008, 130, 732; Swager et al., *Adv. Mater.*, 2001, 13, 1775; Koeckelberghs et al., *Macromol.*, 2007, 40, 4173.

Figure 2:
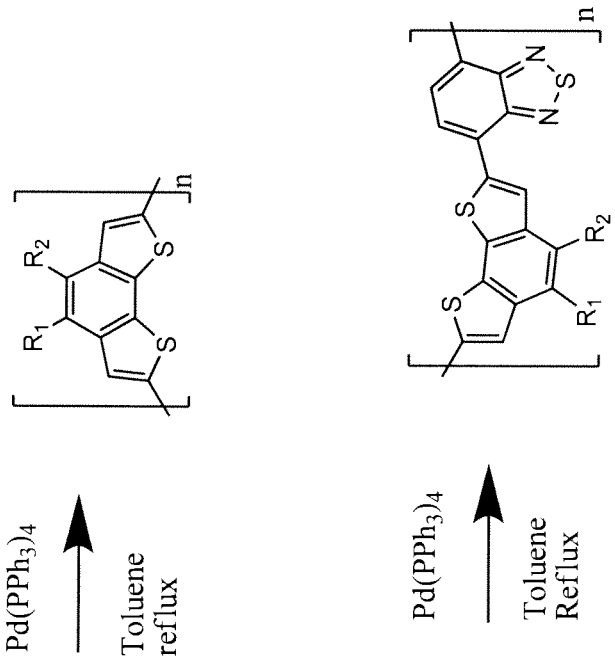
FIG. 2 illustrates homopolymerization and copolymerization using organometallic mediated coupling reactions.

FIG. 2 illustrates additional examples of polymerization and copolymerization embodiments including use of Stille coupling. For a more detailed description of such copolymerization methods, see, for example, Liu, J. et al., *J. Am. Chem. Soc.*, 2008, 130, page 13167, which hereby is incorporated by reference in its entirety.

Properties

One important property is resistance to oxidation in the air. For example, resistance to oxidation in air can be measured spectroscopically or electrochemically, and resistance can extend over, for example, at least 24 hours, or at least 48 hours, or at least one week, or at least one month. Ambient air can be used in which normal oxygen content is present in the air. Ambient room temperature can be used. If desired, more acute testing conditions can be used such as, for example, elevated temperatures or elevated oxygen contents.

Another important property is device efficiency. For example, power conversion efficiency of a solar cell can be determined as $\eta=(FF \cdot Jsc \cdot Voc)/Pin$, where FF is the fill factor, Jsc is the current density at short circuit, Voc is the photovoltage at open circuit, and Pin is the incident light power density. Methods known in the art can be used to measure OPV parameters. $\eta$ (%) values can be for example at least about 1%, or at least about 2%, or at least about 3%, or at least about 4%, or at least about 5%, or at least about 6%, or at least about 7%, including for example about 1% to about 8%, or about 1% to about 7%, or about 1% to about 6%, or about 1% to about 5%, or about 1% to about 3.4%, or about 2% to about 3.4%.

Combinations of properties can be also important such as, for example, good resistance to oxidation in air combined with, for example, good processability and/or low band gap, as well as other properties noted herein with respect to advantages and performance. The combination of good resistance to oxidation in air with high power conversion efficiency can be important for solar cell applications.

Applications

The polymers and copolymers described herein can be used in organic electronic devices including, for example, OLEDs, OPVs including as OPV active layer, transistors, OFETs, batteries, and printed electronics generally, as well as sensors.

Printed Electronics are generally known in the art. See, for example, *Printed Organic and Molecular Electronics*, Ed. D. Gamota et al., 2004. For example, Chapters 1 and 2 describe organic semiconductors, Chapter 3 describes manufacturing platforms for printing circuits, Chapter 4 describes electrical behavior of transistors and circuits, Chapter 5 describes applications, and Chapter 6 describes molecular electronics. See also Pope et al., *Electronic Processes in Organic Crystals and Polymers*, 1999.

Photovoltaic cells are known in the art. See, for example, Sun and Sariciftci, *Organic Photovoltaics, Mechanisms, Materials, and Devices*, 2005. See, also, for example, US Patent Publication 2008/0315751 published Dec. 25, 2008 to Sheina et al. The photovoltaic cell can comprise an active layer comprising a composition comprising at least one p-type material and at least one n-type material. One can engineer HOMO, LUMO, and band gaps for the p- and n-type materials for good performance. The morphology of the active layer can be adapted to provide good performance. For example, a nanoscale morphology can be prepared. An example is a bulk heterojunction.

In an OPV active layer, the polymers described herein, which can be p-type materials, can be combined with n-type materials or acceptor moieties, such as, for example, fullerenes and fullerene derivatives. An example of a fullerene derivative is PCBM. Fullerenes can be also derivatized with a moiety such as indene or substituted indene. One fullerene core can be derivatized with, for example, one, two, or three indene groups. Other types of n-type materials known in the art can be used. If desired, larger area photovoltaics can be fabricated. See, for example, Bundgaard et al., *Solar Energy Materials and Solar Cells*, 2007, 91, 1019-1025.

One reference teaches employing substituted thiophenes as comonomers which has resulted in improvements in such properties as solubility and molecular weight. See Liu et al., *J. Am. Chem. Soc.*, 2008, 130, 13167-13176. Measurement of resistance to oxidation can be an important embodiment. For example, one method of measuring instability towards oxidation is through the use of UV-visible absorption spectrophotometric methods, where progressive oxidation can result in the development of new absorption peaks and either the bathochromic/hypsochromic or hyperchromic/hypochromic (e.g., right/left, also referred as to red/blue or up/down, respectively) shifting of the spectrum. See, for example, Ogawa et al., *Macromolecules*, 2006, 39, 1771-1778. Embodiments which provide improved resistance to oxidation are in many cases preferred.

Six additional embodiments are provided:

Embodiment #1

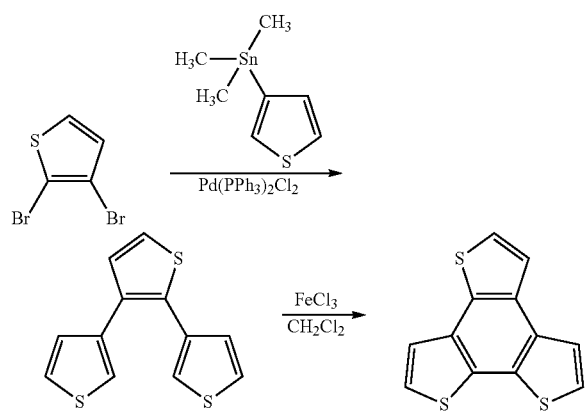

This product is functionalized to produce a monomer, which is subsequently incorporated into a homopolymer or copolymer by organometallic mediated coupling reactions.

Embodiment #2

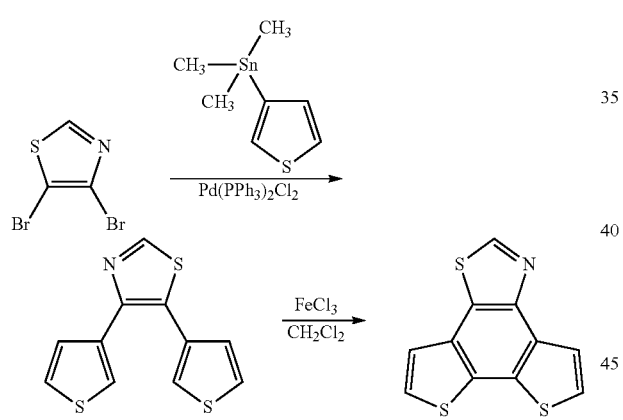

This product is functionalized to produce a monomer, which is subsequently incorporated into a homopolymer or copolymer by organometallic mediated coupling reactions.

Embodiment #3

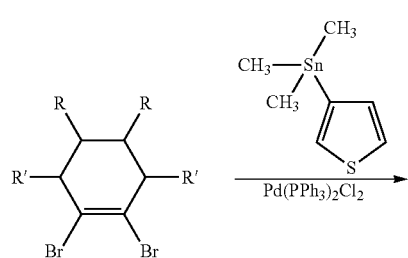

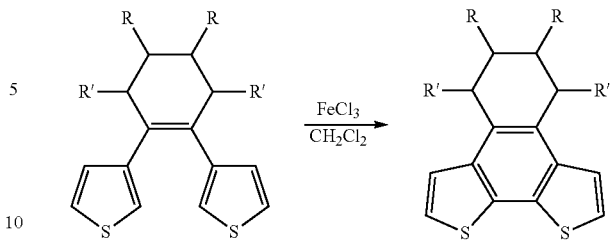

This product is functionalized to produce a monomer, which is subsequently incorporated into a homopolymer or copolymer by organometallic mediated coupling reactions.

Embodiment #4

Product prepared according to Xiao, S., et al., *Macromolecules*, 2008, 41(15), 5688-5696, which is incorporated by reference in its entirety:

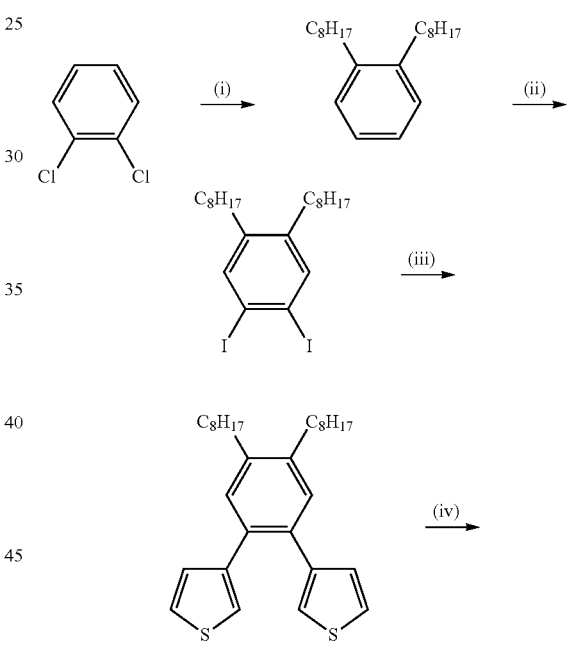

Notes: (i) octylmagnesium bromide, 1,3-bis(diphenylphosphinopropane)nickel(II) chloride, anhydrous ethyl ether; (ii) $I_2$, $NaIO_3$, $HOAc$—$H_2SO_4$—$H_2O$, reflux; (iii) 3-thiopheneboronic acid, $Pd(PPh_3)_4$, $Na_2CO_3$, toluene, EtOH and $H_2O$, reflux; (iv) $I_2$, $O_2$, under irradiation of 400 W mercury lamp.

This product is functionalized to produce a monomer, which is subsequently incorporated into a homopolymer or copolymer by organometallic mediated coupling reactions.

Embodiment #5

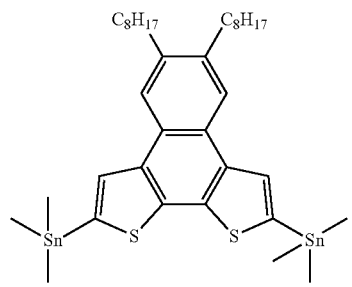

+

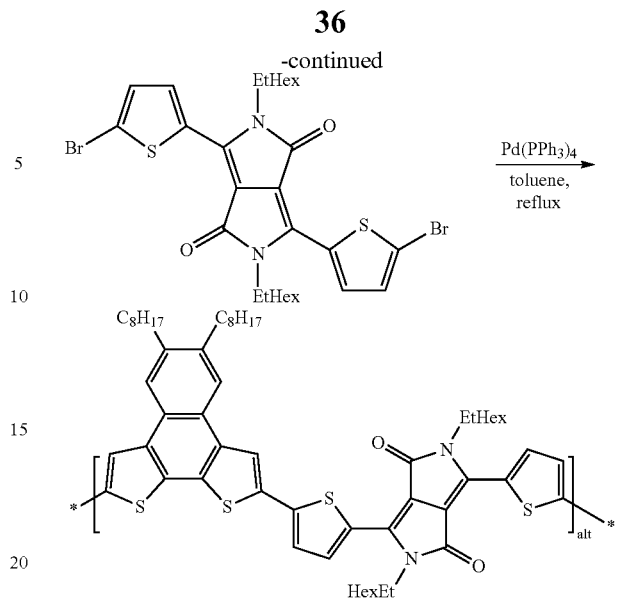

-continued

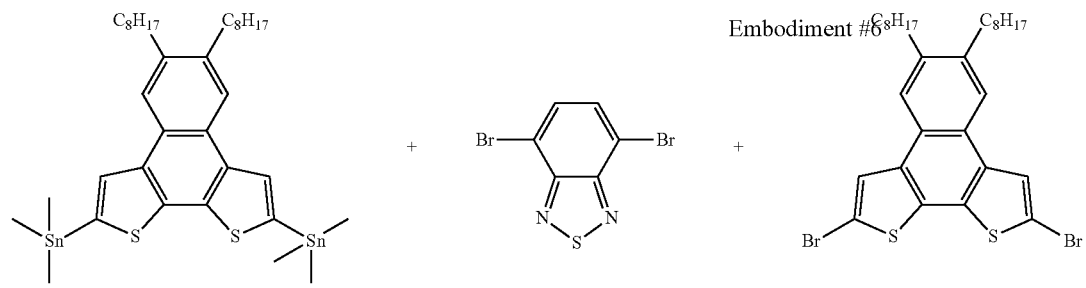

Embodiment #6

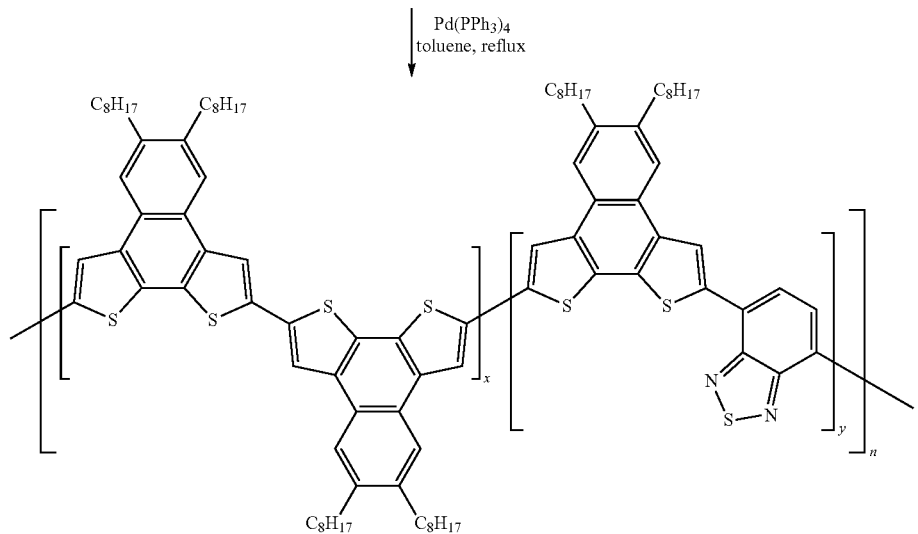

Additional Aspects and Embodiments

Methods of Making Monomer, Benzo[2,1-b-3,4-b'] Dithiophene

Additional embodiments are provided with respect to making low molecular weight organic compounds and polymerization monomers.

Figure 5:
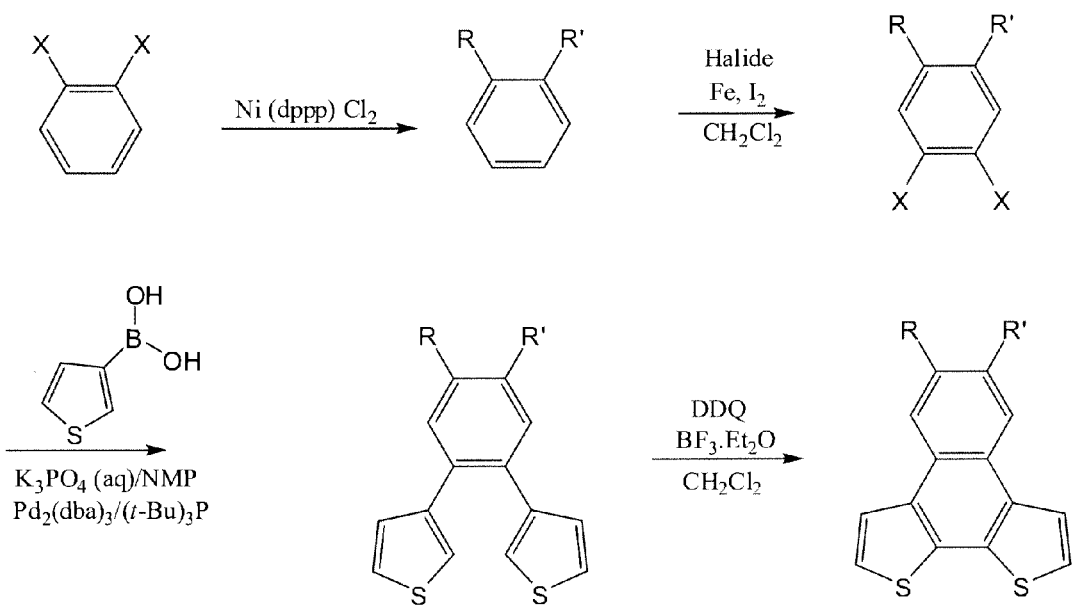
FIG. 5 illustrates synthesis of naphtha dithiophene repeat units.

In one embodiment, for example, a monomer bearing a benzo[2,1-b:3,4-b']dithiophene moiety can be formed by the reaction scheme depicted in FIG. 5. The monomers can be generally synthesized starting from simple aryl compounds, linking them with solublizing groups, halogenating them, followed by Suzuki coupling with sulfur containing hereterocycles and conducting oxidative cyclization to yield the benzo[2,1-b:3,4-b']dithiophene moiety.

One embodiment provides a method comprising: providing at least one compound comprising at least one first thiophene ring which comprises a substituent at the 3 position, wherein the substituent comprises a C2 linkage group which links the first thiophene ring to a second thiophene ring at the 4 position of the second thiophene ring, and reacting the compound so that ring closure occurs to form a benzo[2,1-b:3,4-b']dithiophene moiety, wherein the reacting step is carried out in the presence of a lewis or Bronsted acid and an oxidant.

For example, one embodiment provides a method comprising cyclizing a compound of formula IV,

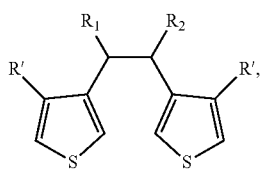

(IV)

in the presence of a Lewis or Bronsted acid and an oxidant to produce the compound of formula I,

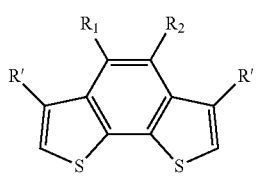

(V)

wherein $R_1$ and $R_2$ each comprise, for example, one or more optionally substituted alkyl, optionally substituted alkoxy, optionally substituted aryl, optionally substituted heteroaryl, optionally substituted cycloalkyl and optionally substituted heterocyclyl group, or can form a ring including a benzene ring or a heterocyclic ring. R' can be hydrogen or a solubilizing group, for example.

In one embodiment the compound of formula IV has the formula IVA

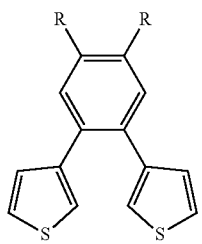

(IVA)

and the compound of formula V has the formula VA,

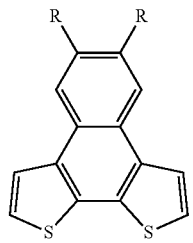

(VA)

wherein R are solubilizing groups.

R can be, for example, any suitable solubilizing group as described herein. In one embodiment, each R comprises a linear or branched alkyl group. Preferred branched alkyl groups for R, include branched alkyl groups having four or more carbon atoms. For example, the branched alkyl group may be a $C_3$-$C_{20}$ alkyl group, a $C_4$-$C_{12}$ alkyl group, or a $C_5$-$C_{10}$ alkyl group. Examples of branched alkyl groups include, but are not limited to, for example ethylhexyl groups, isopropyl, iso-butyl, sec-butyl, tert-butyl, neopentyl, or isopentyl. In an illustrative embodiment, each R comprises an ethyl hexyl group.

A combination of Lewis or Bronsted acid and an oxidant may be employed for the ring closure or cyclization step. In one embodiment, the lewis acid is selected from the group consisting of $BF_3$, $BF_3.(C_2H_5)_2O$, $BCl_3$, $AlCl_3$, $Al(CH_3)_3$, $TiCl_4$, $ZrCl_4$, $SnCl_4$, $SnCl_4.5H_2O$, $SnF_4$, $VCl_4$, $SbF_5$, $ScCl_3$, $ScCl_3.6H_2O$, $Sc(CF_3SO_3)_3$, $La(CH_3CO_2).xH_2O$, $LaCl_3$, $LaCl_3.7H_2O$, $LaF_3$, $La(NO_3)_3.6H_2O$, $La(C_2O_4)_3.xH_2O$, $La(SO_4)_3.xH_2O$, $La(CF_3SO_3)_3$, $ZnCl_2$, $ZnCr_2$, $ZnF_2$, $Zn(CH_3CO_2)_2$, $Zn(CH_3CO_2)_2$, $Zn(CH_3CO_2)_2.2H_2O$, $ZnSiF_6.xH_2O$, $Zn(NO_3)_2.xH_2O$, $Zn(C_2O_4)_2.xH_2O$, and $Nd(CF_3SO_3)_3$. In some embodiments, the oxidant is a quinone oxidant. In some embodiments, the quinone oxidant is selected from the group consisting of 2,3-dichloro-5,6-dicyanobenzoquinone, 1,4-benzoquinone, 1,2-benzoquinone, o-tetrafluorobenzoquinone, p-tetrafluorobenzoquinone, tetracyanobenzoquinone, o-chloranil, p-chloronil, 1,4-naphthoquinone, anthraquinone, 2,6-diphenylbenzoquinone, and 2,6-di-tertbutylbenzoquinone. In an illustrative embodiment, a combination of $BF_3$ $Et_2O$ and DDQ is employed for the ring closure step. Other oxidants are described in, for example, U.S. Pat. No. 7,368,624.

The ring closure reaction may be effectively conducted in dry and inert conditions optionally using dry solvents. Thus, in one embodiment may be conducted in a suitable solvent selected from the group consisting of dichloromethane, dichloroethane, acetonitrile, toluene, and/or propionitrile. In an illustrative embodiment, the solvent is dry dichloromethane. The ring closure reaction proceeds efficiently when it is conducted in absence of free halogen impurities.

The present method for oxidative cyclization can be easier to control and can lead to products of higher purity. It does not require large excess of the oxidant or the lewis acid and therefore makes the isolation of cyclized product as well as recycling of the reagents easier. Use of a Bronsted acid instead of lewis acid may lead to many side products likely via carbocation chemistry. Methods using ferric chloride and palladium acetate for ring closure are known to produce impure products and therefore should be avoided. Thus, in one embodiment, the cyclization step should substantially exclude reagents such as e.g., ferric chloride and palladium acetate.

Compounds of formula IV, used for the ring closure reaction, may be produced by coupling a halogenated compound of formula X with thiophene-3yl-boronic acid in presence of a metal catalyst and a phosphine compound, wherein the compound of formula X has the following structure:

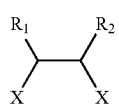

(X)

and further wherein $R_1$ and $R_2$ independently or together comprise one or more optionally substituted alkyl, optionally substituted alkoxy, optionally substituted aryl, optionally substituted heteroaryl, optionally substituted cycloalkyl and optionally substituted heterocyclyl group, or form a ring such as benzene or heterocyclic ring; and X is a halogen.

Suitable metal catalysts used for the coupling reaction include palladium-based catalyst selected from a group consisting of tris(dibenzylideneacetone)dipalladium and tetrakis triphenylphosphine palladium ($Pd(PPh_3)_4$). In an illustrative embodiment, tris(dibenzylideneacetone)dipalladium and tri-tertbutylphosphine are employed as catalysts for the coupling reaction.

One embodiment provides the monomer product obtained by the present methods. In one embodiment, the product comprises a benzo[2,1-b:3,4-b']dithiophene moiety.

Other embodiments provide methods for further functionalizing the monomers obtained using present methods. Still other embodiments provide methods for polymerizing these monomers or copolymers. The monomers can be adapted with linking functional groups, generating nucleophilic and electrophilic sites, for polymerization including, for example, halogen groups or tin groups.

One embodiment provides a method comprising: providing the monomer product comprising benzo[2,1-b:3,4-b']dithiophene moiety, and halogenating said product to form a dihalogenated monomer. One embodiment provides a product comprising the dihalogenated monomer produced according to the present methods. In various embodiments, the dihalogenated monomer can be dichlorinated, dibrominated, diiodinated, or ditriflated. In an illustrative embodiment, the dihalogenated monomer is dibrominated.

One embodiment provides a method comprising: providing the functionalized monomer or halogenated monomer using present methods and subjecting the functionalized to an organometallic mediated coupling reaction to form a homopolymer or a copolymer. Still other embodiments provide for homopolymers or copolymers produced by such methods.

One embodiment provides a composition comprising at least one copolymer comprising at least one first benzo[2,1-b:3,4-b']dithiophene repeat unit provided by the present methods. Electronic devices incorporating the polymers and compositions are also provided. Such devices include, but are not limited to, organic photovoltaic cells, organic light-emitting devices, and organic thin film transistors. In some embodiments, the photovoltaic cell comprises an active layer. In some embodiments the active layer of the photovoltaic cell may comprise the present compositions and polymers. One embodiment provides an ink comprising the present polymers and compositions.

Embodiments from 61/240,137 and 61/307,387

U.S. provisional application 61/240,137 filed Sep. 4, 2009 and 61/307,387 filed Feb. 23, 2010 describes additional embodiments which are incorporated by reference herein. These embodiments can be adapted to include benzo[2,1-b:3,4-b']dithiophene moieties.

For example, polymers can be prepared which comprise a backbone moiety represented by (XI):

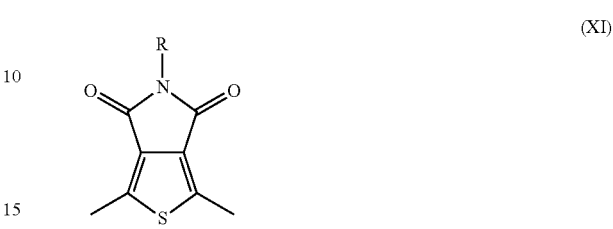

(XI)

This moiety can function as an acceptor in the donor acceptor copolymer.

In (XI), the lines at the 2- and 5-position of the thiophene ring show where the attachment occurs to another moiety such as a polymer chain or a reactive group for polymerization or coupling.

An important aspect of polymers which comprise (XI) is that they are sufficiently soluble so that inks can be formed and solution processing can be achieved. Solubility can be examined in organic or aqueous solvents. One skilled in the art can adapt the R group and other parts of the polymer chain and side groups, as well as molecular weight and/or polydispersity, to generate sufficient solubility. Organic solvents can be, for example, halogenated and non-halogenated solvents. The solvent can be a single solvent or a mixture of solvents. An example of halogenated solvent in ortho-dichlorobenzene, and this solvent can be used to measure solubility. Solubility can be measured at 25° C. Solubility can be, for example, at least 1 mg/ml, or at least 20 mg/ml. In some embodiments, solubility can be adapted to provide good bulk heterojunction (BHJ) layer morphology. For example, in some embodiments, if the solubility is high when molecular weight is too low, BHJ formation could be compromised. Higher molecular weight may be preferred to modulate solubility, and molecular weight can be used with other formulation strategies including additives to modulate solubility. In addition, polymers can be both soluble and also functionally dispersible in a solvent so that solution processing can be achieved, whether or not a true solution is formed.

The R group can be adapted to facilitate or provide solubility. The R group can also be adapted to provide desired electronic properties. The R group can be also adapted to provide steric and molecular stacking properties.

The atom in the R group bonding to the polymer chain can be, for example, carbon.

For example, the R group can be optionally substituted alkyl, optionally substituted linear alkyl, optionally substituted branched alkyl, optionally substituted aryl, optionally substituted alkylaryl, optionally substituted arylalkyl, optionally substituted alkoxy, or optionally substituted aryloxy. The R group can have, for example, 3-30 carbons, or 4-25 carbons, or 5-15 carbons. Examples include butyl, octyl and dodecyl, as well as ethylhexyl. Different R groups can be used in the same polymer as needed. The R group can be chiral. The R group can be functionalized or substituted as desired. Examples of substituents include amino, carboxylic acid, ester, halogen (including fluoro and chloro), pseudohalogen (e.g., cyano), and other functional groups known in the art.

The R group can comprise a heteroatom such as oxygen or nitrogen in the carbon chain (e.g., ether or amino linkages, respectively). The R group can comprise C1-C20 alkoxy, or C1-C20 alkyleneoxy, for example. The R group can be an oligoether such as, for example, alkoxyalkoxy or alkoxyalkoxyalkoxy, such as, for example, methoxyethoxyethoxy.

The polymer comprising structure XI can be free of protecting groups, and in particular the R group can be free of protecting groups.

The R group can be adapted to modulate or tune the LUMO, including provide a decreasing or increasing LUMO, or provide better solid state packing, or provide improved charge transport, and/or provide environmental stability. For example, the R group can be halogenated including comprise a group comprising chlorine or fluorine. The R group can be, for example, perfluorinated. The R group can be, for example, a perfluoroalkyl group such as, for example, —$C_3F_7$. The R group can be, for example, a perfluoroarylgroup such as, for example, —$C_6F_5$. For use of halogenated substituent groups to modulate LUMO and solid state packing, see, for example, Schmidt et al., *J. Am. Chem. Soc.*, 2009, 131, 6215-6228.

The R group in one or more polymers can be varied, and different R groups can be used such as, for example, R1, R2, R3, or R', R", R'", and the like, wherein all are examples of R. For example, a single polymer can be prepared which comprises R1 and R2, wherein each of these are R. For example, a monomer with R1 can be copolymerized with a monomer comprising R2. Alternatively, a polymer comprising R1 can be blended with a polymer comprising R2. The R groups can be the same or different.

Oligomeric and polymeric structures comprising (XI) are known in the art. See, for example, Nielsen et al., *Organic Letters*, 2004, 6, 19, 3381-3384 (describing dioxopyrrolo-functionalized polythiophene); Zhang et al., *J. Am. Chem. Soc.*, 120, 22, Jun. 10, 1998 (structures 12 and 21); Zhang et al., *J. Am. Chem. Soc.*, 1997, 119, 5065-5066.

Other references, including theoretical considerations, include Li et al., *Polymeric Materials Science and Engineering (PMSE) Preprints*, 2007, 96, 757-758; Pomerantz et al., *Synthetic Metals*, 2003, 135-136, 257-258; Pomerantz et al., *Tetrahedron Letters*, 2003, 44(8), 1563-1565; and Pomerantz et al., *Tetrahedron Letters*, 40, 1999, 3317-3320.

Polymer comprising (I) can be a random copolymer or a regular alternating copolymer.

Polymer can comprise multiple repeat moieties.

Moieties in the polymer chain can provide for carbon-carbon bonding with conjugation, or in addition, can provide hole transport.

Polymer side groups can provide electron withdrawing or electron accepting character, and the strength of this can be varied, e.g, weak or strong, or from weak to strong. Push-pull electronic effects can be produced.

Polymer side groups can be protected or deprotected. For example, butyloxycarbonyl (BOC) can be used to protect amino side groups. However, an embodiment comprises the polymer being totally free of protecting groups.

Block copolymers can be prepared. Either all blocks can be embodiments as described herein, or only a subset of block(s) can be embodiments described herein. For example, a block copolymer could comprise both a conjugated polymer block and a non-conjugated polymer block, or both a donor-acceptor block, and a non-donor-acceptor block.

In one embodiment, the polymer comprises a molecular weight Mn of at least 6,000 g/mol, or of at least 7,500 g/mol, or at least 10,000. In another embodiment, the polymer comprises a molecular weight Mn of at least 20,000, or at least 30,000, or at least 40,000, or at least 50,000.

Additional embodiments include, for example, polymers represented by the following structures, XI-A, XI-B, and XI-C:

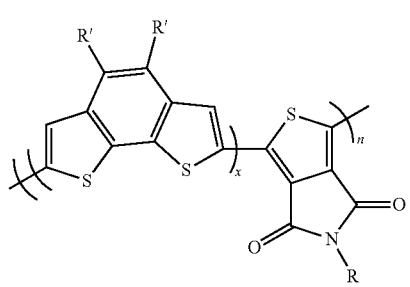

(XI-A)

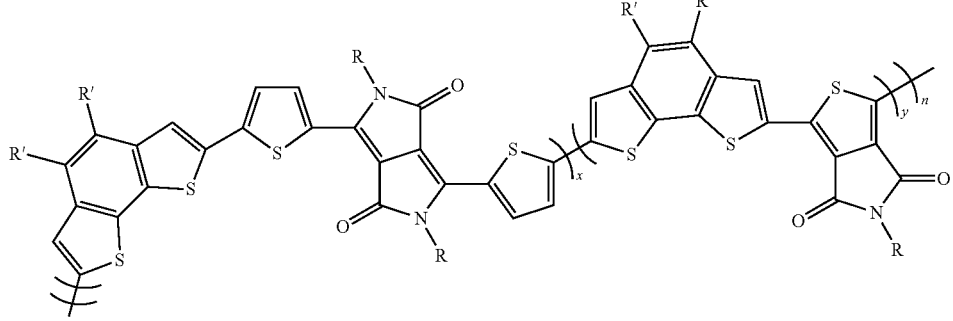

(XI-B)

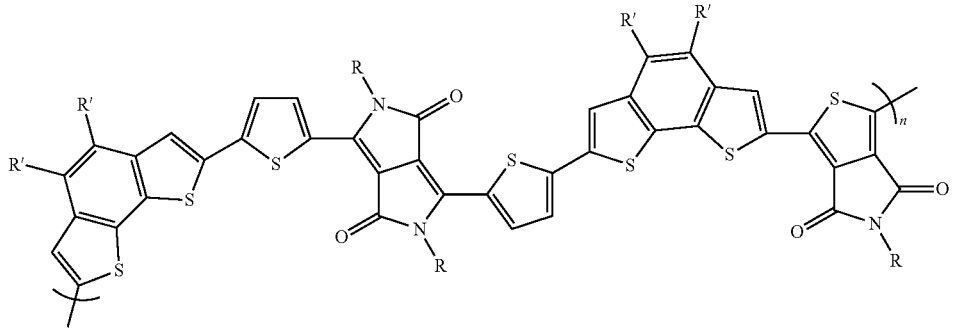

(XI-C)

Wherein R and R' are groups which can be adapted to improve solubility for the polymer as described hereinabove.

In addition, the following chart shows different, exemplary embodiments for copolymer architecture with different donors, D1 and D2 donors, and different acceptors, A1 and A2 acceptors. The polymers can comprise benzo[2,1-b:3,4-b'] dithiophene repeat units. The Chart I shows examples which are different from the -[D-A]-alternating formula seen in the prior art.

Chart I

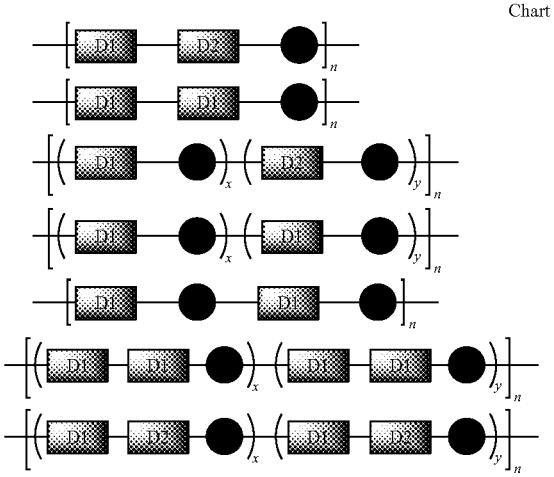

The acceptors, A1, A2, or both can comprise structure I in 61/240,137, and can also comprise any of the acceptors listed in FIG. 2 of 61/240,137 and/or described herein.

The donors can be selected from those listed in FIG. 1 of 61/240,137, for example.

The structures shown in Chart I can be extended to further include additional donors, e.g., D3, D4, D5, and the like, or additional acceptors, e.g., A3, A4, A5, or the like.

The molar ratio of donor and acceptor can be varied and can be, for example, one, less than one, or more than one. In other words, the polymer does not need to comprise equal molar amounts of donor and acceptor. The polymer can comprise more donor than acceptor, or more acceptor than donor. Chart I shows examples of this. For example, the ratio can be 2:1.

In addition, random and/or alternating copolymers can be prepared. Different copolymer microstructures can be prepared as known to those skilled in the polymer chemistry arts. For example, random copolymer structures can be produced. Mixed monomer polymerization can be carried out. Non-random copolymer structures can be produced.

For the random copolymer embodiment, one can use appropriate synthetic sequence to obtain good materials. Synthetic approaches include, for example, Yamamoto, Suzuki, Negishi or Stille couplings for polymerization. See, for example (a) *Cross-Coupling Reactions: A Practical Guide*, Ed. Miyaura, 2002; (b) *Handbook of Organopalladium Chemistry for Organic Synthesis*, Ed. Negishi, 2002; (c) Kuwano, R, Utsunomiya, M., Hartwig, J. F., *J. Org. Chem.*, 2002, 67, 6479-6486; (d) Yu et al. *J. Am. Chem. Soc.* 2009, 131, 56; (e) Hou, J.; Park; M.-H.; Zhang, S.; Yao, Y.; Chen, L.-M.; Li, J.-H.; Yang, Y. *Macromolecules*, 2008, 41 (16), 6012-6018; (f) Blouin, N.; Michaud, A.; Gendron, D.; Wakim, S.; Blair, E.; Neagu-Plesu, R.; Belletête, M.; Durocher, G.; Tao, Y.; Leclerc, M. *J. Am. Chem. Soc.* 2008 130 (2), 732-742; (g) Swager et al. *Adv. Mater.* 2001, 13, 1775; (h) Koeckelberghs et al. *Macromolecules.* 2007, 40, 4173; (i) *High-Efficient-Low-Cost Photovoltaics*, Springer Verlag Berlin Heidelberg, 2009, Editors: Petrova-Kock, V.; Goetzberger, A., 195-222.

An additional embodiment from provisional 61/240,137 provides:

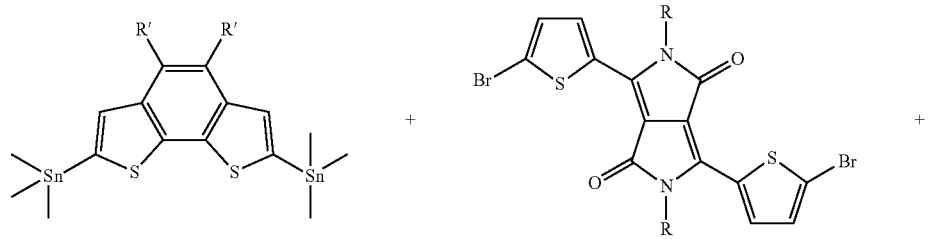

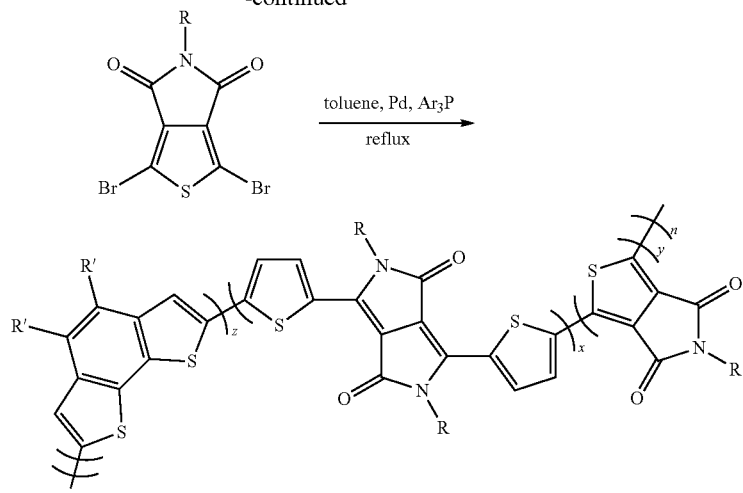

FIG. 1 of provisional 61/240,137 provides further embodiments.

In addition, polymers can be prepared wherein the polymer backbone comprises the moiety (XII):

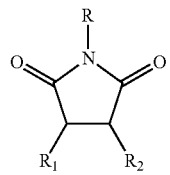

(XII)

wherein moiety XII is linked bivalently to the polymer backbone via the R1 and R2 groups, which can form a ring. In structure XII, the carbon atoms 3 and 4 of the pyrrole ring can be joined by a double bond to form part of an extended conjugated polymer chain, as shown in structure XIIA:

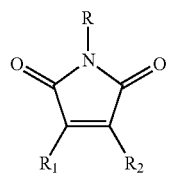

(XII-A)

The R1 and R2 groups can link together to form a ring, including for example a five- or six-membered ring including an all-carbon ring or a ring comprising a heteroatom, including a heterocyclic ring, including, for example, a thiophene ring or a benzene ring. The ring formed by R1 and R2 can be aromatic or pseudoaromatic. The ring can be bivalently functionalized so it can be incorporated into the polymer backbone.

Structure XI is an embodiment of structures XII and XII-A. Another example is structure XIIB:

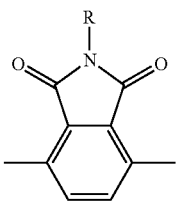

(XIIB)

The R groups described herein for (XI) can be used in (XII) also.

For structure XII, as with structure XI, the R group in one or more polymers can be varied, and different R groups can be used such as, for example, R1, R2, R3, or R', R", R"', and the like, wherein all are examples of R. For example, a single polymer can be prepared which comprises R1 and R2, wherein each of these are R. For example, a monomer with R1 can be copolymerized with a monomer comprising R2. Alternatively, a polymer comprising R1 can be blended with a polymer comprising R2. The R groups can be the same or different.

Structure XII can be used in the analogous manner as Structure XI is described herein.

In one embodiment, structure XII is directly, covalently linked through the ring, which is formed from the R1 and R2 groups, to at least one fused ring system, or at least two fused ring systems. Examples of fused ring systems are shown throughout this application including, for example, donor moieties in FIG. 1. In one embodiment, structure XII is not directly, covalently linked through the ring, which is formed from the R1 and R2 groups, to an unfused thiophene ring or an unfused benzene ring.

Polymers can be also prepared which comprise at least one backbone moiety represented by:

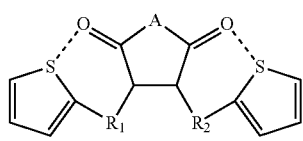

(XIII)

wherein A can be an optionally substituted alkylene moiety (e.g., optionally substituted methylene or ethylene, —(CH₂)ₓ— or a heteroatom, and wherein the moiety XII is bivalently linked to the polymer backbone via the illustrated thiophene rings linked to the R1 and R2 groups. In XIII, although a non-covalent interaction is illustrated as a dashed line between the thiophene ring sulfur and the carbonyl oxygen, such interaction is optional and not required. The thiophene rings can be linked to the polymer at their 2- and 5-positions. The thiophene rings can be linked to additional thiophene rings.

As with structure XII, in structure XIII, the carbon atoms 3 and 4 of the top ring comprising alkylene or heteroatom A can be joined by a double bond to form part of an extended conjugated polymer chain, as shown in structure XIII-B:

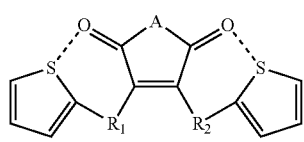

(XIII-B)

In the heteroatom embodiment for A, A can be, for example, nitrogen, oxygen, sulfur, or selenium. The nitrogen, if the heteroatom A, can be functionalized as shown in XI. The R group in structure XI is adapted for bonding to a nitrogen atom. In other structures such as XIII, described herein, R can bind to other atoms besides nitrogen, and R can be adapted accordingly.

In a manner similar to structure XII, R₁ and R₂ can form five or six-membered rings, including aromatic or pseudoaromatic rings, including heterocyclic rings, including benzene ring or thiophene ring.

Aromatic rings structures including aromatic rings structures, including benzidine ring structures, and biphenyl structures, can be used.

Structures XI and XII can be embodiments of structure XIII.

As with Structures XI and XII, the R groups in structures XIII (R1 and R2) in one or more polymers can be varied, and different R groups can be used such as, for example, R1, R2, R3, or R', R'', R''', and the like, wherein all are examples of R. For example, a single polymer can be prepared which comprises R1 and R2, wherein each of these are R. For example, a monomer with R1 can be copolymerized with a monomer comprising R2. Alternatively, a polymer comprising R1 can be blended with a polymer comprising R2. The R groups can be the same or different.

In one embodiment, the illustrated thiophene rings in structure XIII are part of at least one fused ring system, or at least two fused ring systems. Examples of fused ring systems are shown throughout this application including, for example, donor moieties in FIG. 1. In one embodiment, the illustrated thiophene rings in structure XIII are not unfused thiophene rings.

Polymers can be also prepared wherein the backbone comprises a structure represented by XIV

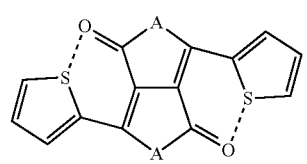

(XIV)

Here, A can be an optionally substituted alkylene or heteroatom such as, for example, N, O, S, or Se, as described above for structure XIII. The A group can comprise substituents such as the R group in structure XI. For example, the R group in structure XIV can be adapted for bonding to a nitrogen atom. In structures such as XIV described herein, R can bind to other atoms besides nitrogen, and R can be adapted accordingly.

The structure XIV can be linked into the polymer chain via the illustrated thiophene rings.

As with Structures XI, XII, and XIII, the R groups in structure XIV in one or more polymers can be varied, and different R groups can be used such as, for example, R1, R2, R3, or R', R'', R''', and the like, wherein all are examples of R. For example, a single polymer can be prepared which comprises R1 and R2, wherein each of these are R. For example, a monomer with R1 can be copolymerized with a monomer comprising R2. Alternatively, a polymer comprising R1 can be blended with a polymer comprising R2. The R groups can be the same or different.

In one embodiment, the illustrated thiophene rings in structure XIV are part of at least one fused ring system, or at least two fused ring systems. Examples of fused ring systems are shown throughout this application including, for example, donor moieties in FIG. 7. In one embodiment, the illustrated thiophene rings in structure XIV are not unfused thiophene rings.

Embodiments from 61/241,813

U.S. provisional application 61/241,813 filed Sep. 11, 2009 provides additional embodiments. These embodiments can be adapted to include benzo[2,1-b:3,4-b']dithiophene moieties.

Diketopyrrolopyrrole-based compounds are known in the art. See, for example, U.S. Pat. No. 4,585,878 (Ciba-Geigy), U.S. Pat. No. 4,778,899 (Ciba-Geigy), U.S. Pat. No. 4,931,566 (Ciba-Geigy), PCT publication WO 2008/000664, and European patent applications EP 0962499A2, EP 0094911B1, EP 0181290 B1, EP 0302018 B1, EP 0302018 B1, EP 0672729 B1, and EP 0962499 B2. See, also, Yu Zhu Doctoral Dissertation, University of Koln, 2006. Diketopyrrolopyrrole also can be called DPP, as known in the art.

One embodiment provided herein comprises materials, including an oligomer or a polymer, having a donor-acceptor structure, wherein the donor comprises a fused ring system which is directly and covalently linked to an acceptor structure comprising diketopyrrolopyrrole structure. Particularly embodiments are provided, wherein the fused ring system comprises a fused thiophene ring which is directly, covalently linked to the acceptor structure.

Also provided is a composition comprising an oligomer or a polymer having a donor-acceptor structure, wherein the acceptor comprises a diketopyrrolopyrrole structure which is not directly and covalently linked to a donor structure by an unfused thiophene or an unfused benzene ring.

In addition to embodiments shown above, including structure VII, also provided are low molecular weight, oligomeric, and polymeric materials comprising at least one moiety represented by structure VIII and substructure IX:

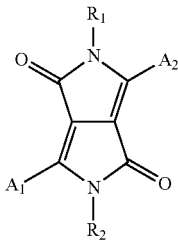
(VIII)

wherein A1 and A2 each independently comprise a fused ring system comprising at least two fused rings directly covalently linked to the substructure of VIII represented as substructure IX:

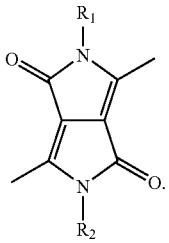
(IX)

A1 and A2 are moieties which form part of the copolymer repeat unit, binding the moiety VIII to a larger polymer backbone, and can comprise a donor moiety, for example.

Another embodiment provides low molecular weight, oligomeric, and polymeric materials comprising at least one moiety represented by:

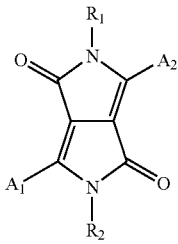
(VIII)

wherein A1 and A2 each independently do not comprise an unfused thiophene or unfused benzene ring directly covalently linked to the substructure of VIII represented as substructure IX:

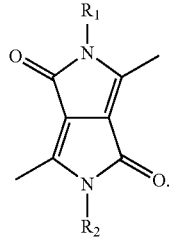
(IX)

Again, A1 and A2 are moieties which form part of the copolymer repeat unit, binding the moiety VIII into a larger polymer backbone, and can comprise a donor moiety, for example.

A1 and A2 can be the same or different. Symmetrical structures can be used or unsymmetrical structures. The following is a moiety which comprises one A1 moiety on the left side which can comprise a fused ring system directly and covalently linked to the substructure IX, or A1 can be adapted so it does not comprise an unfused thiophene or benzene ring:

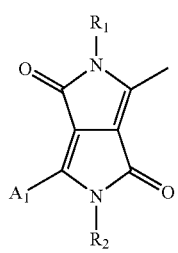
(VIII-C)

However, in VIII-C, the right side dangling bond extending out of the pyrrole ring need not be so limited. Structure VIII-C is an example of an unsymmetrical moiety.

Structure VIII-D through VIII-H below illustrate examples of an unfused thiophene ring which is directly, covalently linked to substructure IX.

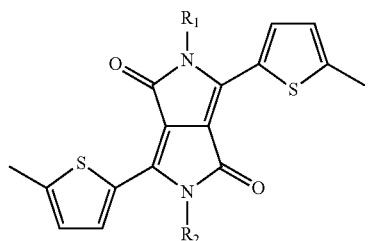
(VIII-D)

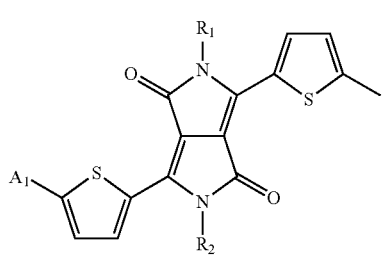
(VIII-E)

-continued

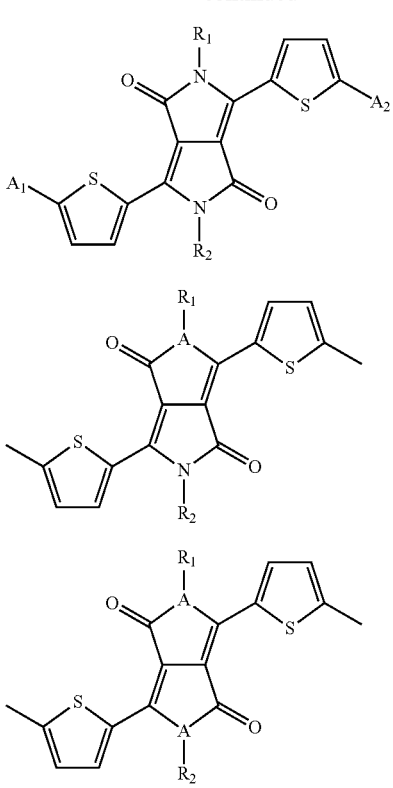

(VIII-F)

(VIII-G)

(VIII-H)

Polymers can be prepared which exclude such moieties as VIII-D to VIII-H, or use them as a minor component by molar ratio compared to the amount of a major acceptor component.

These materials, including polymeric materials, comprising moieties such as those shown in structures VIII and IX can be fabricated into solutions, inks, coated substrates, and organic electronic devices, including photovoltaic devices, as can the materials described above. The lower molecular weight materials, including dimers, trimers, and oligomers, can be adapted to be polymerizable for use in polymerization reactions. They can be, for example, functionalized to comprise at least two polymerizable groups which are capable of participating in polymerization reactions. Polymerization reactions are described throughout this application including, for example, cross-coupling polymerization.

Polymers can be prepared which comprise both structures XI and VIII. However, in some embodiments, the materials do not comprise the moiety of structure I.

In some embodiments, the materials, including oligomers and polymers, comprise a donor-acceptor structure, wherein the acceptor comprises (VIII).

In some embodiments, the materials, including the polymers, are soluble. In some embodiments, the R groups, R1 and R2, can be adapted to provide the polymer with solubility. In some embodiments, the R groups, R1 and R2, can each comprise optionally substituted alkyl, optionally substituted linear alkyl, optionally substituted branched alkyl, optionally substituted cycloalkyl, optionally substituted aryl, optionally substituted alkylaryl, optionally substituted arylalkyl, optionally substituted alkoxy, or optionally substituted aryloxy, and optionally, wherein R groups, R1 and R2, further comprises fluorine. Examples of fluorinated R groups include fluorinated alkyl and fluorinated aryl groups, including perfluorinated alkyl groups and perfluorinated aryl groups.

The structure VIII can be a symmetrical structure. For example, in some embodiments, the R groups, R1 and R2, are the same, and A1 and A2 are also the same. However, R1 and R2 can be different, and A1 and A2 can be different.

In some embodiments, the fused ring systems in VIII can comprise at least one thiophene fused ring, wherein the thiophene ring is directly linked to the substructure IX. For example, polymers can be also prepared wherein the backbone comprises a structure represented by VIII-B:

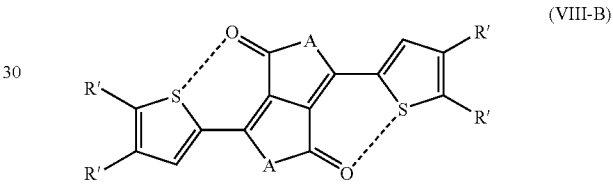

(VIII-B)

Here, A can be a heteroatom such as, for example, N, O, S, or Se and may be optionally substituted with alkyl, aryl, perfluoroalkyl, perfluoroaryl, alkyl-aryl as described above with respect to structure I and other structures. The R' groups in VIII-B can form additional ring systems, including fused ring systems, and the structure VI can be linked into the polymer chain via the illustrated thiophene rings. For example, the R' groups can form a benzene ring, a naphthalene ring, or a ring comprising silicon (silole). In structure VIII-B, a potential interaction is shown between carbonyl oxygen and thiophene sulfur, although the claimed inventions are not limited by the theory of this interaction.

Examples of polymers comprising the diketopyrrolopyrrole-based structure include polymers as represented by the following structures:

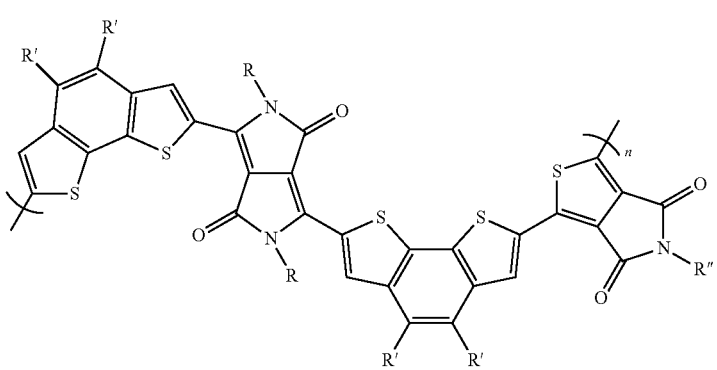

(XV-A)

-continued
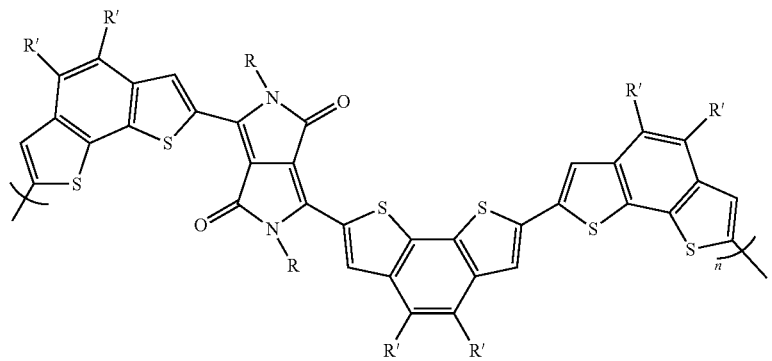
(XV-B)
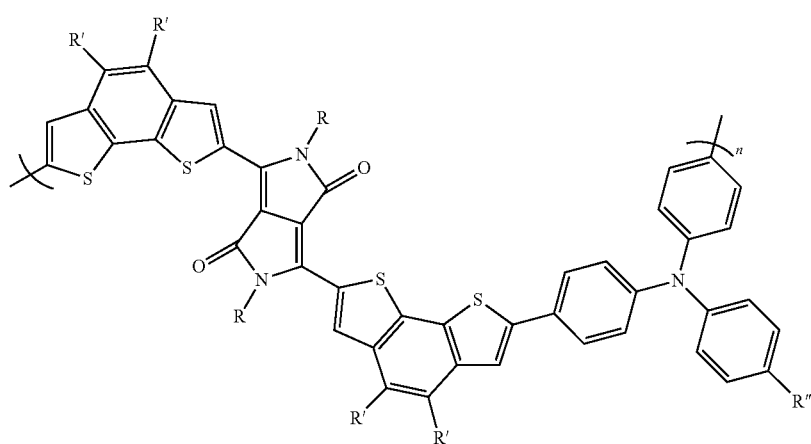
(XV-C)
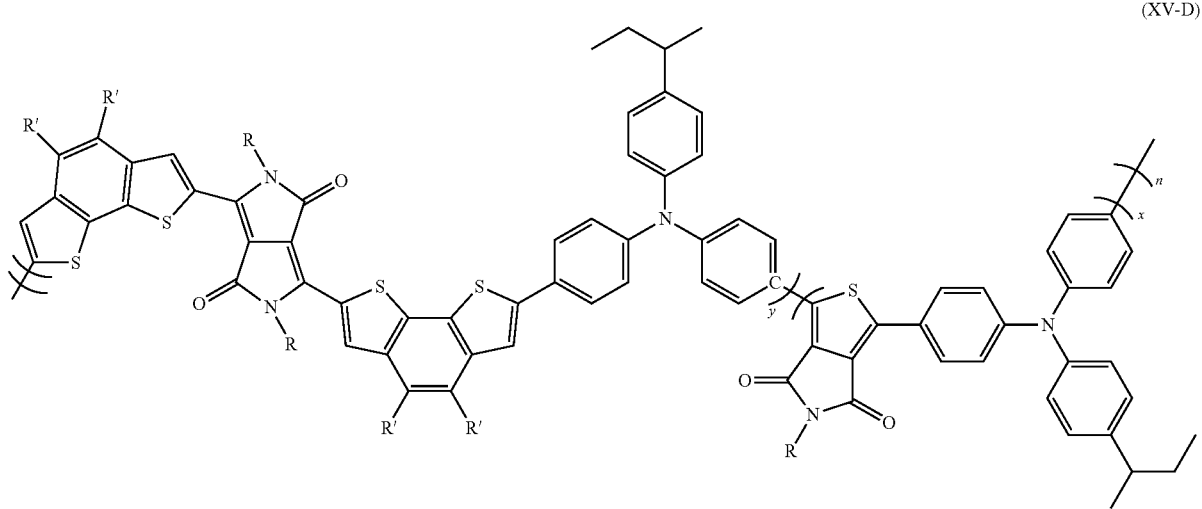
(XV-D)
In structures XV, the variables shown such as n, x, and y can be adapted according to the descriptions herein to control molecular weight and copolymer structure. Moreover, R, R', and R" can be the same or different for a given polymer chain and can be as described above for structure I and other polymer side groups described herein.

Additional embodiments for the diketopyrrolopyrrole-based materials include the following moieties, which can be found in dimers, trimers, oligomers, or high polymers:
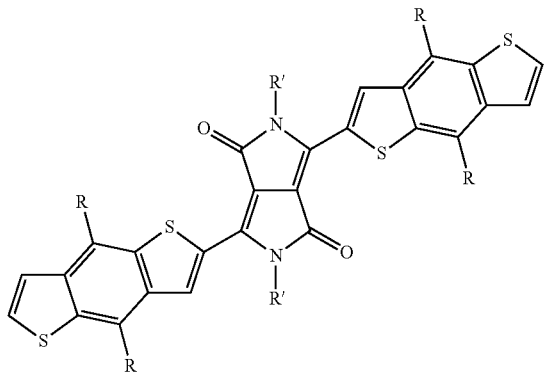
(XVI-a)
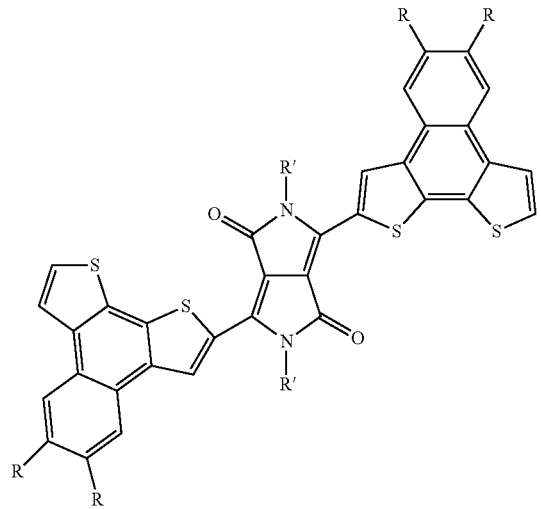
(XVI-b)
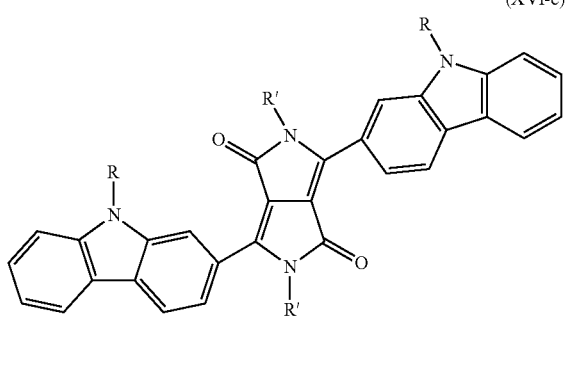
(XVI-c)
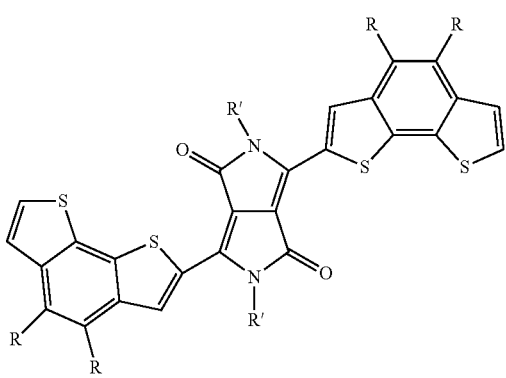
(XVI-d)
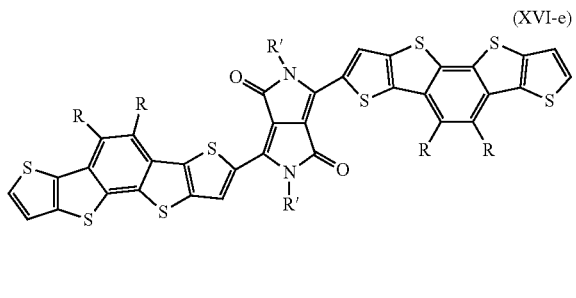
(XVI-e)
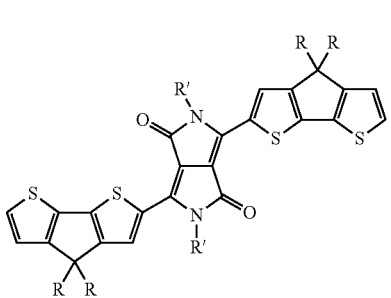
(XVI-f)
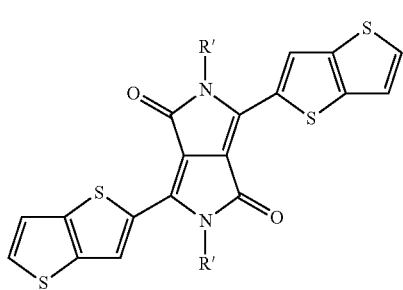
(XVI-g)

-continued
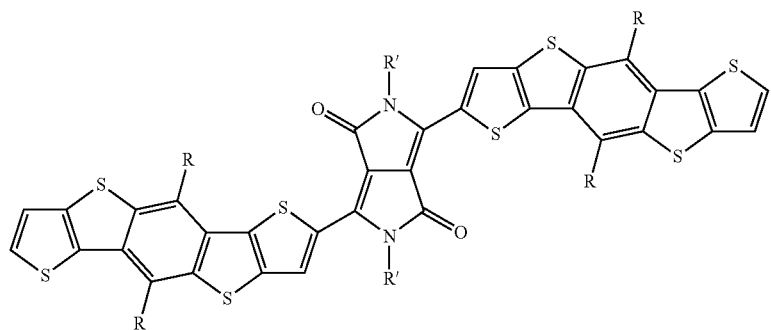
(XVI-h)
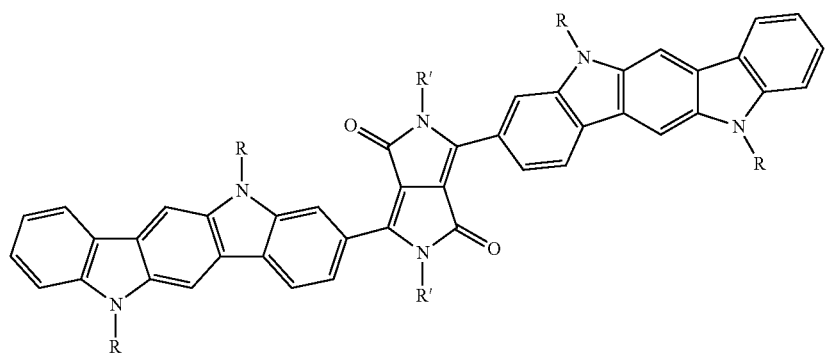
(XVI-i)
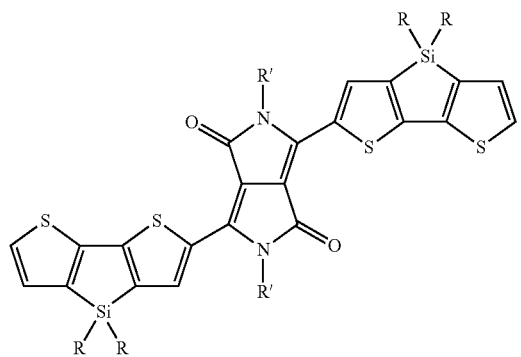
(XVI-j)
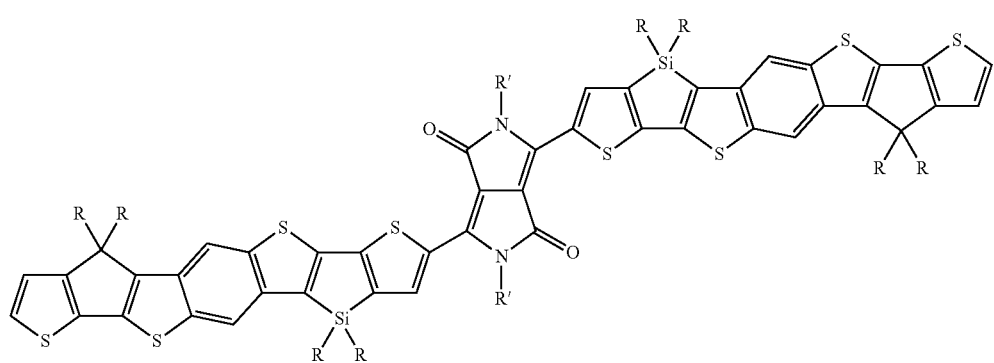
(XVI-k)

-continued
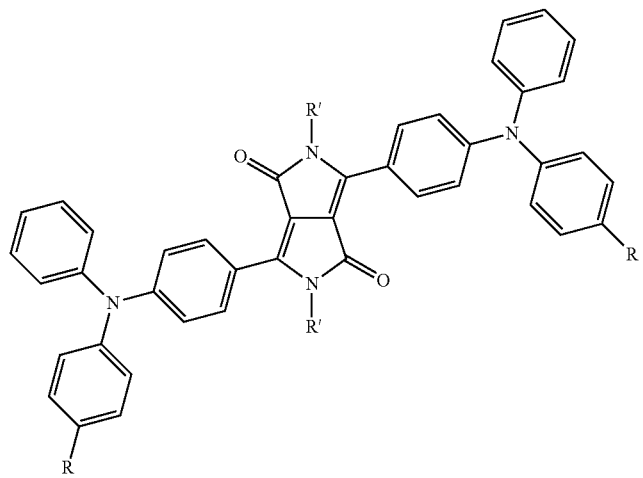
(XVI-l)
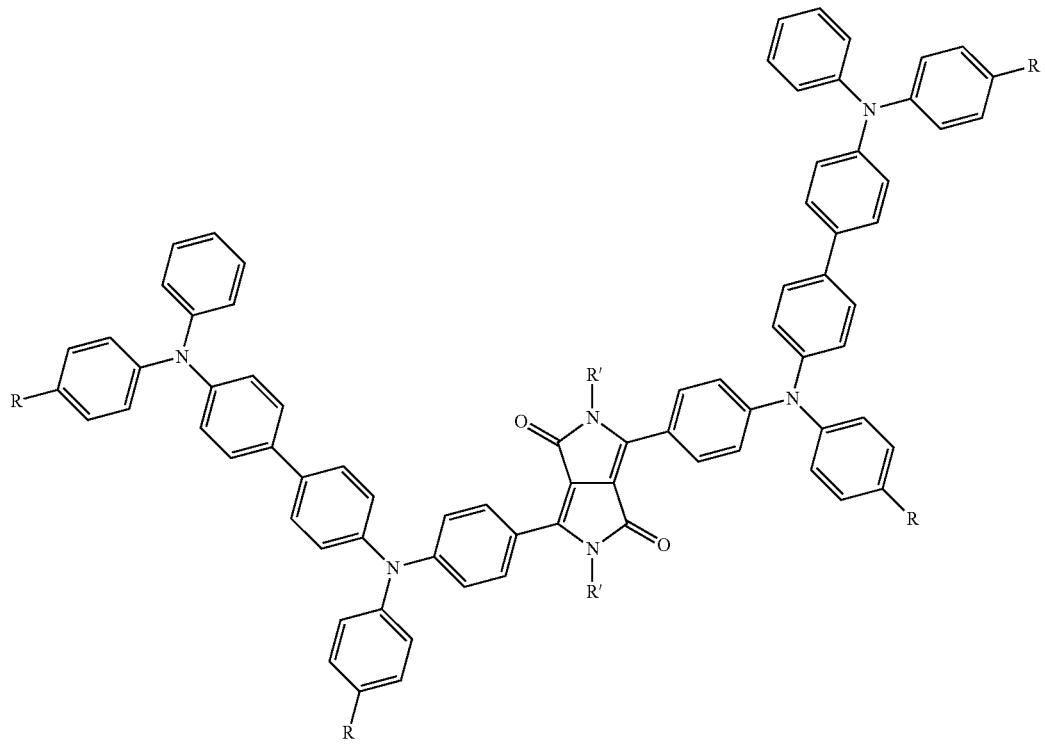
(XVI-m)

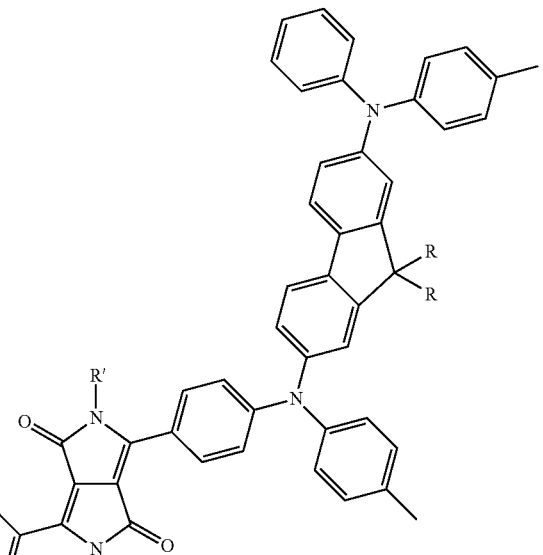

(XVI-n)

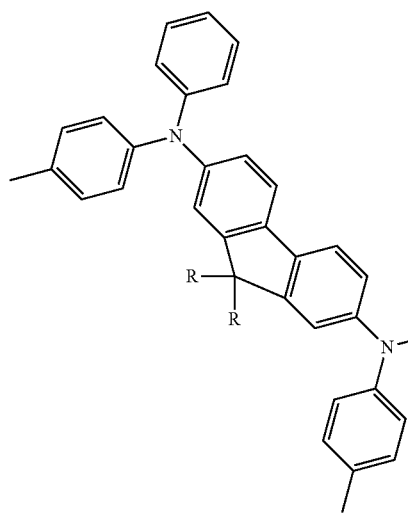

In some embodiments, such as structures XVI-l, XVI-m, and XVI-n, some of the DPP unit (structure IX) can be directly, covalently linked to the unfused phenyl ring of an arylamine moiety.

In structures XVI, the side groups R and R' can be as described above, and the R and/or R' groups for a given polymer can be the same or different for a given polymer.

Figure 7:
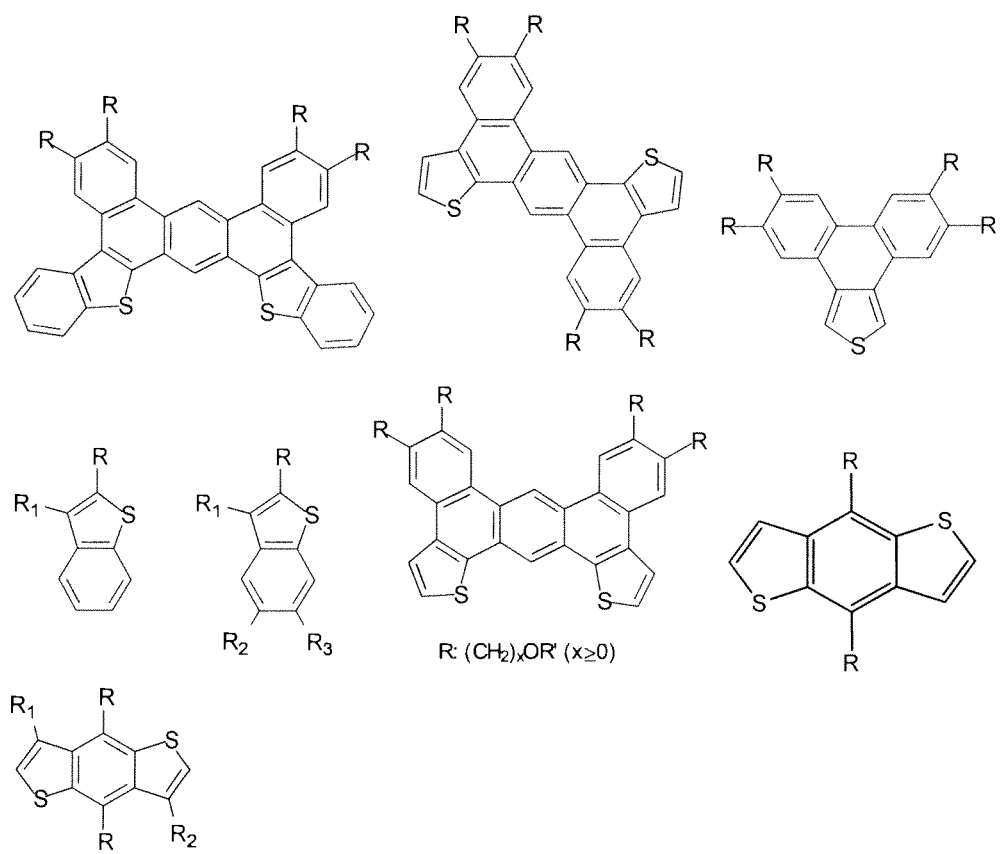
FIG. 7 provides examples of donor structures which can be used in a donor acceptor copolymer.

Polymers can be prepared which have a microstructure as shown in Chart I and can provide different copolymer microstructure based on multiple acceptors A1, A2, and the like, and/or multiple donors, D1, D2, and the like. Polymers can be prepared which have donors and acceptors as shown in FIGS. 7 and 8.

Polymers can be prepared which show an intramolecular non-covalent interaction, as described above, in, for example, a carbonyl interaction with an adjacent thiophene ring.

Polymers can be prepared wherein all or substantially all of the units shown in VIII are directly, covalently linked to the fused ring systems, or wherein only a fraction of the units shown in VIII are directly, covalently linked to the fused ring systems.

Diketopyrrole monomers can be made according to known procedures from extensive literature precedent. See, for example, Peet et al., *Appl. Phys. Lett.,* 2009, 93, 163306; Janssen et al. *Adv. Mat.,* 2008, 20, 2556; Zhu, Y. Ph.D. Dissertation, University of Koln, Germany, 2006; Yang et al. *J. App. Polymer Sci,* 2009, 111, 1976; EA00962499A2; EB0094911B1; EB00133156B1; EB00181290B1; EB00302018B1; EB00672729B1; EB 00962499B2; Tamayo et al., *J. Phys. Chem. C.,* 2008, 17402; Boens et al.,; *Int. J. Photoenergy,* 2004, V6, 2004, 159; Lunak et al., *J. Fluoresc Chem.* 2008, 18, 1181; Tamayo et al. *APL,* 2009, 94, 103301; Tamayo et al., *J. Phys. Chem. C,* 112, 11545; U.S. Pat. No. 4,585,878; U.S. Pat. No. 4,778,899; U.S. Pat. No. 4,921,566; WO08000664A1; Burgi et al., *Adv. Mater.* 2008, 20, 2217.

For example the new monomers can be prepared according to the following typical sequence, which illustrates a benzodithiophene embodiment and which can use the benzo[2,1-b-3,4-b']benzodithiophene moieties described herein:

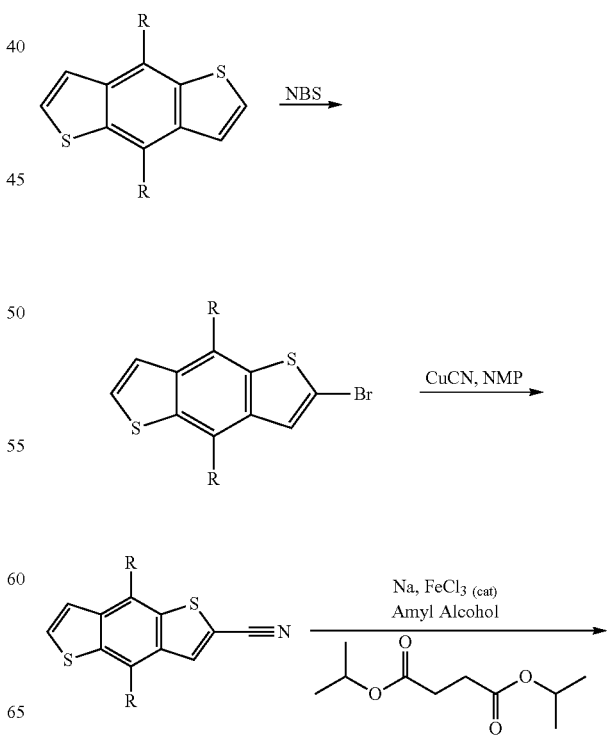

63
-continued
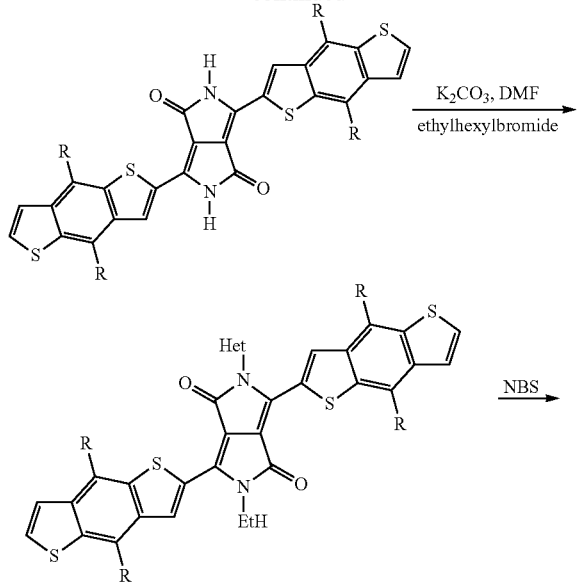
64
-continued
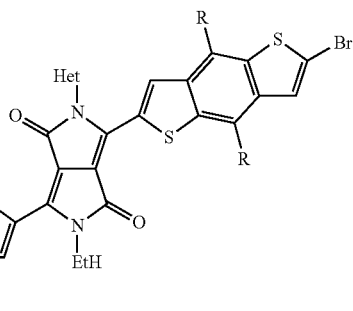
One embodiment provides a general procedure for the synthesis of alternating copolymers via Stille cross-coupling polymerization
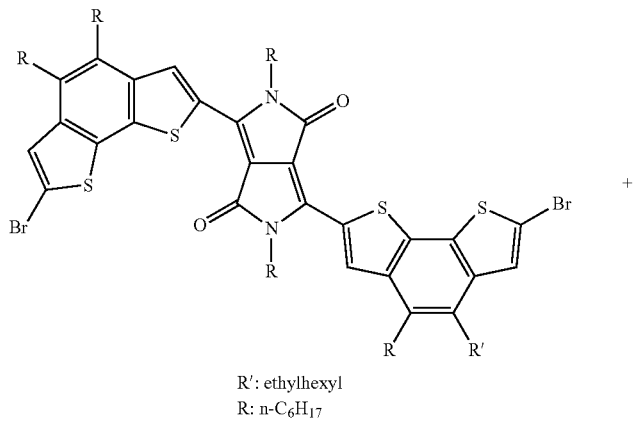
R': ethylhexyl
R: n-C₆H₁₇
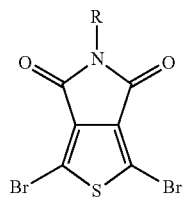
+
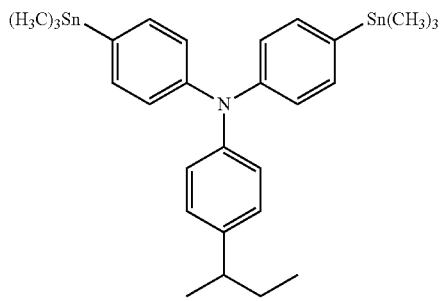
Pd₂(dba)₃/(o-tolyl)₃P
toluene, 110° C.

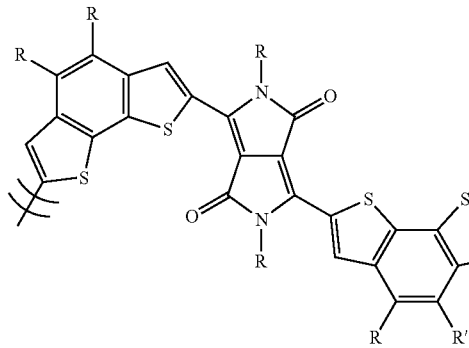
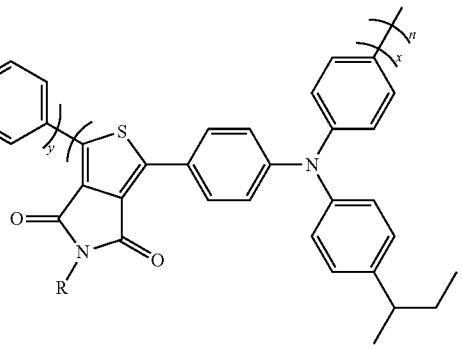

Experimental parameters which can be used and adapted by those skilled in the art include:

In a glove box, dibromo-1,4-bis[4,5-bis(2-ethylhexyl) thieno[3,2-g]benzothiophen-2-yl]-2,5-dioctyl-pyrrolo[3,4-c]pyrrole-3,6-dione (0.50 mmol), 1,3-dibromo-5-(n-octyl) thieno[3,4-c]pyrrole-4,6-dione (0.50 mmol), N-(4-sec-butylphenyl)-4-trimethylstannyl-N-(4-trimethylstannylphenyl)aniline (1.0 mmol), tris (dibenzylideneacetone)dipalladium(0) (2.5 mol %) and tris (o-tolyl)phosphine (0.050 mmol) are charged into a flame dried 50 mL Schlenk flask. The reaction flask is removed from the glove box and 15 mL of deoxygenated toluene are added via syringe. The mixture is evacuated and refilled with argon five times. The reaction flask is immersed into a preheated to 110° C. oil bath and left stirring under an argon stream for 12 hours. The polymerization is quenched with 0.3 mL of 2-iodothiophene and stirred at 110° C. for additional two hours. The oil bath is removed and after cooling to room temperature, 15 mL of methanol are added to the reaction mixture under vigorous stirring to induce precipitation. The final mixture is poured into 200 mL of methanol, and polymer is collected via filtration. The polymer is purified by consecutive Soxhlet extractions in sequence with methanol, acetone, hexane, and chloroform. The chloroform fraction is passed through celite, to remove catalyst residuals, and solvent is removed under vacuum to yield polymer. Hexanes and chloroform fractions are concentrated, re-precipitated in methanol, isolated via filtration, and analyzed by gel permeation chromatography (GPC) and NMR.

Polymer samples can be precipitated in methanol, filtered, and purified by Soxhlet extractions utilizing successively methanol, acetone, hexanes, and chloroform and/or passing through a bed of celite. Hexanes and chloroform fractions are concentrated, re-precipitated in methanol, isolated via filtration, and analyzed by gel permeation chromatography (GPC) and NMR.

Embodiments from 61/290,844

U.S. provisional application 61/248,335 filed Oct. 2, 2009 provides additional embodiments. These embodiments can be adapted to include benzo[2,1-b:3,4-b']dithiophene moieties.

Of particular interest are regular alternating copolymers comprising at least three moieties. In some cases, the at least three moieties comprise at least one donor moiety and at least one acceptor moiety. They may comprise two or more donor moieties or two or more acceptor moieties. They may even comprise two or more donor moieties and two or more acceptor moieties. They may further comprise spacer moieties.

Some examples of such copolymers follow, where D1 and D2 denote donor moieties, and A1 and A2 denote acceptor moieties are shown in Chart II below.

Chart II

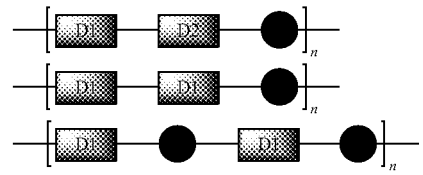

where n is an integer. Other embodiments include, for example, -[A1-A2-D1]$_n$- and -[A1-A1-D1]$_n$-.

A variety of intramolecular non-covalent interactions such as electrostatic, coulombic, hydrogen bonding or chelates can be used to provide increased rigidity and/or planarity to the polymer chain and its chromophores, although various embodiments described herein are not necessarily limited by theory. Increased rigidity can be used to increase the likelihood for a well behaved excited state and lead to good excitonic diffusion distances and minimization of energy loss pathways from excited state (e.g., charge trapping, polaronic quenching, excited state deactivation, or even localization). Absorption profiling can be used to examine such features. In particular, while various embodiments described herein are not necessarily limited by theory, it is believed that for at least some embodiments, a carbonyl group can interact with a nearby thiophene sulfur. The carbonyl oxygen is negatively charged compared to the thiophene sulfur which is relatively positively charged. This can provide planarization and/or increase rigidity in the backbone and improve performance. The interactions can be measured by methods known in the art including, for example, x-ray or NOE (Nuclear Overhauser Effect).

See, for example, Pomerantz et al., *Synthetic Metals*, 2003, 135-136, 257-258; Pomerantz et al., *Tetrahedron Letters*, 2003, 44(8), 1563-1565; and Pomerantz et al., *Tetrahedron Letters*, 40, 1999, 3317-3320.

In addition to carbonyl oxygen:sulfur interaction, other electrostatic or coordination bonding interactions can be used to help planarize, bridge, rigidify and thus, control moiety dihedral angles providing advantaged chemico-physical properties (e.g., photophysics and electrical). For example, sp$^2$ nitrogen and ethereal oxygen can be used. Other examples include pyridine, imidazole, ketone, ether, lactone, lactam, and amidine. One particularly useful monomeric unit for the polymer backbone is a thiophene ring which is substituted at the 3- and 4-positions by a bridging dialkoxyalkylene motif such as, for example, —OR—O wherein R is an alkylene moiety, such as —OCH$_2$CH$_2$O— (commonly known as EDOT).

For additional examples, one embodiment provides a composition comprising a regular alternating conjugated copolymer comprising at least three backbone donor and acceptor moieties, said moieties comprising at least one donor moiety, at least one acceptor moiety, and at least one additional different donor or acceptor moiety, wherein the copolymer comprises at least one benzo[2,1-b:3,4-b']dithiophene moiety. In one embodiment, said moieties comprise at least two different donor moieties. In another embodiment, said moieties comprise at least two different acceptor moieties. In one embodiment, the copolymer is a soluble copolymer. In one embodiment, the copolymer has a number average molecular weight of at least 5,000 g/mol. In one embodiment, the copolymer further comprising at least one spacer moiety.

In one embodiment, said at least one donor moiety is denoted by D1 and/or D2 and said at least one acceptor moiety is denoted by A1 and/or A2, and wherein said copolymer is represented by at least one of the following structures in Chart II.

In one embodiment, the copolymer does not comprise an unfused heterocyclic ring in the backbone. In one embodiment, the copolymer does not comprise an unfused thiophene ring in the backbone.

In one embodiment, at least one of the donor moieties and at least one of the acceptor moieties are linked so that they can engage in an intramolecular non-covalent interaction.

In one embodiment, the copolymer is prepared by copolymerization of two different monomers, wherein at least one monomer comprises both a donor and an acceptor, and the second monomer comprises a donor or an acceptor.

In one embodiment, the copolymer comprises a fluorinated backbone.

In one embodiment, the copolymer comprises at least one fluorinated side group.

In one embodiment, the composition further comprises an n-type acceptor in addition to the copolymer.

In one embodiment, the composition further comprises a fullerene derivative in addition to the copolymer.

In one embodiment, the backbone comprises a nitrogen atom.

In one embodiment, a composition is provided comprising a regular alternating conjugated copolymer comprising at least three backbone donor and/or acceptor moieties, said moieties comprising at least one donor moiety, at least one acceptor moiety, and at least one additional different donor or acceptor moiety, wherein said moieties do not comprise an unfused thiophene moiety. In one embodiment, said moieties comprise at least two different donor moieties. In another embodiment, said moieties comprise at least two different acceptor moieties.

In one embodiment, the copolymer is a soluble copolymer.

In one embodiment, the copolymer has a number average molecular weight of at least 5,000 g/mol.

In one embodiment, the copolymer further comprises at least one spacer moiety.

One embodiment provides a composition comprising a regular alternating conjugated copolymer comprising at least three backbone donor and/or acceptor moieties, said moieties comprising at least one donor, at least one acceptor, and at least one different donor or acceptor, wherein at least one moiety is represented by one of the structures:

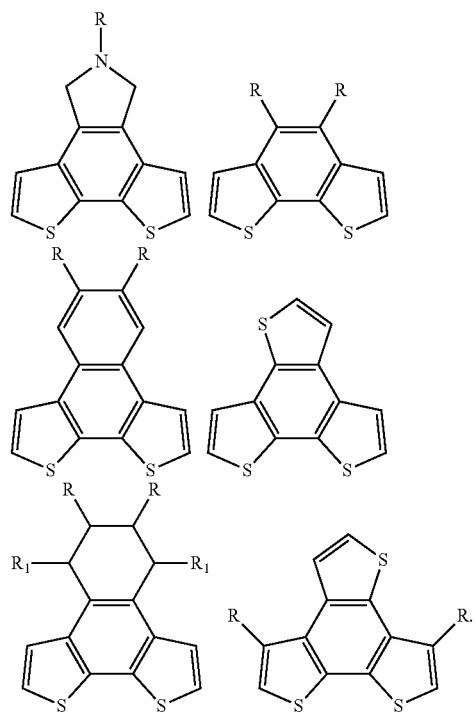

R can be, for example, alkoxy, polyether, alkyl, branched alkyl, or tri-substitutedsilyl. In one embodiment, at least one moiety is represented by one of the structures:

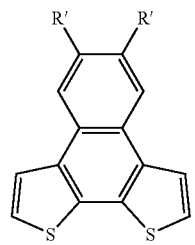

where R' can be, for example, alkoxy, polyether, alkyl, branched alkyl, or tri-substitutedsilyl.

Figure 6:
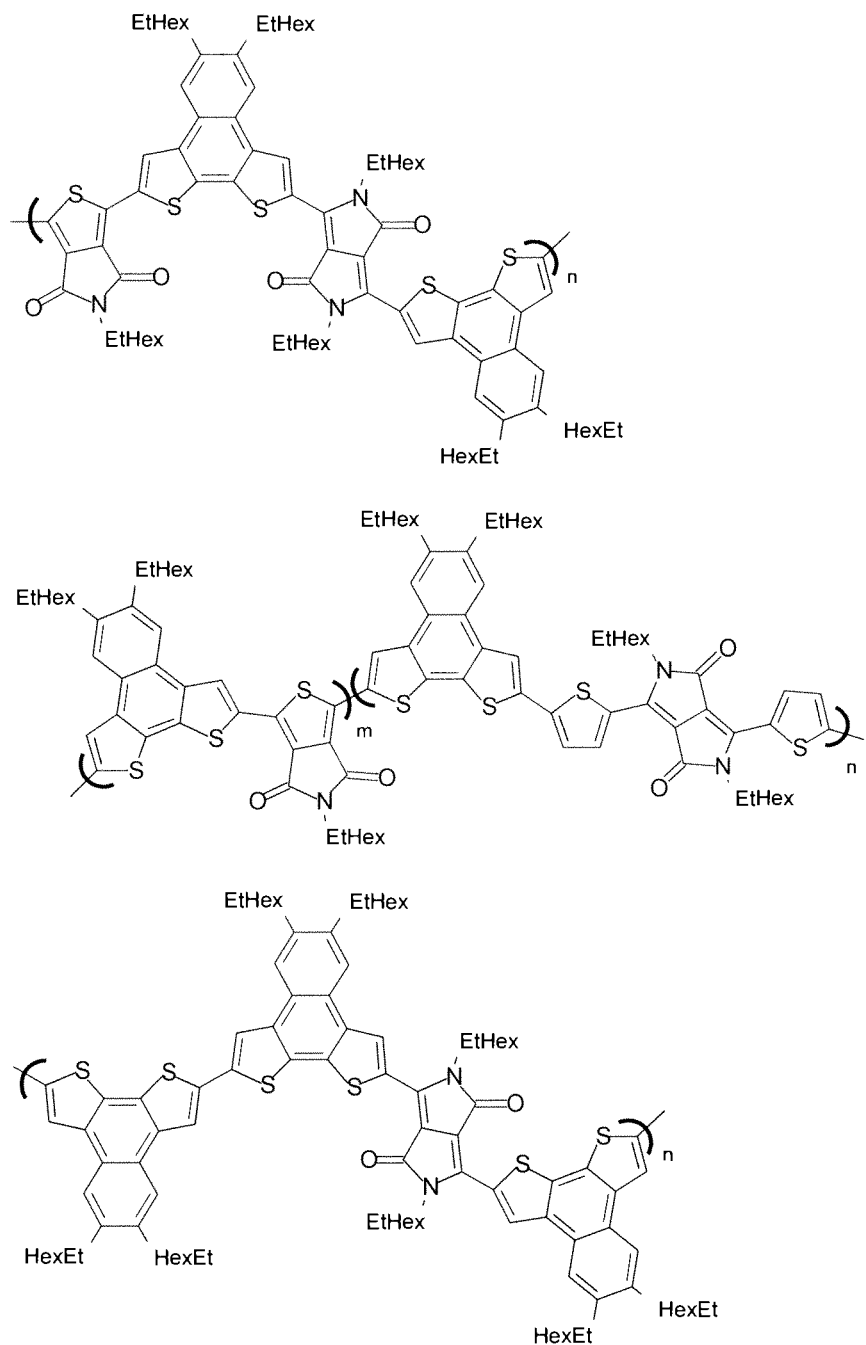
FIG. 6 illustrates additional benzo[2,1-b:3,4-b'] dithiophene structures.
Figure 6:
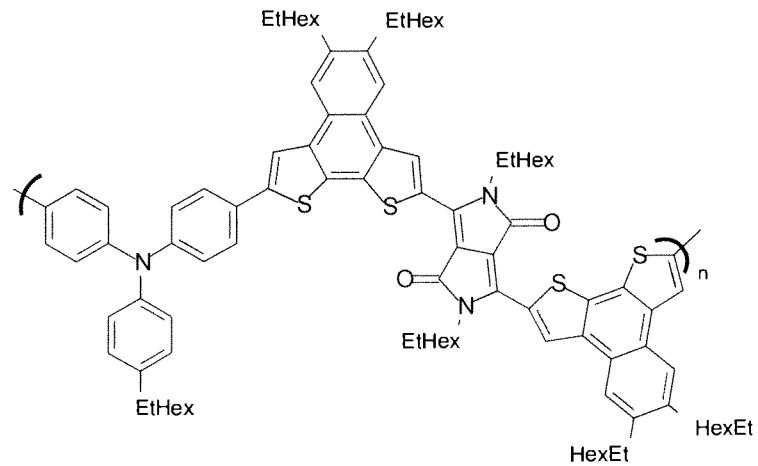
Figure 6:
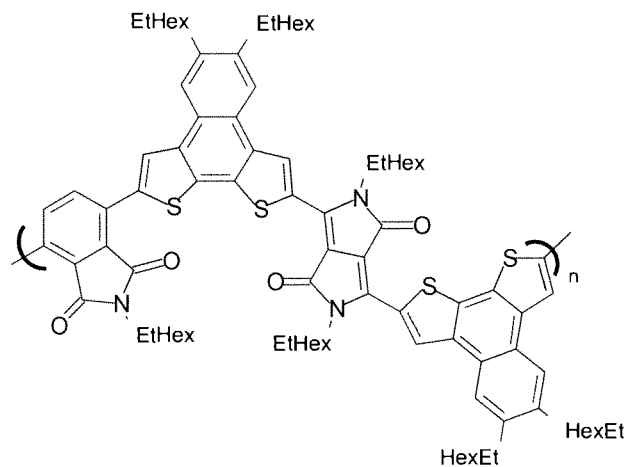
Figure 6:
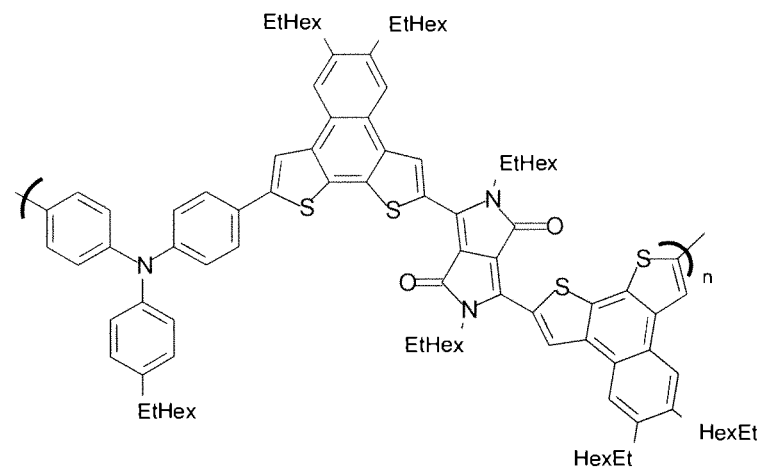
Figure 6:
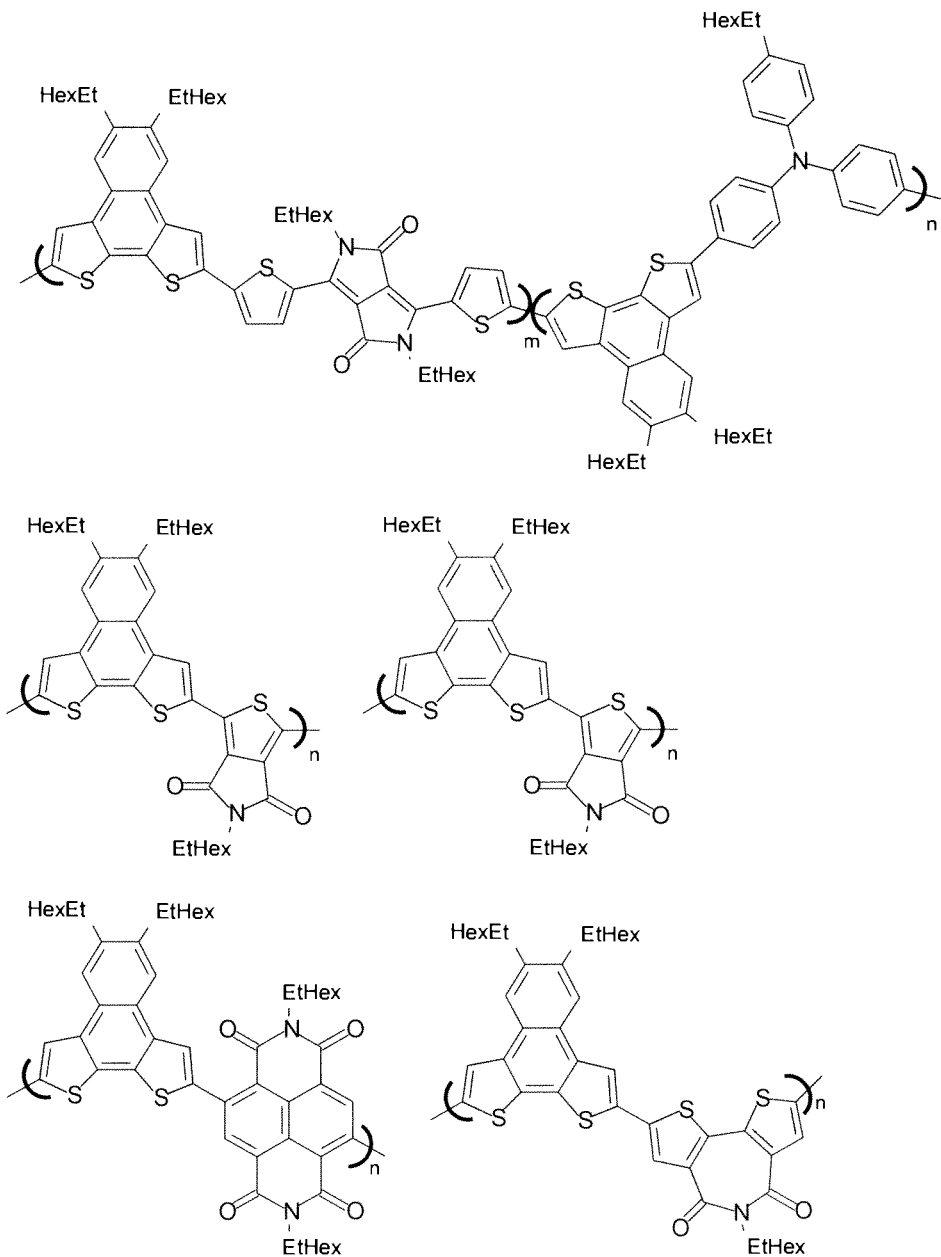
Figure 6:
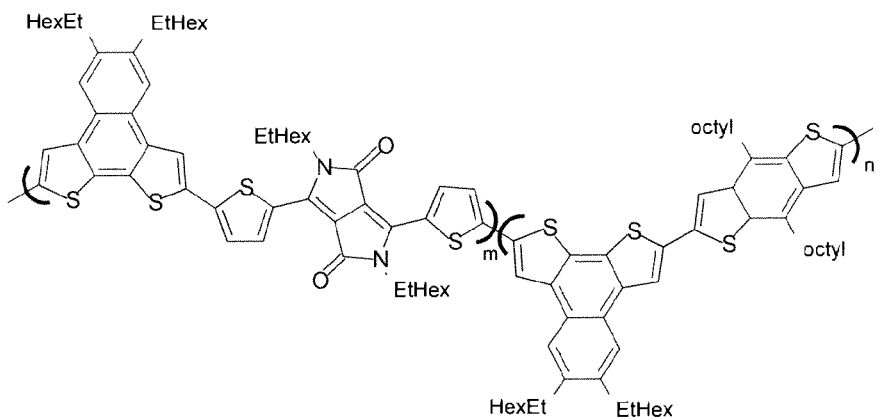
Figure 6:
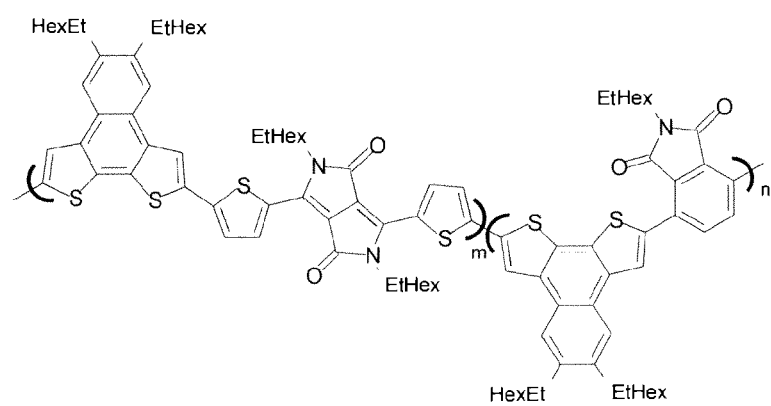
Figure 6:
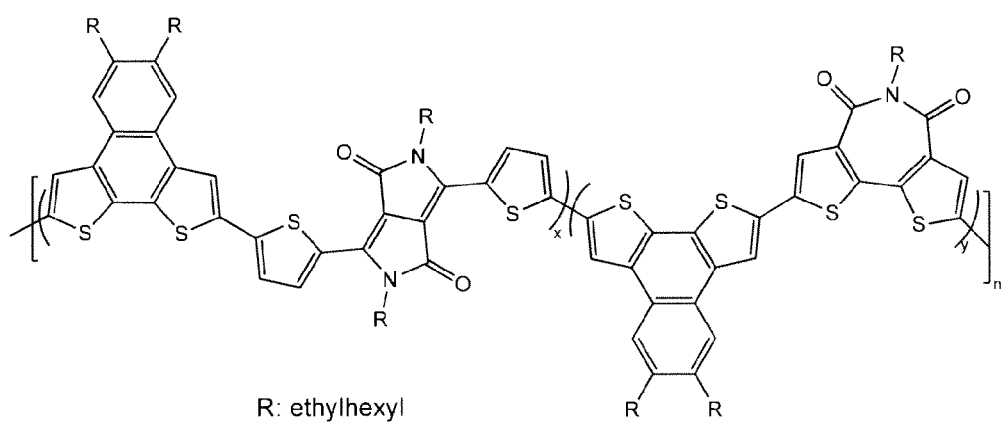
Figure 6:
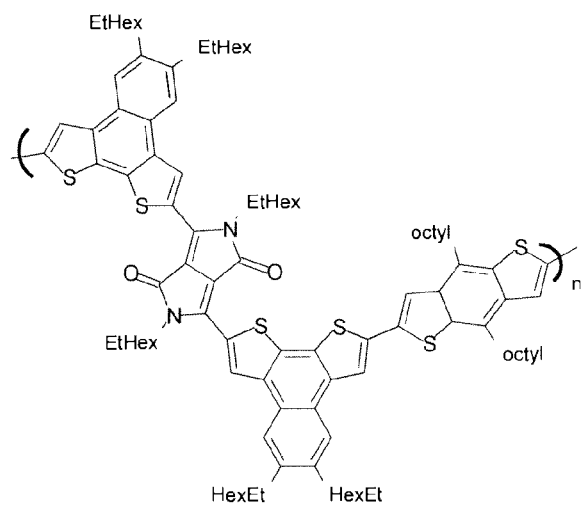
Figure 6:
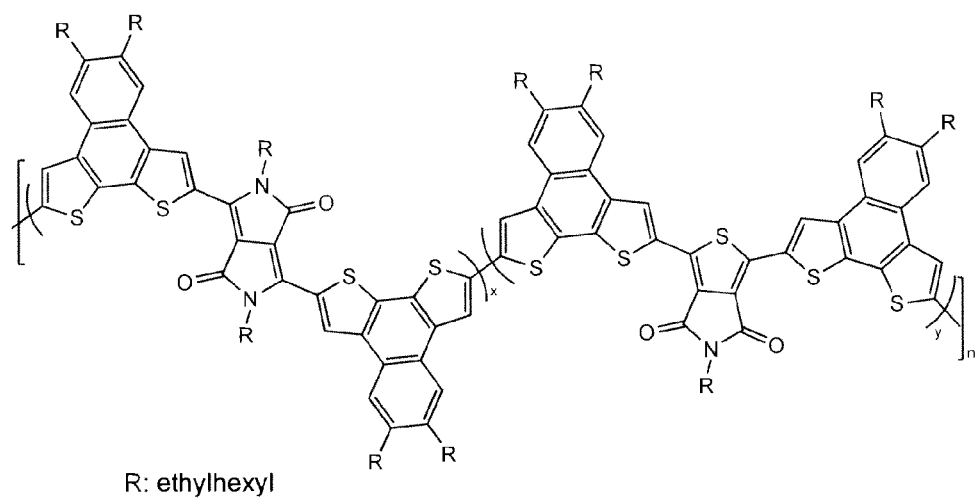
Figure 6:
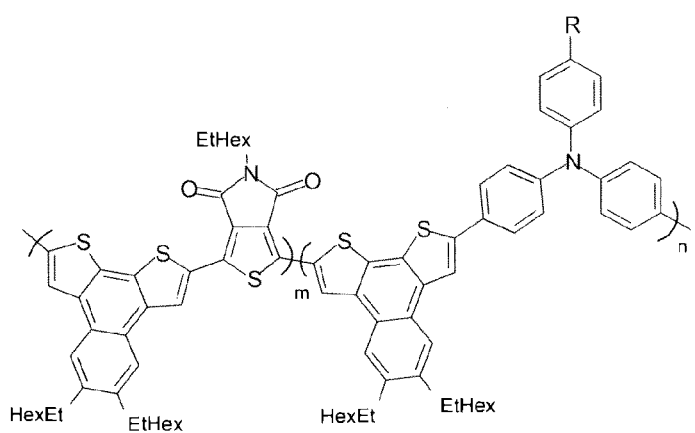
Figure 6:
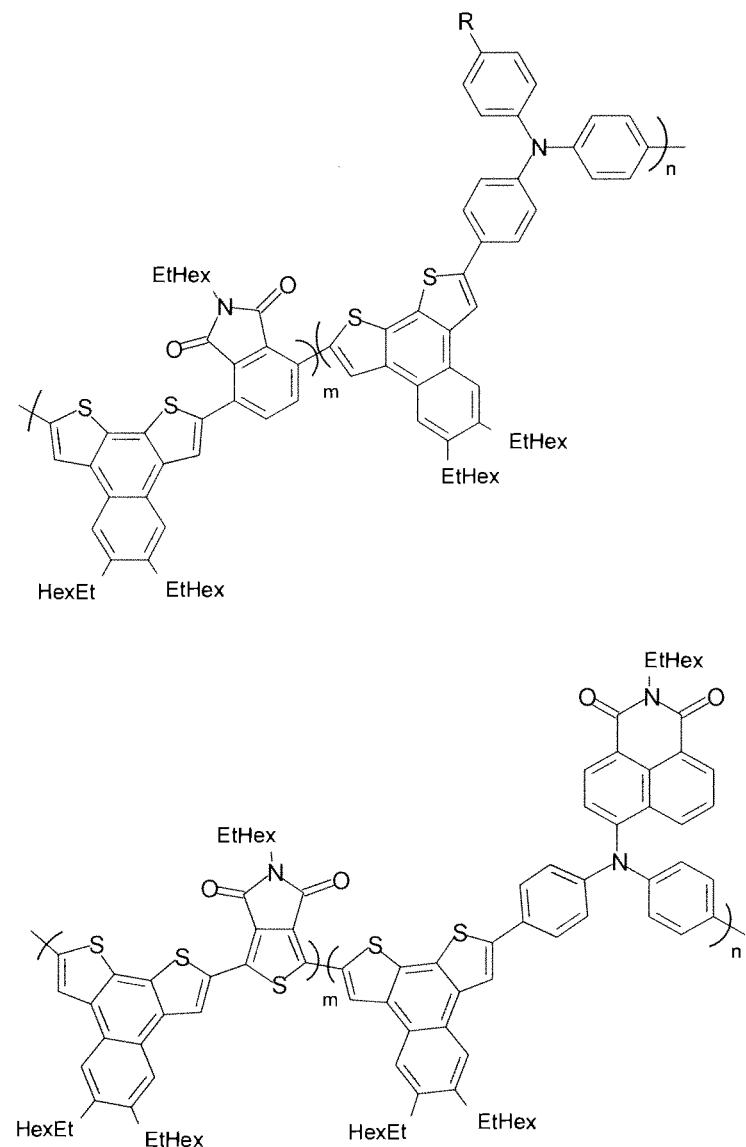
Figure 6:
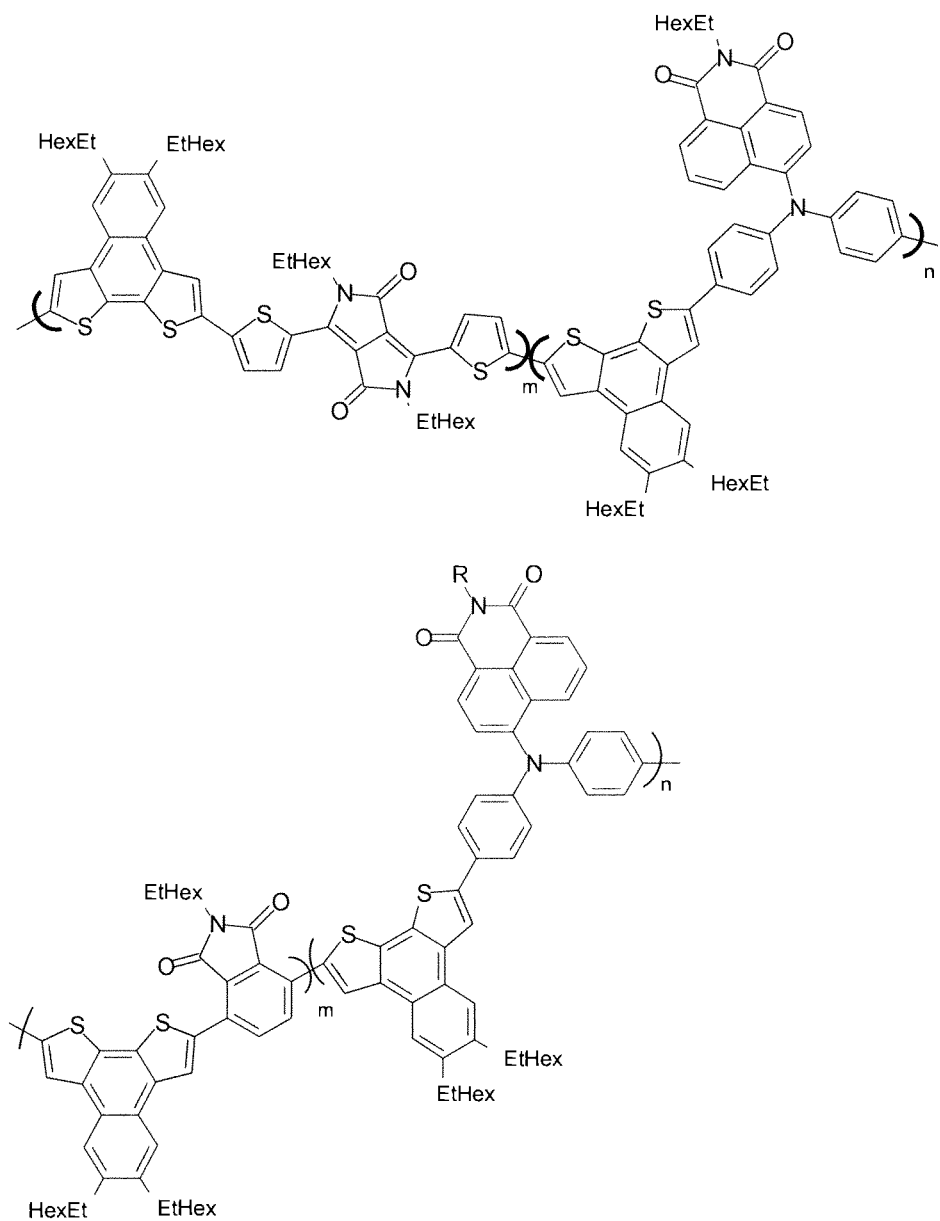

In one embodiment, the copolymer is represented by one of the structures in FIG. 6.

In one embodiment, the copolymer backbone does not comprise unfused thiophene moieties.

In one embodiment, the copolymer is soluble and has a number average molecular weight of at least 5,000.

In one embodiment, the copolymer is soluble.

In one embodiment, the copolymer has a number average molecular weight of at least 5,000 g/mol.

In one embodiment, the copolymer can be represented by at least one of the structures in Chart II:

In one embodiment, the copolymer is fluorinated.

Embodiments from 61/290,844

U.S. provisional application 61/290,844 filed Dec. 29, 2009 provides additional embodiments. These embodiments can be adapted to include benzo[2,1-b:3,4-b']dithiophene moieties.

In addition, arylamine embodiments can be provided. For example, the donor acceptor polymers can comprise nitrogen in the backbone conjugation. An example is to have an arylamine group in the backbone. The arylamine can optionally comprise carbazole or can be not a carbazole. Arylamine units can be donor moieties, although the donor or acceptor character can be tuned by the substituents on the arylamine.

Important embodiments include polymers, wherein the polymer comprises an arylamine moiety in the polymer backbone. Arylamine polymer backbones are known in the art. For example, arylamine backbone moieties, also known as arylamine repeat moieties, are described in U.S. provisional Appl. No. 61/108,851, filed Oct. 27, 2008, by Seshadri et al., entitled "Polyarylamine Ketones," and in U.S. provisional Appl. No. 61/115,877, filed Nov. 18, 2008, by Sheshadri et al., entitled "Aminobenzene Compositions," both of which are incorporated by reference in their entirety. Arylamines are also described in, for example, U.S. Pat. No. 7,166,010, patent publication WO 2003/037844, and patent publication WO 2008/032631, all of which are incorporated by reference in their entirety.

Arylamine moieties can comprise, for example, a single nitrogen atom, or can comprise multiple nitrogen atoms, including two, three, or more nitrogen atoms.

The conjugated polymer backbone can comprise nitrogen atoms without breaking the conjugation as known in the art.

The arylamine can be substituted with side groups as known in the art. In one particular embodiment, the arylamine can be substituted with at least one donor, and with at least one acceptor. In another embodiment, the arylamine can be substituted with a dye.

FIG. 16 of 61/290,844 illustrates examples of arylamine backbone moieties, which are incorporated by reference.

FIG. 17 of 61/290,844 illustrates examples of particular arylamine polymers, which are incorporated by reference.

Arylamine backbone moieties are known in the art. See, for example, Lim et al., *Organic Letters*, 2006, 8(21), 2703-4706; Fusake et al., *Polymers for Advanced Technologies*, 2002, 13, 601-604; Shirota et al., *Chem. Rev.*, 2007, 107, 953-1010; Z. Li and H. Meng, Eds., *Organic Light-Emitting Materials and Devices*, CRC Press (Taylor and Francis Group, LLC), Boca Raton (2007) and references therein. Arylamine backbone moieties can each comprise at least one nitrogen atom and at least one benzene ring, so that the polymer backbone can comprise both at least one aryl group and nitrogen atom from the arylamine. The aryl group may also appear in the side group. One or more nitrogens may appear in the side group. As a non-limiting example, an arylamine backbone moiety can comprise one benzene ring bonded to a nitrogen atom; two benzene rings bonded to a nitrogen atom; or three benzene rings bonded to a nitrogen atom.

An arylamine backbone moiety can comprise one or more aromatic groups, such as, for example, benzene, naphthalene, anthracene, and phenanthracene groups. The aromatic groups may be substituted or unsubstituted. As a non-limiting example, they can be substituted with one or more $C_1$-$C_{10}$ alkyl, perfluoroalkyl, thioalkyl, alkoxy, alkylaryl, arylalkyl, aryloxy, heteroaryl, cyano, halo, and alkythio groups, or a combination thereof.

In some embodiments, an arylamine backbone moiety may comprise N,N'-diphenyl benzidine. The N,N'-diphenyl benzidine aryl groups can be, for example, unsubstituted, or can be, for example, substituted with, as non-limiting examples, $C_1$-$C_{10}$ alkyl, perfluoroalkyl, thioalkyl, alkoxy, alkylaryl, arylalkyl, aryloxy, heteroaryl, cyano, halo, alkylthio, trialkyl silyl, trialkoxysilyl, and trialkyl silyloxy groups. Commonly, substitution of an aryl group of N,N'-diphenyl benzidine can involve one or more aryl groups that do not become part of the polymer backbone. The arylamine backbone moiety may commonly comprise N,N'-diphenyl-1,4-phenylenediamine. The N,N'-diphenyl-1,4-phenylenediamine aryl groups can be, for example, unsubstituted, or can be, for example, substituted with, as non-limiting examples, $C_1$-$C_{10}$ alkyl, perfluoroalkyl, thioalkyl, alkoxy, alkylaryl, arylalkyl, aryloxy, heteroaryl, cyano, halo, alkylthio, trialkyl silyl, trialkoxysilyl, and trialkyl silyloxy groups. Commonly, substitution of an aryl group of N,N'-diphenyl-1,4-phenylenediamine can involve one or more aryl groups that do not become part of the polymer backbone. In some embodiments, the arylamine backbone moiety can comprise a mixture of arylamine backbone moieties.

A class of polymers I can be prepared according to Scheme 1. Shemes 1, 2, and 3 shows an embodiment using benzo[2,1-b:4,5-b']dithiophene but alternatively this can be benzo[2,1-b:3,4-b']dithiophene.

(Scheme 1).

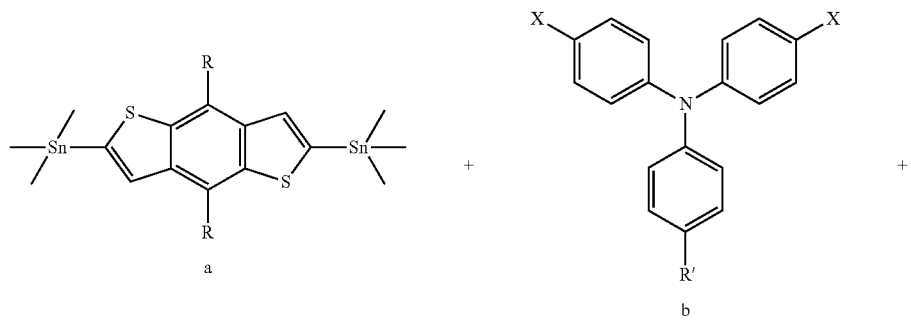

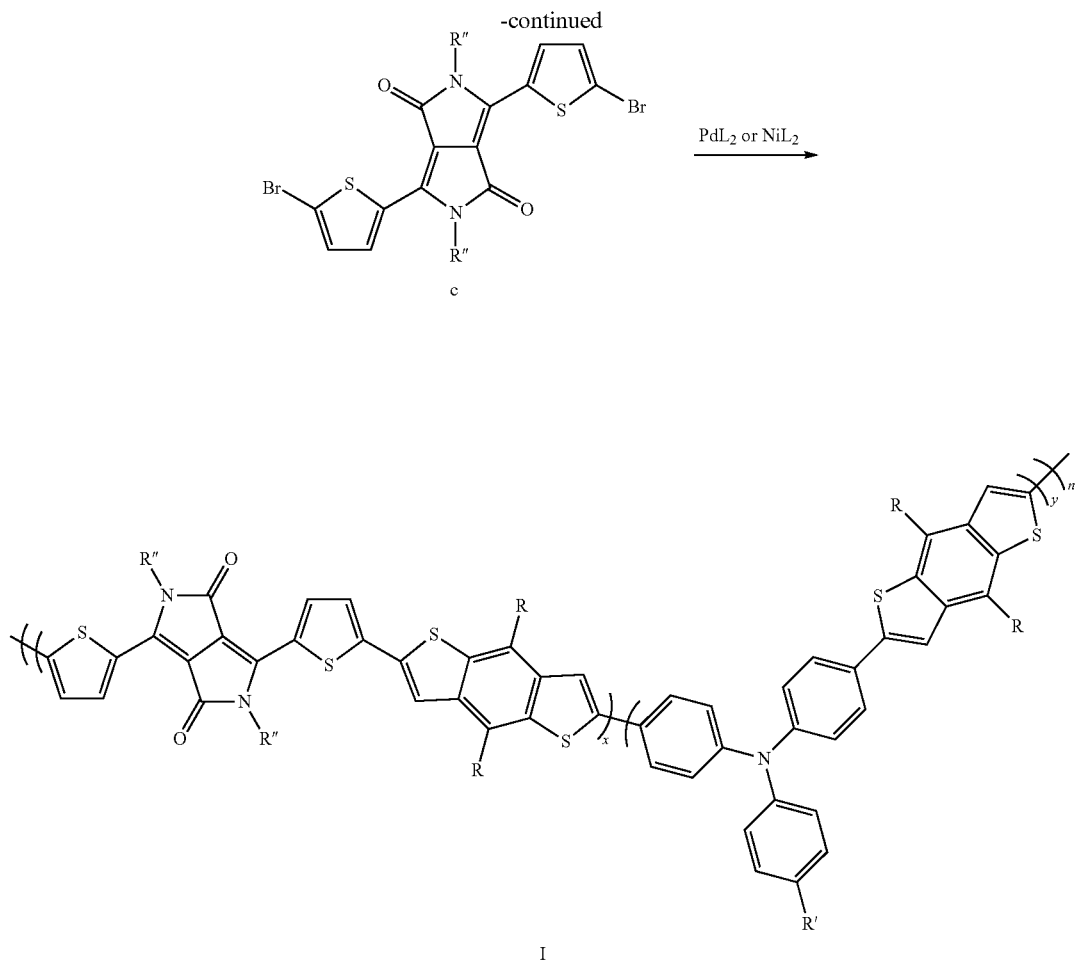

In Scheme 1, for example, a monomer (a) with two polymerizable Z groups such as, for example, Sn-bearing polymerizable groups is coupled with monomers (b) and (c), each with two halogen-bearing or pseudo-halogen-bearing polymerizable groups, to provide the product polymer represented as (I). For example, X can be I, Br, or Cl. The structure shown as (I) may not show the details of all of the polymer microstructure.

The R groups in Scheme 1, such as R, R', and R" can be solubilizing side groups selected to tune solubility and HOMO-LUMO values. Solubility can be important for improving processability and bulk heterojunction formation. R, R', and R" may individually be selected from alkyl, oligoether, perfluorinated alkyl, partially fluorinated alkyl, aryl, substituted alkyl, and the like, based on the solvents present in the ink. A pure alkyl group, such as 2-ethylhexyl, may be selected to increase solubility in such solvents as xylene, chlorbenzene, and 1,2-dichlorobenzene. Oligoether sidegroups will favor ether-based solvents and halogenated alkane solvents, such as 1,2-dichloroethane. Fluorinated side groups will similarly favor fluorinated solvents.

In some embodiments, the side groups R, R', and R" may be selected not only based on solubility, but also based on their ability to absorb visible light. Not only can this be used to increase total light absorption, but side group selection can also tune charge transport and exciton dissociation properties.

Properties of the polymer may be tuned by adjusting the relative amounts of each of the monomers incorporated in the polymer, for example, by adjusting the relative mounts of the monomers present at the start of polymerization. Further structure tuning may be achieved by adjusting the relative reaction rates of the monomers in the coupling reaction. For example, as shown for monomer (b) in Scheme 1, different halogen or pseudo-halogen species, or other reactive species, may be employed, where X may be difluoro, dichloro, diiodo, dibromo, di-trimethylsilane, bis-triflate, or a mixture of these, for example, bromo-iodo. By selecting the halogen or pseudo-halogen species accordingly, one may compensate or partially compensate for differences in the polymerization rates of the monomers due to differences in their structures. For example, if only dibromides were used for both monomers (b) and (c), the more electron deficient monomer (c) would be expected to have a higher rate for oxidative insertion into the polymer than that for monomer (b). In this case, monomer (c) would be expected to be preferentially incorporated into the chain until its concentration was sufficiently depleted to allow subsequent increased incorporate of monomer (b). By using a monomer (b) with, for example, diodo functionality, the relative rates of incorporation of the two monomers can be adjusted to depart from those expected from their relative electron deficiencies and initial concentrations alone. In addition, feed ratio of the monomers with different reactivities can be varied.

In addition, a class of polymers II may be prepared according to Scheme 2:

(Scheme 2).

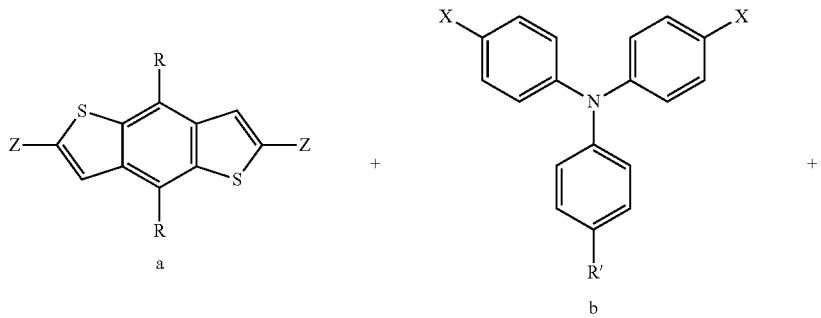

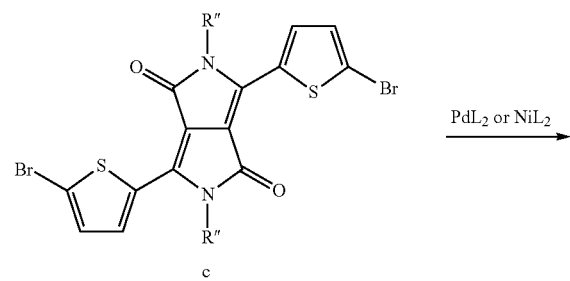

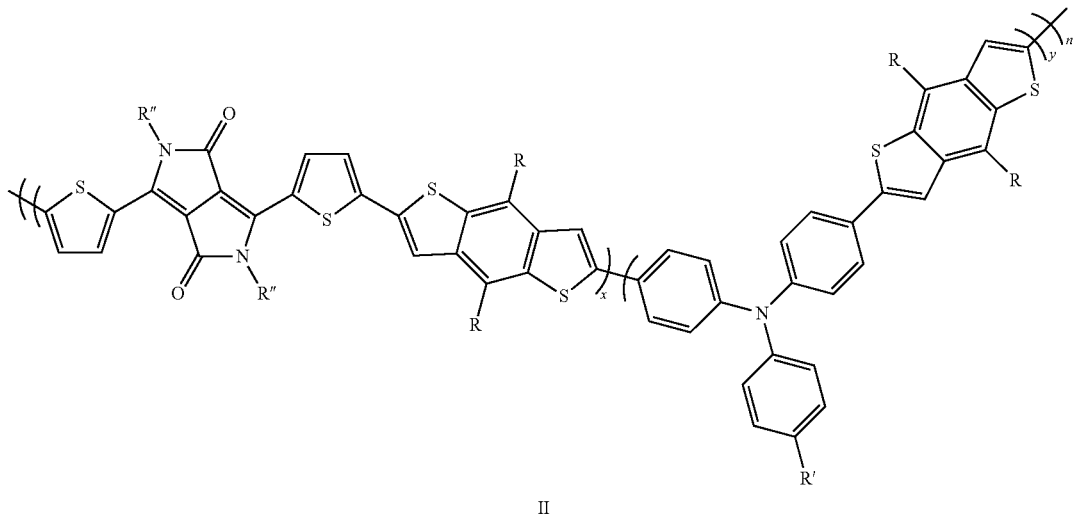

II

Scheme 2 is a generalization of Scheme 1, where monomer (a) may be activated by various groups Z. For Stille coupling, Z comprises $Sn(R)_3$, as shown in Scheme 1. Other possibilities are polymerizable groups comprising B, Si, Zn, and Mg, for use in Suzuki, bis-trimethylsilane, Negishi, and Kumada coupling, respectively. Selection of groups Z will generally depend upon a variety of factors, such as manufacturing cost, purity, relative reaction rates, and the like. For OPV applications, purity can be particularly important, to allow attainment of high number average molecular weights (Mn), preferably Mn greater than 20,000, while still maintaining polydispersity index (PDI) ranging from about 1 to 4, or about 1 to 3, preferably near 2.

A class of polymers III may be prepared according to Scheme 3:

the anode and comprising at least one p-type material and at least one n-type material, wherein the p-type material comprises at least one conjugated copolymer comprising at least one arylamine backbone moiety, and wherein the n-type material comprises at least one fullerene derivative.

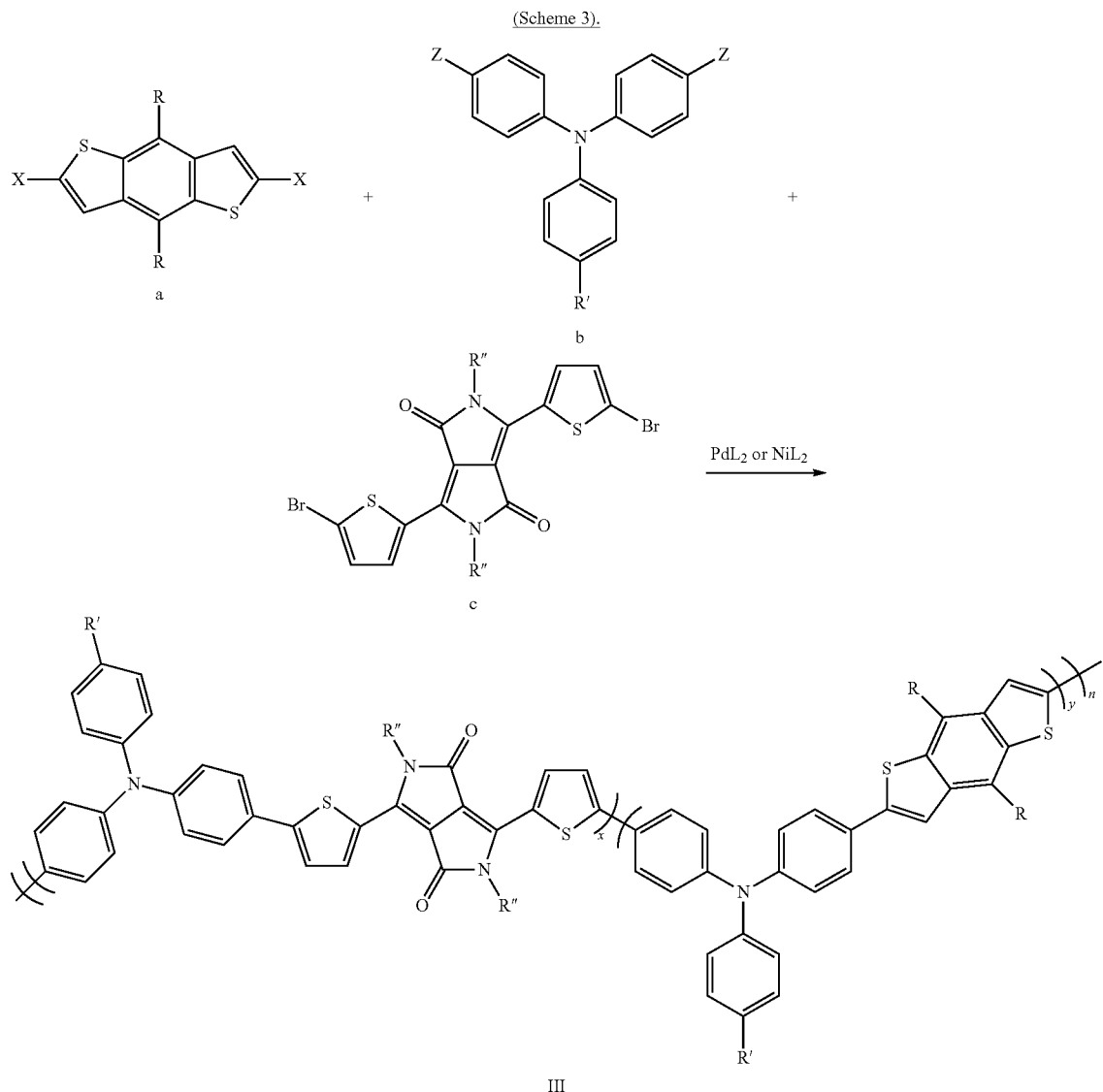

Scheme 3 is a variation of Scheme 2, where monomer (b) now comprises two polymerizable groups Z and monomer (a) now comprises two polymerizable groups bearing halogen species or pseudo-halogen species X, where Z and X are described above. Because monomer (a) may have a HOMO that is, say, 0.4 eV lower than that of monomer (b), the resulting structure of polymer III, where the arylamine moiety of monomer (b) is adjacent to the acceptor moiety of monomer (c), can have an impact on the photophysics of the polymer charge transfer excited state, charge transport, and bulk heterojunction formation.

In addition, one embodiment provides a device comprising: at least one cathode; at least one anode; and at least one photovoltaic active layer disposed between the cathode and In one embodiment, the p-type material does not comprise a carbazole moiety In one embodiment, the arylamine backbone moiety comprises one or more solubilizing groups.

In one embodiment, the copolymer has a random copolymer structure.

Embodiments from 61/289,314

U.S. provisional application 61/289,314 filed Dec. 22, 2009 provides additional embodiments. These embodiments can be adapted to including polymers, inks, and moieties comprising benzo [2,1-b:3,4-b']dithiophene units.

In some embodiments, inks may comprise one or more fluorinated solvents, or inks may comprise solvent blends that comprise one or more fluorinated solvents, or inks may comprise one or more fluorinated solvent additives.

For example, one embodiment provides a composition comprising: (i) at least one donor acceptor conjugated polymer, (ii) at least one n-type material different from the polymer, (iii) at least one solvent for the polymer, (iv) at least one fluorinated solvent additive which is different than the solvent. The donor acceptor conjugated polymer and the n-type material can form a bulk heterojunction. In some embodiments, a fluorous solvent or additive can be used in combination with a non-fluorous solvent.

The amount of the fluorinated solvent in the solvent blend, or additive, can be, for example, about 50 wt. % or less, or about 25 wt. % or less, or about 10 wt. % or less, or about 5 wt. % or less, or about 3 wt. % or less, relative to the total amount of solvent and liquid component. In some embodiments, the lower amount can be, for example, at least about 0.1 wt. %, or at least about 1 wt. % or at least about 2 wt. %. In some embodiments, the only halogenated solvent is a fluorinated solvent. In some embodiments, the solvent system comprises a halogenated solvent and a fluorinated solvent different than the halogenated solvent. In some embodiments, the solvent system can comprise a non-halogenated solvent and a fluorinated solvent. The solvent system can comprise at least two, at least three, or at least four solvents, including at least one fluorinated solvent.

Fluorinated solvents are described in, for example, *Handbook of Fluorous Chemistry*, Ed Gladysz, Curran, Horvath, Wiley, 2004, including chapters 3 and 6 on fluorinated solvents. Fluorinated solvents and materials can be also obtained from, for example, SynQuest Lab., Inc., Alachua, Fla.

Fluorinated solvents or additives can be, for example, ionic or nonionic. They can be volatile and removed from the solid material upon removal of solvent. They can be fully fluorinated, perfluorinated, or partially fluorinated. They can be liquid at room temperature and pressure. Isomeric mixtures can be used.

Fluorinated solvent additive can be, for example, an alkyl or aryl compound. Fluorinated solvent additive can be, for example, fluoroalkane, perfluoroalkane, fluoroalkene, perfluoroalkene, fluoroalkyne, or perfluoroalkyne. The fluorinated solvent additive can be, for example a benzene derivative or an alkane derivative.

Fluorinated aromatic solvents may be used as solvents or in solvent blends, or as additives. Examples of such solvents include chloropentafluorobenzene, pentafluorothiophenol (pentafluorobenenethiol), 2-chlorobenzotrifluoride, 3-chlorobenzotrifluoride, 4-chlorobenzotrifluoride, o-fluorotoluene, α,α,α-trifluorotoluene(benzotrifluoride), 2,5-dichlorobenzotrifluoride, 3,4-dichlorobenzotrifluoride, 2,4-dichlorobenzotrifluoride, pentafluorobenzene, hexafluorobenzene, octafluorotoluene, 1,3-bis(trifluoromethyl)benzene (BTFMB), 1-chloro-2,4-difluorobenzene, 1-chloro-2,5-difluorobenzene, 1,3-dichloro-2-fluorobenzene, 2,4-dichloro-1-fluorobenzene, and 2,3,4,5,6-pentafluoroaniline. Other examples include hexafluorobenzene (HFB) and octafluorotoluene (OFT). Another example is a difluoroalkane.

Other fluorinated solvents may be used as solvents or in solvent blends, or as additives. Examples of such solvents include perfluorodecalin, perfluor-1,3-dimethylcylclohexane, perfluorononane, hexadecafluoroheptane, 1,6-diidoperfluorohexane, and methoxynonafluorobutane.

The density of the fluorinated compound can be, for example, about 1.3-1.9 g/cc. The boiling point can be, for example, about 50° C. to about 300° C., or about 50° C. to about 250° C., or about 50° C. to about 200° C. about 100° C. to about 175° C.

The fluorinated solvent, solvent blend, or additive can improve the performance of an organic electronic device. For example, efficiency can be improved when the solar cell active layer is prepared with fluorinated solvent, solvent blend, or additive.

Some examples of advantages and effects of fluorinated or fluorous solvents include:

1. High density fluorous solvent can in at least some embodiments offer orthogonal segregation of species more soluble in it (either through p- or n-type that can be fluorinated to subsequently improve: (i) Miscibility (or lack of miscibility, e.g., selectively fluorinated p-types can limit undesirable intercalation with fullerenes and their non-fluorinated derivatives that can prevent recombination), (ii) Packing density, (iii) Charge transport [Lit. Ref: a) A. Facchetti et al. *Adv. Mater.* 2003, 15, 33; b) P. H. Wobkenberg et al. *Appl. Phys. Lett.* 2008, 92, 143310 (fluorine containing $C_{60}$ derivatives for high-performance electron transporting field-effect transistors and integrated circuits); c) Q. Wei et al. *Adv. Mater.* 2008, 20,2211 (Self-organized buffer layers in organic solar cells], (iv) alter energy levels (HOMO/LUMO), (v) Inter-intra-molecular interactions, (vi) Compatibility with fluoro-containing HTLs or HILs 2. A range of temperature-dependent miscibility with various organic solvents 3. Moisture repellant 4. Ambient, UV, and Environmental stability 5. Increase in OPV device lifetime In particular, a combination is to use fluorinated solvent together with thermal annealing of an OPV active layer.

Fluorinated solvent additives can be used in combination with fluorinated polymers, fluorinated n-type materials, including fluorinated fullerenes, and other fluorinated materials and solvents. Both the p-type material and the n-type material in the active layer can be fluorinated. Fluorinated fullerenes are described in, for example, Wei et al., *Adv. Mater.* 2008, 20, 2211-2216. Fluoropolymers have also been used in solar cells. See Kang et al., *Applied Physics Letters* 93, 133302 (2008). For fluorinated polymers, fluorination can be in the backbone or on a side group.

Another embodiment provides a composition comprising: (i) at least one donor acceptor conjugated polymer, (ii) at least one n-type material different from the polymer, (iii) at least one solvent for the polymer, and (iv) at least one fluorinated solvent additive which is different than the solvent.

In one embodiment, the amount of additive relative to the total amount of solvent and additive is about 10 wt. % or less. In one embodiment, the amount of additive relative to the total amount of solvent and additive is about 5 wt. % or less. In one embodiment, the amount of additive relative to the total amount of solvent and additive is about 1 wt. % to about 5 wt. %.

In one embodiment, the solvent does not comprise halogen. In one embodiment, the solvent is a benzene derivative.

In one embodiment, the additive is a non-ionic compound. In one embodiment, the additive is perfluorinated. In one embodiment, the additive is partially fluorinated.

In one embodiment, the fluorinated additive has a boiling point of about 50° C. to about 300° C. In one embodiment, the fluorinated additive has a boiling point of about 100° C. to about 175° C.

In one embodiment, the fluorinated additive is a benzene derivative. In one embodiment, the fluorinated additive is a fluorinated aromatic solvent. In one embodiment, the fluorinated additive is HFB, OFT, or BTFMB.

In one embodiment, the polymer is a fluorinated polymer. In one embodiment, the polymer comprises a fluorinated backbone. In one embodiment, the polymer comprises a fluorinated side group.

In one embodiment, the n-type material is a fullerene derivative. In one embodiment, the n-type material is a C60 or a C70 fullerene derivative. In one embodiment, the n-type material is fluorinated.

In one embodiment, the polymer is fluorinated and the n-type material is fluorinated.

In one embodiment, the weight ratio of polymer to n-type material is about 1:1 to about 1:6. In one embodiment, the weight ratio of polymer to n-type material is about 1:2 to about 1:5.

In one embodiment, the weight percentage of the combined amount of polymer and n-type material is about 0.001 to about 0.2. In one embodiment, the weight percentage of the combined amount of polymer and n-type material is about 0.003 to about 0.1.

In one embodiment, the polymer comprises at least one nitrogen in the polymer backbone. In one embodiment, the polymer comprises at least one arylamine in the polymer backbone.

In one embodiment, the polymer comprises at least one tricyclic unit comprising three fused rings.

In one embodiment, the polymer comprises at least one donor moiety comprising at least three fused rings, wherein the central ring is a benzene ring which is fused to two thiophene rings.

In one embodiment, the polymer comprises a molecular weight Mn of at least 10,000.

In one embodiment, further provided is a composition comprising: (i) at least one donor acceptor conjugated polymer adapted to function with an n-type material and function in an active layer of a solar cell, (ii) at least one n-type material different from the polymer which is adapted to function with the polymer in an active layer of a solar cell, (iii) at least one solvent for the polymer and n-type material, (iv) at least one fluorinated solvent additive which is different than the solvent and present in amounts less than the solvent, wherein the fluorinated solvent additive increases the power conversion efficiency of a solar cell device comprising an active layer fabricated from the composition, compared to a device comprising an active layer fabricated from a substantially similar composition without the solvent additive.

In one embodiment, the fluorinated solvent also increases the fill factor, the open circuit voltage, and/or the short circuit current. In one embodiment, the power conversion efficiency is increased by at least 50% with use of the fluorinated additive. In one embodiment, the power conversion efficiency is increased by at least 100% with use of the fluorinated additive. In one embodiment, the power conversion efficiency is increased by at least 150% with use of the fluorinated additive. In one embodiment, the power conversion efficiency is at least 4% with use of the fluorinated additive. In one embodiment, the power conversion efficiency is at least 5% with use of the fluorinated additive. In one embodiment, the power conversion efficiency is at least 6% with use of the fluorinated additive. In one embodiment, the open circuit voltage is at least 0.7 V with use of the fluorinated additive. In one embodiment, the open circuit voltage is at least 0.8 V with use of the fluorinated additive. In one embodiment, the short circuit current is at least 10 mA/cm² with use of the fluorinated additive. In one embodiment, the short circuit current is at least 11 mA/cm² with use of the fluorinated additive. In one embodiment, the fill factor is at least 40% with use of the fluorinated additive. In one embodiment, the fill factor is at least 50% with use of the fluorinated additive.

In one embodiment, the amount of additive relative to the total amount of solvent and additive is about 5 wt. % or less. In one embodiment, the amount of additive relative to the total amount of solvent and additive is about 1 wt. % to about 5 wt. %.

In one embodiment, the solvent does not comprise halogen.

In one embodiment, the solvent is a benzene derivative.

In one embodiment, the additive is a non-ionic compound. In one embodiment, the additive is perfluorinated. In one embodiment, the additive is partially fluorinated. In one embodiment, the fluorinated additive has a boiling point of about 50° C. to about 300° C. In one embodiment, the fluorinated additive has a boiling point of about 100° C. to about 175° C.

In one embodiment, the fluorinated additive is a benzene derivative or an alkane derivative.

In one embodiment, the fluorinated additive is a fluorinated aromatic solvent.

In one embodiment, the polymer is a fluorinated polymer.

In one embodiment, the n-type material is a fullerene derivative. In one embodiment, the n-type material is fluorinated.

In one embodiment, the weight ratio of polymer to n-type material is about 1:1 to about 1:6. In one embodiment, the weight percentage of the combined amount of polymer and n-type material is about 0.001 to about 0.2.

Another embodiment provides a composition comprising: (i) at least one donor acceptor conjugated polymer, wherein the polymer comprises a backbone moiety represented by (XI):

(XI)

(ii) at least one n-type material different from the polymer, (iii) at least one solvent for the polymer, and (iv) at least one fluorinated solvent additive which is different than the solvent.

In one embodiment, the polymer is soluble.

In one embodiment, the R group is adapted to provide the polymer with solubility.

In one embodiment, R comprises optionally substituted alkyl, optionally substituted linear alkyl, optionally substituted branched alkyl, optionally substituted aryl, optionally substituted alkylaryl, optionally substituted arylalkyl, optionally substituted alkoxy, or optionally substituted aryloxy, and optionally, wherein R further comprises fluorine.

In one embodiment, the moiety (XI) is part of moiety:

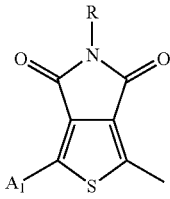

wherein A1 comprises a thiophene ring linked to (XI) at the two or five position of the thiophene ring.

In one embodiment, the moiety (XI) is part of moiety:

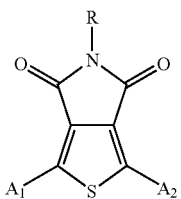

wherein both A1 and A2 comprise thiophene ring linked to (XI) at the two or five position of the thiophene ring.

In one embodiment, the polymer is a random copolymer. In one embodiment, the polymer is an alternating copolymer.

In one embodiment, the polymer comprises a donor-acceptor structure, but does not comprise equal amounts of donor and acceptor.

In one embodiment, the polymer comprises a donor-acceptor structure comprising units D1, D2, A1, and/or A2 and is represented by at least one of the following structures in Chart I.

In another embodiment, provided is a composition comprising: (i) at least one donor acceptor conjugated polymer, wherein the polymer comprises a backbone moiety represented by (VIII):

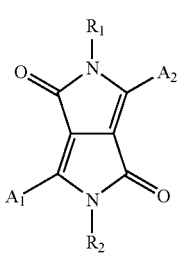

wherein A1 and A2 each independently comprise a fused ring system comprising at least two fused rings directly covalently linked to the substructure of VIII represented as substructure IX:

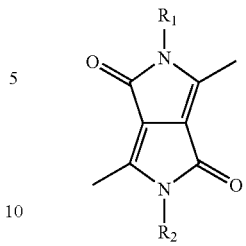

(ii) at least one n-type material different from the polymer, (iii) at least one solvent for the polymer, and (iv) at least one fluorinated solvent additive which is different than the solvent.

In one embodiment, the acceptor moiety comprises structure (VIII).

In one embodiment, the polymer is soluble.

In one embodiment, the R groups R1 and R2 are adapted to provide the polymer with solubility.

In one embodiment, R groups R1 and R2 each comprise optionally substituted alkyl, optionally substituted linear alkyl, optionally substituted branched alkyl, optionally substituted cycloalkyl, optionally substituted aryl, optionally substituted alkylaryl, optionally substituted arylalkyl, optionally substituted alkoxy, or optionally substituted aryloxy, and optionally, wherein R groups R1 and R2 further comprises fluorine.

In one embodiment, R1 and R2 are the same, and wherein A1 and A2 are the same.

In one embodiment, the fused ring systems comprise at least one thiophene fused ring, wherein the thiophene ring is directly linked to the substructure IX.

In one embodiment, the polymer is a random copolymer. In one embodiment, the polymer is an alternating copolymer.

In one embodiment, the polymer does not comprise equal amounts of donor and acceptor.

Another embodiment provides a composition comprising: (i) at least one donor acceptor conjugated polymer, wherein the polymer is a regular alternating conjugated copolymer comprising at least three backbone donor and acceptor moieties, said moieties comprising at least one donor moiety, at least one acceptor moiety, and at least one additional different donor or acceptor moiety, (ii) at least one n-type material different from the polymer, (iii) at least one solvent for the polymer, (iv) at least one fluorinated solvent additive which is different than the solvent.

In one embodiment, the moieties comprise at least two different donor moieties. In one embodiment, the moieties comprise at least two different acceptor moieties.

In one embodiment, the polymer is a soluble polymer. In one embodiment, the polymer has a number average molecular weight of at least 5,000 g/mol.

In one embodiment, the polymer does not comprise an unfused heterocyclic ring in the backbone. In one embodiment, the polymer does not comprise an unfused thiophene ring in the backbone.

In one embodiment, the polymer is prepared by copolymerization of two different monomers, wherein at least one monomer comprises both a donor and an acceptor, and the second monomer comprises a donor or an acceptor.

In one embodiment, the polymer comprises at least one nitrogen atom in the backbone.

In one embodiment, the polymer is a fluorinated polymer.

In one embodiment, a composition is provided comprising: (i) at least one donor acceptor conjugated polymer, wherein the polymer comprises a polymer backbone comprising nitrogen, (ii) at least one n-type material different from the polymer, (iii) at least one solvent for the polymer, (iv) at least one fluorinated solvent additive which is different than the solvent.

In one embodiment, the polymer comprises a polymer backbone comprising at least one arylamine moiety.

In one embodiment, the polymer comprises a polymer backbone comprising at least one arylamine moiety comprising at least two nitrogen atoms.

In one embodiment, the polymer comprises an arylamine moiety which is substituted with both an acceptor and a donor. In one embodiment, the polymer comprises an arylamine moiety which is substituted with a dye.

In one embodiment, the polymer is soluble.

In one embodiment, the polymer has a number average molecular weight of at least 5,000 g/mol.

In one embodiment, the polymer backbone nitrogen atom is not part of a carbazole moiety.

In one embodiment, coated substrates are prepared by depositing compositions according to embodiments described herein including fluorinated solvent embodiments.

In one embodiment, solar cell devices are prepared by depositing compositions according to embodiments described herein, including fluorinated solvent embodiments, to form active layers.

Another embodiment provides a composition comprising: (i) at least polymer, (ii) at least one n-type material different from the polymer, (iii) at least one solvent for the polymer, (iv) at least one fluorinated solvent additive which is different than the solvent.

In one embodiment, the polymer is a conjugated polymer. In one embodiment, the polymer is a donor-acceptor conjugated polymer. In one embodiment, the polymer is a polythiophene polymer.

In one embodiment, the polymer is a fluorinated polymer.

In one embodiment, provided is a use of a fluorinated solvent additive to improve efficiency of a solar cell device.

Part II

Further Embodiments and Applications

Uses of Polymers

The materials, including monomers, dimers, trimers, oligomers, polymers, and copolymers described herein in Part I, the working examples, and claims, can be used in organic electronic devices including, for example, OLEDs, OPVs including as OPV active layer, transistors, OFETs, batteries, and printed electronics generally, as well as sensors. The methods described in Part II can be adapted for the particular compounds and polymers being used.

For example, photovoltaic cells (solar cells) are known in the art. See, for example, Sun and Sariciftci, *Organic Photovoltaics, Mechanisms, Materials, and Devices,* 2005. The photovoltaic cell can comprise an active layer comprising a composition comprising at least one p-type material and at least one n-type material. One can engineer HOMO, LUMO, and band gaps for the p- and n-type materials for good performance. The morphology of the active layer can be adapted to provide good performance. For example, a nanoscale morphology can be prepared. An example is a bulk heterojunction.

The photovoltaic device can comprise at least one cathode, at least one anode, and at least one photovoltaic active layer disposed between the cathode and anode. The active layer can comprise a p-type material and an n-type material.

In an OPV active layer, the polymers described herein, which can be a p-type material, can be combined with n-type materials or acceptor moieties, such as, for example, fullerenes and fullerene derivatives. An example of a fullerene derivative is PCBM. Fullerenes can be also derivatized, for example, as described in PCT Patent Publication WO 2008/018931 filed May 2, 2007 and US Patent Publication 2008/0319207 published Dec. 25, 2008, both to Laird, et al. (Plextronics, Inc.). Other types of n-type materials known in the art can be used. If desired, larger area photovoltaics can be fabricated. See, for example, Bundgaard et al., *Solar Energy Materials and Solar Cells,* 2007, 91, 1019-1025.

Polymer solar cells, including polymer fullerene solar cells, are described in, for example, Hoppe et al., *Adv. Polym. Sci.* (2008), 214: 1-86; Zhu et al., "Design Rules for Efficient Organic Solar Cells," Chapter 13, 195-222 in *High-Efficient Low-Cost Photovoltaics,* Springer, 2009.

OLED devices are known in the art including white OLEDs, or WOLEDs. See, for example, Li and Meng, *Organic Light Emitting Materials and Devices,* CRC Taylor, 2006 and US Patent Publication 2006/0078761 published Apr. 13, 2006. The devices can comprise, for example, multilayer structures including, for example, an anode, including a transparent conductor, such as a transparent conductive oxide (TCO) on glass or PET or PEN; a hole injection layer; an electroluminescent layer, such as a polymer layer; a conditioning layer, such as LiF, and a cathode, such as for example Ca, Al, or Ba.

Methods known in the art can be used to fabricate organic electronic devices including for example OLED devices. Methods known in the art can be used to measure brightness, efficiency, and lifetimes. OLED patents include for example U.S. Pat. Nos. 4,356,429 and 4,539,507 (Kodak). Conducting polymers which emit light are described in for example U.S. Pat. Nos. 5,247,190 and 5,401,827 (Cambridge Display Technologies). See also Kraft et al., "Electroluminescent Conjugated Polymers—Seeing Polymers in a New Light," *Angew. Chem. Int. Ed.,* 1998, 37, 402-428, including device architecture, physical principles, solution processing, multilayering, blends, and materials synthesis and formulation, which is hereby incorporated by reference in its entirety.

In addition, printed electronics are generally known in the art. See, for example, *Printed Organic and Molecular Electronics,* Ed. D. Gamota et al., 2004. For example, Chapters 1 and 2 describe organic semiconductors, Chapter 3 describes manufacturing platforms for printing circuits, Chapter 4 describes electrical behavior of transistors and circuits, Chapter 5 describes applications, and Chapter 6 describes molecular electronics. See also Pope et al., *Electronic Processes in Organic Crystals and Polymers,* 1999.

Solutions and Ink Formulations

The materials, polymers, and copolymers can be put into solution or dispersion form, including ink formulations, for further processing, adapting to the particular application at hand including electronic devices, such as, OLED, solar cells and active layers of solar cells.

Lower cost electronic devices can be enabled because polymers, such as those described herein, can be processed into inks which can then be handled in the same manner as inks in conventional printing processes. Ink compositions used for forming, for example, the active layer of an organic photovoltaic device can be made by dissolving p-type and n-type materials in a solvent system, optionally containing other additives.

The solvents and conjugated polymer inks can be formulated or adapted for use in a particular application such as a solar cell that may include additional additives, such as electron acceptors. The additive(s) and solvents can be adapted to provide good dispersability of the n- and p-type materials, solubility of the n- and p-type materials, and stability of the ink formulation. For example, solvents can be used which provide good solubility or dispersability for fullerenes or fullerene derivative n-type compounds. Solvents can be adapted to be environmentally friendly in view of regulations, and can be, for example, halogen free. In other embodiments, additives can be included in the ink that can improve the final film morphology or other properties. For example, solvent additives disclosed in US Patent Publication entitled "Processing Additives for Fabricating Organic Photovoltaic Cells" 2009/0108255 to Bazan et al., published on Apr. 30, 2009 can be included.

Solvent(s) and solvent additive(s) can be removed from the ink compositions, and films can be formed. Solid films can be formed that either comprise solvent(s) and solvent additive(s), are substantially free of solvent(s) and solvent additive(s), or are free of solvent(s) and solvent additive(s). For example, the amount of remaining solvent can be less than about 5% by weight, or less than about 1% by weight, or less than about 0.1% by weight. For example, the amount of remaining solvent additive can be less than about 5% by weight, or less than about 1% by weight, or less than about 0.1% by weight.

Conventional methods can be used to cast polymer materials from the compositions to provide solid forms, including thin film forms and printed forms. For example, the p-type and n-type materials of the active layer can be dissolved in the solvent to form an ink, and then allowed to dry. Suitable coating methods are known. These include roll-to-roll coating, screen printing, spin casting, spin coating, doctor blading, dip coating, spray coating, or ink jet printing, and other known coating and printing methods.

Ink Components

Ink components known in the art can be used including, for example, solvents and n-type materials. The amounts of the components can be adapted to improve performance.

N-Type Materials

The active layer composition in, for example, a solar cell may include an n-type component or electron acceptor, or an electron acceptor moiety. These can be materials with a strong electron affinity and good electron accepting character. The n-type component should provide fast transfer, good stability, and good processability. The n-type material is desirably soluble in, dispersible in, or otherwise miscible with the solvents in order to provide for solution processing. The n-type component may take the form of particles, including microparticles and nanoparticles, inorganic particles, organic particles, and/or semiconductor particles. Examples of n-type components include fullerene and non-fullerene compounds. N-type materials can be small molecules, oligomers, or polymers, including conjugated polymers.

For example, the active layer can comprise an n-type material comprising at least one fullerene structure. Fullerenes are known in the art. Fullerenes can be described as spheroidal carbon compounds. For example, the fullerene surface can present [6,6] bonding and [6,5] bonding as known in the art. The fullerene can have a surface comprising six-membered and five-membered rings. Fullerenes can be for example C60, C70, or C84, and additional carbon atoms can be added via derivative groups. See for example Hirsch, A.; Brettreich, M., *Fullerenes: Chemistry and Reactions*, Wiley-VCH Verlag, Weinheim, 2005, which is hereby incorporated by reference including teachings for fullerene nomenclature and synthesis, derivatization, reduction reactions (Chapter 2), nucleophilic additions (Chapter 3), cycloadditions (Chapter 4), hydrogenation (Chapter 5), radical additions (Chapter 6), transition metal complex formation (Chapter 7), oxidation and reactions with electrophiles (Chapter 8), halogenation (Chapter 9), regiochemistry (Chapter 10), cluster modification (Chapter 11), heterofullerenes (Chapter 12), and higher fullerenes (Chapter 13). Methods described herein can be used to synthesize fullerene derivatives and adducts.

In particular, the active layer can comprise at least one n-type material, wherein the n-type material comprises at least one derivatized fullerene or fullerene derivative. The derivative compound can be for example an adduct. The terms "derivatized fullerene," "fullerene derivative" as used herein, can be used interchangeably and can be, for example, fullerenes comprising, from 1 to 84, or 1 to 70, or 1 to 60, from 1 to 20, from 1 to 18, from one to ten, or from one to six, or from one to five, or from one to three substituents each covalently bonded to, for example, one or two carbons in the spheroidal carbon compounds. The derivatized fullerene can comprise a fullerene covalently bonded by [4+2] cycloaddition to at least one derivative moiety, R.

An example of an n-type material is PCBM.

Examples of n-type materials are described in, for example, International Patent Publication No. WO/2008/018931 published on Feb. 14, 2008 and US Patent Publication 2008/0319207 published Dec. 25, 2008, both to Laird, et al.

Solvent

The solvents useful for the presently claimed inventions can include, for example, halogenated benzenes, alkyl benzenes, halogenated methane, and thiophenes derivatives, and the like. More specifically, solvent can be for example chlorobenzene, dichlorobenzene, xylenes, toluene, chloroform, 3-methylthiophene, 3-propylthiphene, 3-hexylthiphene, and mixtures thereof. At least two solvents can be used. Solvents can be polymer solvent such as, for example, NMP.

The solvent system can include at least two solvents, at least one first solvent and at least one second solvent (e.g., a solvent additive), which are different from each other. They can be organic solvents. Particularly useful solvent systems can be used as described in co-pending US patent application entitled "Solvent System for Conjugated Polymers," Ser. No. 12/113,058 filed on May 2, 2007, to Sheina et al., and co-pending US patent application entitled "Improved Solvent System," Ser. No. 12/541,500 filed Aug. 14, 2009, which are hereby incorporated by reference in their entirety.

The solvent or solvents can be one or more fluorinated solvents which are different from the fluorinated additives described below. Examples include aromatic fluorinated solvents such as, for example, 2-chlorobenzotrifluoride or 4-chlorobenzotrifluoride.

Solvents can be heated, if desired, to improve the solubility of the polymer in the solvent and/or melt the solvent. For example, solvents can be heated to 60° C. or 100° C.

Solvent Additives

Solvent additives can be used, wherein a relatively small addition of a component (e.g, 1-3 wt %) can have a large impact on performance. For example, a primary or first solvent can be used in conjunction with a solvent additive. Solvent additives can be volatile and can be removed upon solvent removal. Or solvent additives can be less volatile and stay in the film upon solvent removal.

Different examples exist for solvent additives. For example, a solvent additive can comprise at least one heterocyclic ring. The heterocyclic ring can be, for example, at least one thiophene ring. The second solvent can be for example an alkylthiophene. In some instances the heterocyclic ring is not a nitrogen-containing ring. Or it can be a nitrogen containing ring. Thus, in some embodiments the second solvent is or is not a pyridine, pyrazine, pyrimidine, or a pyrrolidinone. In some embodiments, the heterocyclic ring includes at least one S atom and at least one O atom. Examples of suitable solvent additives include, but are not limited to, thiophene derivatives (i.e., substituted thiophenes). The thiophene ring may be substituted or unsubstituted in different positions on the ring. However, in some instances the thiophene derivatives do not contain halogen atoms. Alkylthiophenes and combinations thereof may be used as the second solvent. The alkyl group can be, for example, C1, C2, C3, C4, and the like up to and including C8, C12, C16, and C20. The alkyl group can be linear or branched. Specific examples of suitable alkylthiophenes include methylthiophene, ethylthiophene, propylthiophene, butylthiophene, pentylthiophene, hexylthiophene, heptylthiophene, octylthiophene, nonylthiophene, and decylthiophene.

Other examples of solvent systems can be used as described in the aforementioned co-pending US patent applications, in US Patent Publication entitled "Processing Additives for Fabricating Organic Photovoltaic Cells" 2009/0108255 to Bazan et al., published on Apr. 30, 2009 or in Peet, et al., "Efficiency enhancement in low-bandgap polymer solar cells by processing with alkane dithiols," *Nat. Mater.*, 2007, 6, 497-500.

Device Preparation

Devices can be made comprising one or more layers comprising the polymers described herein and one or more electrodes, including anode and cathode. Layers can be built up on a substrate. See, for example, Chen et al., *Advanced Materials*, 2009, 21, 1-16.

Devices using the presently claimed inventions can be made using for example ITO as an anode material on a substrate. Other anode materials can include for example metals, such as Au, carbon nanotubes, single or multiwalled, and other transparent conducting oxides. The resistivity of the anode can be maintained below, for example, 15 Ω/sq or less, 25 or less, 50 or less, or 100 or less, or 200 or less, or 250 or less. The substrate can be rigid or flexible and can be, for example, glass, plastics (PTFE, polysiloxanes, thermoplastics, PET, PEN and the like), metals (Al, Au, Ag), metal foils, metal oxides, (TiOx, ZnOx) and semiconductors, such as Si. The ITO on the substrate can be cleaned using techniques known in the art prior to device layer deposition.

A variety of layers can be included between the anode and the active layer of a solar cell or the emissive layer of an OLED. These layers are generally referred to as hole transport layer (HTL), hole injection layers (HIL), hole collection (HCL), electron blocking layers (EBL) and/or interlayers.

Various kinds of hole transport layers, hole injection layers, hole collection layers, and/or hole extraction layers can be used. For example, hole transport layers of various kinds are described in the following references: 1) U.S. Pat. No. 7,569,159, issued Aug. 4, 2009 to Hammond et al.; U.S. Ser. No. 11/826,394, filed Jul. 13, 2007, published Oct. 9, 2008 as 2008/0248313; U.S. Ser. No. 12/422,159, filed Apr. 9, 2009; U.S. Ser. No. 61/108,851, filed Oct. 27, 2008; and U.S. Ser. No. 61/115,877, filed Nov. 18, 2008.

Hole transport layers (HTL) can be added using, for example, spin casting, ink jetting, doctor blading, spray casting, dip coating, vapor depositing, or any other known deposition method.

The HTLs can be formed as films from, for example, PEDOT, PEDOT/PSS or TBD, or NPB, or PLEXCORE® OC inks (Plextronics, Pittsburgh, Pa.).

The thickness of the HTL or HIL layer can be for example from about 10 nm to about 300 nm thick, or from 30 nm to 60 nm, 60 nm to 100 nm, or 100 nm to 200 nm. The film then can be optionally dried/annealed at, for example, 50 to 200° C., or at 80 to 200° C., or at 110 to 200° C. for 1 min to an hour, optionally in an inert atmosphere.

Active layer thickness can be, for example, about 50 nm to about 250 nm, including for an OPV device.

The active layer can be formulated from a mixture of n-type and p-type materials. The n- and p-type materials can be mixed in a ratio of for example from about 0.1 to 4.0 (p-type) to about 1 (n-type) based on a weight, or from about 1.1 to about 3.0 (p-type) to about 1 (n-type) or from about 1.1 to about 1.5 (p-type) to about 1 (n-type). The amount of each type of material or the ratio between the two types of components can be varied for the particular application.

The active layer can be then deposited by spin casting, ink jetting, doctor blading, spray casting, dip coating, vapor depositing, or any other known deposition method, on top of the HTL or HIL film. The film is then optionally thermally annealed at, for example, about 40 to about 250° C., or from about 150 to 180° C., for about 10 min to an hour in an inert atmosphere. Solvent annealing can be also carried out as needed.

A cathode layer can be added to the device, generally using for example thermal evaporation of one or more metals. For example, a 1 to 15 nm Ca layer is thermally evaporated onto the active layer through a shadow mask, followed by deposition of a 10 to 300 nm Al layer.

A variety of layers can be included between the cathode and the active layer of a solar cell or the emissive layer of an OLED. These layers are generally referred to as electron transport layers (ETL), electron injection layers (EIL), hole blocking layers (HBL) and/or interlayers.

In some embodiments, an optional interlayer may be included between the active layer and the cathode, and/or between the HTL or HIL and the active layer. This interlayer can be, for example, from 0.5 nm to about 100 nm, or from about 1 to 3 nm, thick. The interlayer can comprise an electron conditioning, a hole blocking, or an extraction material, such as LiF, BCP, bathocuprine, fullerenes or fullerene derivatives, such as C60, C70, C84 and other fullerenes and fullerene derivatives discussed herein.

Electron transport layers can be used in, for example, solar cell devices. See, for example, U.S. patent application No. 61/116,963 filed Nov. 21, 2008.

The devices can be then encapsulated using a glass cover slip sealed with a curable glue, or in other epoxy or plastic coatings. Cavity glass with a getter/desiccant may also be used.

In addition, the active layer can comprise additional ingredients including for example surfactants, dispersants, oxygen and water scavengers.

The active layer can comprise multiple layers or be multi-layered.

The active layer composition can be formed from an ink comprising a mixture as a film.

Films and devices can be annealed before use and testing. Thermal annealing and solvent annealing can be carried out.

Inverted solar cells can be made. See, for example, Chen et al. *Advanced Materials*, 2009, 21, 1-16. Tandem solar cells can be made.

Device Testing

Known solar cell parameters can be measured including for example $J_{SC}$ (mA/cm²) and Voc (V) and fill factor (FF) and power conversion efficiency (%, PCE) by methods known in the art. See for example Hoppe article cited above and references cited therein.

Oriel Solar Simulators can be used to determine PV properties including for example FF, Jsc, Voc, and efficiencies. The simulator can be calibrated by methods known in the art including for example calibration with a KG5-Si reference cell. External quantum efficiency (EQE) can be measured. Other properties for the inks, films, and devices can be measured by methods known in the art.

Power conversion efficiency (PCE) can be, for example, at least about 1%, or at least about 2%, or at least about 3%, or at least about 4%, or at least about 5%, or at least about 6%, or at least about 7%, or at least about 8%, or higher.

Fill factor, which can be expressed as a number between 0 and 1, or a percentage between 0 and 100%, can be, for example, at least about 0.4 (40%), or at least about 0.5 (50%), or at least about 0.6, or at least about 0.7, or at least about 0.8, or at least about 0.9 or higher.

Open circuit voltage ($V_{OC}$) in V can be, for example, at least about 0.3, or at least about 0.4, or at least about 0.5, or at least about 0.6 V, or at least about 0.7 V, or at least about 0.8 V, or at least about 0.9 V, or at least about 1.0 V, or at least about 1.1 V or higher. An upper limit can be, for example, about 2.0 V, or about 1.5 V, or about 1.3 V.

Short circuit current ($J_{sc}$) can be, for example, at least about 0.5, or at least about 0.6, or at least about 0.7, or at least about 0.8, or at least about 0.9, or at least about 1.0, or at least about 2.0, or at least about 3.0, or at least about 4.0, or at least about 5.0, or higher (mA/cm²).

Additional Embodiments

Inks, Solutions, and Devices

Inks, solutions, and devices are prepared and tested by methods described herein and in U.S. Provisional application Ser. No. 61/240,137 filed Sep. 4, 2009 to Sheina et al.; U.S. Provisional application Ser. No. 61/241,813 filed Sep. 11, 2009 to Brown et al.; and U.S. Provisional application Ser. No. 61/248,335 filed Oct. 2, 2009 to Brown et al., which are hereby incorporated by reference in their entirety.

Polymer solar cells, including inverted solar cells, are described in, for example, Chen et al., *Advanced Materials*, 2009, 21, 1434-1449; and Yang et al., *Advanced Functional Materials*, 2009, 19, 1227-1234. Film morphology can be controlled.

Use of additives is described in, for example, US Patent Publication 2009/0108255 and 2008/0315187. See also, Peet et al., *Nature Materials*, vol. 6, July 2007, 497-500 and supplemental information; Lee et al., *J. Am. Chem. Soc.*, 2008, 130, 3619-3623; Coates et al., *Applied Physics Letters*, 93, 072105 (2008); Cho et al., *Organic Electronics*, 9 (2008), 1107-1111; Hwang et al., *J. Appl. Physics*, 104, 033706 (2008); Xu et al., *Adv. Functional Mat.*, 2009, 19, 1227-1234; Chen et al., *Adv. Materials*, 2009, 21, 1434-1449.

Part III

Working Examples

In addition to the description provided above, the following non-limiting examples are provided.

Monomer Preparations

Example 1

Synthesis of Monomers Used to Produce benzo[2,1-b:3,4-b']dithiophene

Example 1a

Synthesis of 1,2-bis(2-ethylhexyl)benzene

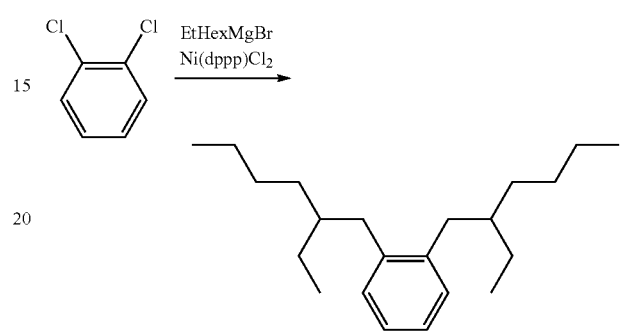

A dry 2 L 3-neck flask with attached reflux condenser and addition funnel, flushed with dry nitrogen, was charged with 1,2-dichlorobenzene (79.4 g, 540 mmol), Ni(dppp)Cl₂ (3 g, 6 mmol), and 200 mL of dry Et₂O. The addition funnel was charged with 2-ethylhexylmagnesium bromide (3M, 400 mL). The solution was cooled to 5° C. and the Grignard reagent was added dropwise to the reaction. After complete addition, the reaction was stirred at 5° C. for 30 min and then warmed to room temperature (RT). The reaction was then heated to reflux for 12 h. After cooling to RT, the reaction mixture was poured onto an ice/HCl (10%) solution and extracted with MTBE. The organic fractions were dried over anhydrous MgSO₄ and then concentrated. The product was purified first by distillation followed by column chromatography with hexanes, and isolated as colorless oil (101 g, 62%).

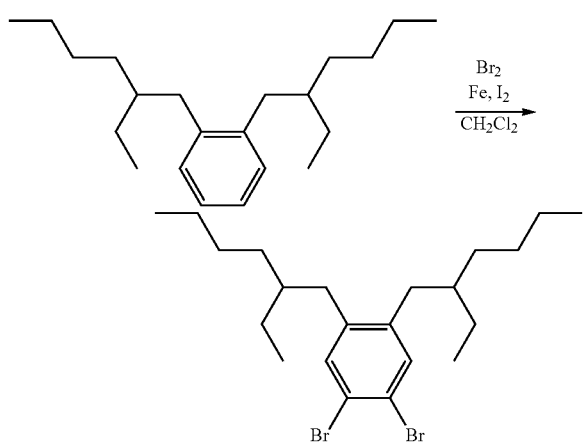

Example 1b

Synthesis of 1,2-dibromo-4,5-bis(2-ethylhexyl)benzene

A 1 L flask with attached reflux condenser and addition funnel was charged with 1,2-bis(2-ethylhexyl)benzene (51 g, 169 mmol) and CH$_2$Cl$_2$ (170 mL). Iron powder (500 mg) and I$_2$ (500 mg) were added and the addition funnel was charged with bromine (56.6 g, 354 mmol). The solution was cooled to 5° C. and the bromine was added dropwise under a gentle nitrogen stream. After the addition was complete, the reaction was allowed to warm to RT for 12 h. The reaction mixture was poured onto an ice water solution with sodium thiosulfate and extracted with chloroform (3×500 mL). The organic fractions were dried over anhydrous MgSO$_4$ and concentrated. The product was purified by column chromatography with hexanes and isolated as pale yellow oil (72 g, 93%). GC/MS and NMR data were consistent with literature examples.

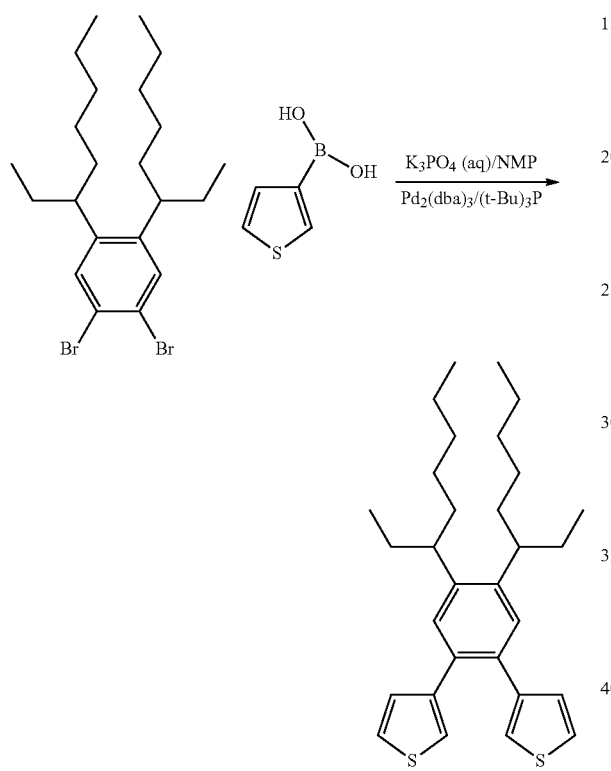

Example 1c

Synthesis of 3,3'-(4,5-di(octan-3-yl)-1,2-phenylene) dithiophene

A 500 ml 3 neck round bottom flask with attached reflux condenser and addition funnel was charged with 1,2-dibromo-4,5-bis(2-ethylhexyl)benzene (20.0 g, 0.0434 mol) and thiophen-3-ylboronic acid (2.5 eq., 12.2 g, 0.096 mol). The reaction flask was flushed with dry argon and 90 mL of deoxygenated NMP and a deoxygenated 1.9 M solution of K$_3$PO$_4$ in water (4 eq., 92 mL) were added via syringe and cannula, respectively. The reaction mixture was evacuated and refilled with argon five times, followed by additional purging with argon for 30 min. Tris(dibenzylideneacetone) dipalladium (0) (1.99 g, 5 mol %) and tri-tertbutylphosphine (0.3 eq., 2.63 g, 0.0130 mmol) in 10 mL deoxygenated NMP were added to the reaction flask via syringe. The reaction mixture was evacuated and refilled with argon five times. The reaction flask was immersed into a oil bath which was preheated to 80° C. and left stirring under an argon stream for 12 h. The reaction was analyzed by GC-MS and another portion of catalyst/ligand mixture was added. The reaction was continued for another 6 h and then cooled to RT. The reaction mixture was poured water and extracted with MTBE. The organic fractions were dried over anhydrous MgSO$_4$ and then concentrated. The product was purified by column chromatography with hexanes and isolated as colorless oil (7.34 g, 37%).

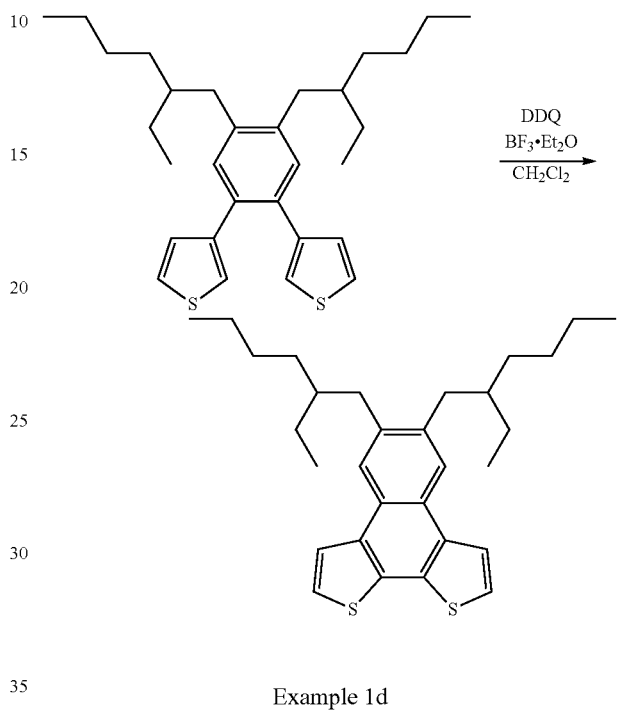

Example 1d

Synthesis of 5,6-bis(2-ethylhexyl)naphtho[2,1-b:3,4-b']dithiophene

A dry 500 mL 3-neck flask, flushed with dry nitrogen, was charged with 5 g (10.7 mmol) of 3,3'-(4,5-bis(2-ethylhexyl)-1,2-phenylene)dithiophene. The flask was evacuated and backfilled with nitrogen 3 times. Dry CH2Cl2 (214 mL, 0.05 M) was added to the flask via cannula. The solution was bubbled with nitrogen for 15 min. The solution was then cooled to 5° C. and BF$_3$.Et$_2$O (1.61 mL, 12.9 mmol) was added. DDQ (2.43 g, 10.7 mmol) was added in 0.5 g increments over 30 min. The reaction was monitored by TLC using C18 silica plates in methanol. After DDQ addition was completed, continued to monitor the reaction. At 15 min after DDQ addition, added another 0.1 g of DDQ followed by another 0.1 g addition at 18 min after first DDQ addition. At 30 min after initial DDQ addition, 0.3 mL of BF$_3$.Et$_2$O was added followed by another 1 mL of BF$_3$.Et$_2$O at 40 min. At 1 h after initial DDQ addition was complete, no starting material was noticed by TLC and the reaction was quenched by the adding 3 g of Zn powder followed by stirring of the reaction for 2 h. The mixture was diluted with 200 mL of methanol and stirred for another hour. The mixture was diluted with water and extracted with chloroform (3×500 mL). The organic fractions were dried over MgSO$_4$ and then concentrated. The product was purified by column chromatography using hexane as the eluent to yield the product as pale yellow oil that crystallized upon standing (3.2 g, 64%). $^1$H NMR (300 MHz, CDCl$_3$): $\delta_H$ 7.90 (d, 2H), 7.37 (d, 2H), 2.77 (m, 4H), 1.72 (m, 16H), 0.89 (m, 12H).

Example 1e

Synthesis of (5,6-bis(2-ethylhexyl)naphtha[2,1-b:3,4-b']dithiophene-2,9-diyl)bis(trimethylstannane)

A dry 500-mL three-neck flask was flushed with $N_2$ and was charged with 5,6-bis(2-ethylhexyl)naphtho[2,1-b:3,4-b']dithiophene (2.0 g, 4.3 mmol) and dry THF (0.01 M) via deoxygenated syringe. The reaction flask was cooled to −78° C. and a 1.7 M solution of tert-butyllithium in hexanes (10.8 mmol) was added dropwise via deoxygenated syringe. After 30 minutes of stirring at −78° C., the solution was warmed up to 0° C. and stirring was continued for 20 minutes, at which point the reaction mixture was cooled back to −78° C. A 1 M solution of thrimethyltin chloride in THF (17.2 mmol) was added to the reaction flask dropwise and stirring continued for 1 hour at −76° C. The cooling bath was removed and the reaction mixture was allowed to warm to ambient temperature. As the reaction was completed, the reaction mixture concentrated, and washed with hexanes (100 mL) three times. The combined organic layer was filtered and the solvent was removed by rotary evaporation. The crude product (95% yield) was used for polymerization without further purification.

Example 2a

Synthesis of 1,2-bis(2-ethylhexyl)benzene

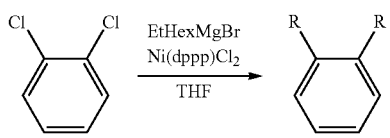

R: ethylhexyl

A dry 2-L three-neck flask equipped with a 500-mL addition funnel, a condenser, a stir bar, and a nitrogen outlet was charged with 1,2-dichlorobenzene (540 mmol), Ni(dppp)Cl₂ (6 mmol), and diethyl ether (200 mL). The addition funnel was charged with 3M 2-ethylhexylmagnesium bromide (400 mL). The reaction flask was cooled to 0° C. and the 2-ethylhexylmagnesium bromide was slowly added to the reaction. After the addition of Grignard reagent was completed, the reaction mixture was stirred at 0° C. for 1 hour. The reaction mixture was then warmed to gentle reflux for 12 hours. The reaction mixture was cooled to room temperature and poured onto ice and 100 mL of 10% HCl with vigorous stirring. The organic phase was separated and the aqueous phase was extracted with chloroform (3×500 mL). The combined organic phases were dried over anhydrous magnesium sulfate and excess solvent was removed by rotary evaporation. The volatile impurities were removed by distillation and the residue was purified by column chromatography (hexanes). The product was isolated as colorless oil (101 g, 62%).

Example 2b

Synthesis of 1,2-dibromo-3,4-bis(2-ethylhexyl)benzene

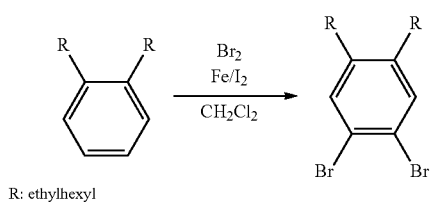

R: ethylhexyl

A dry 1-L 3-neck-flask fitted with an addition funnel, a reflux condenser, a stir bar, and a nitrogen outlet was charged with 1,2-bis(2-ethylhexyl)benzene (169 mmol), dichloromethane (170 mL), and a catalytic amount of Fe and $I_2$. The addition funnel was charged with bromine (354 mmol). The reaction flask was cooled to 0° C. and bromine was added drop wise to the reaction. After addition was complete, the reaction flask was warmed to room temperature and stirred for 14 hours. The reaction mixture was poured onto a mixture of ice and aqueous sodium thiosulfate. The mixture was extracted with chloroform (3×500 mL). The organic fractions were combined, dried over anhydrous magnesium sulfate and solvent was removed by rotary evaporation. The crude product was purified by column chromatography (hexanes). The product was isolated as pale yellow oil (72 g, 92%).

Example 2c

Synthesis of 3-[4,5-bis(2-ethylhexyl)-2-(3-thienyl)phenyl]thiophene

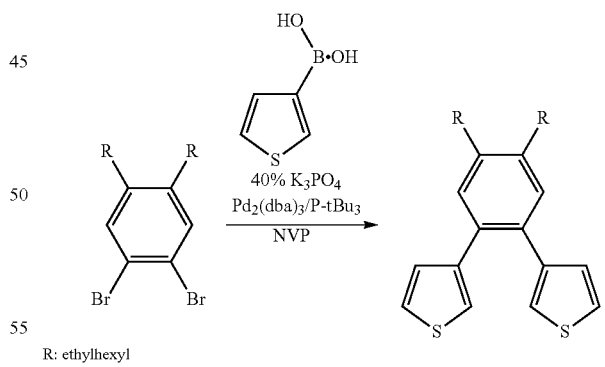

R: ethylhexyl

A dry 500-mL 3-neck flask equipped with a condenser, a stir bar, and a nitrogen outlet was charged with 1,2-dibromo-3,4-bis(2-ethylhexyl)benzene (20 g, 0.043 mol), 3-thiopheneboronic acid (12.2 g, 0.096 mol), 40% $K_3PO_4$ (92 mL), and N-methylpyrrolidone (100 mL). The reaction mixture was bubbled with nitrogen for 3 hours at which point tris(dibenzylideneacetone)dipalladium(0) (2.0 g, 2.2 mmol) and tri-tert-butylphosphine (2.6 g, 13 mmol) were charged into the reaction flask. The mixture was evacuated and refilled with nitrogen three times. The reaction flask was immersed into a preheated to 80° C. oil bath and was left stirring under nitrogen for 12 hours. The reaction was stopped by diluting it with water (100 mL). An excess of water (200 mL) was added and the crude product was extracted three times with diethyl ether. The combined organic layers were dried over anhydrous magnesium sulfate (MgSO$_4$). After solution was filtered, solvent was removed by rotary evaporation, and the crude product was purified by column chromatography on silica gel with hexanes. Compound was isolated as colorless oil (7.3 g, 37%). The purity was checked by NMR and GC/MS analysis.

Example 2d

Synthesis of 8,9-bis(2-ethylhexyl)naphtho[2,1-b:3,4-b]dithiophene

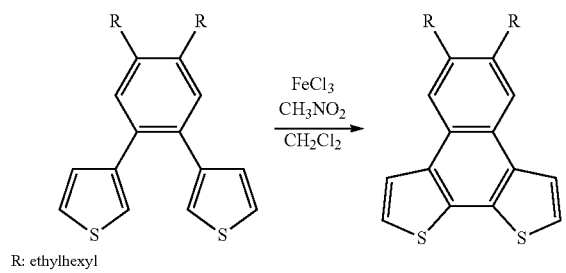

A dry 2-L 3-neck flask equipped with an addition funnel, a stir bar, and a nitrogen outlet was charged with 3-[4,5-bis(2-ethylhexyl)-2-(3-thienyl)phenyl]thiophene (4.2 mmol) and dry methylene chloride (400 mL). The addition funnel was charged with iron (III) chloride (9.4 mmol) dissolved in nitromethane (40 mL). Under a strong nitrogen flow, the iron (III) chloride solution was added slowly to the reaction mixture. After 30 minutes, the reaction was stopped by addition of anhydrous methanol (20 mL). The reaction was diluted with methanol (500 mL), and the resulting precipitate was collected by filtration. The precipitate was dissolved in chloroform and reprecipitated in methanol. The final product was purified by recrystallization from chloroform. The product was isolated as pale yellow solid and yields ranged between 30 and 50%.

The methods of example 1e were used to make a polymerization monomer.

Polymer, Ink, Device Preparation and Testing

Example 3

Synthesis of poly {(5,6-bis(2'-ethylhexyloxy)naphtha[2,1-b:3,4-b']dithiophene-alt-(5-(2-ethylhexyl)thieno[3,4-c]pyrrole-4,6-dione)-alt-(5,6-bis(2'-ethylhexyloxy)naphtha[2,1-b:3,4-b']dithiophene-alt-5-diethylhexyl-3,6-dithiophen-2-ylpyrrolo[3,4-c]pyrrole-1,4-dione)}

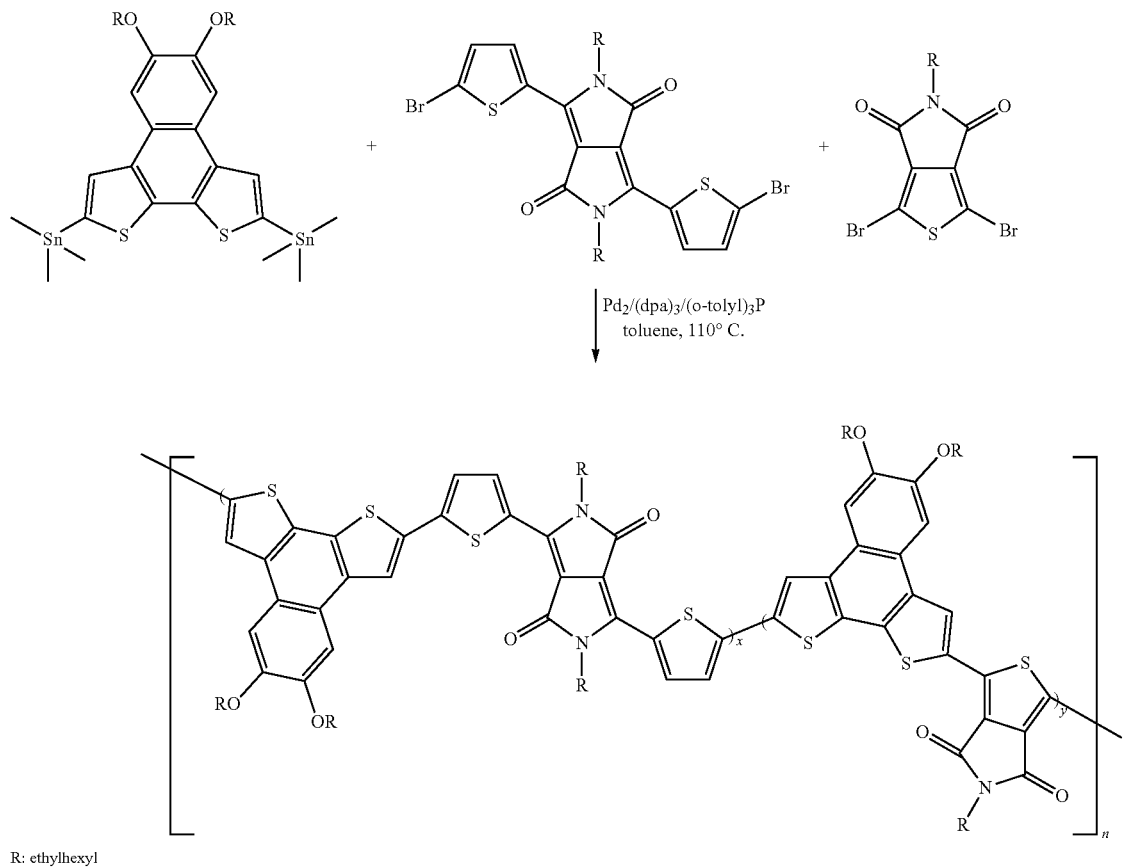

In a glove box, bis(trimethyltin)-5,6-bis(2'-ethylhexyloxy) naphtha[2,1-b:3,4-b']dithiophene (1.2 g, 1.46 mmol), 1,3-dibromo-5-(2-ethylhexyl)thieno[3,4-c]pyrrole-4,6-dione (0.28 g, 0.66 mmol), 2,5-diethylhexyl-3,6-bis(5-bromothiophen-2-yl)pyrrolo[3,4-c]-pyrrole-1,4-dione (0.45 g, 0.66 mmol), tris(dibenzylideneacetone)dipalladium(0) (0.033 g, 0.036 mmol) and tris(o-tolyl)phosphine (0.044 g, 0.146 mmol) were weighted out into a flame dried 50 mL Schlenk flask. Reaction flask was removed from the glove box and 15 mL of deoxygenated toluene were added via mined by GPC in 1,3,5-trichlorobenzene (1 mL/min at 150° C.) vs. polystyrene standards: $M_n$=7,800, $M_w$=12,600, PDI=1.6.

Example 4

Synthesis of poly{(2,5'-8,9-bis(2-ethylhexyloxy)-naphtho[2,1-b:3,4-b']dithiophene-alt-(N,N-diphenyl-4-sec-butyl-aniline)-alt-(2,5'-8,9-bis(2-ethylhexyl)-naphtho[2,1-b:3,4-b']dithiophene-alt-5-diethylhexyl-3,6-dithiophen-2-ylpyrrolo[3,4-c]pyrrole-1,4-dione)}

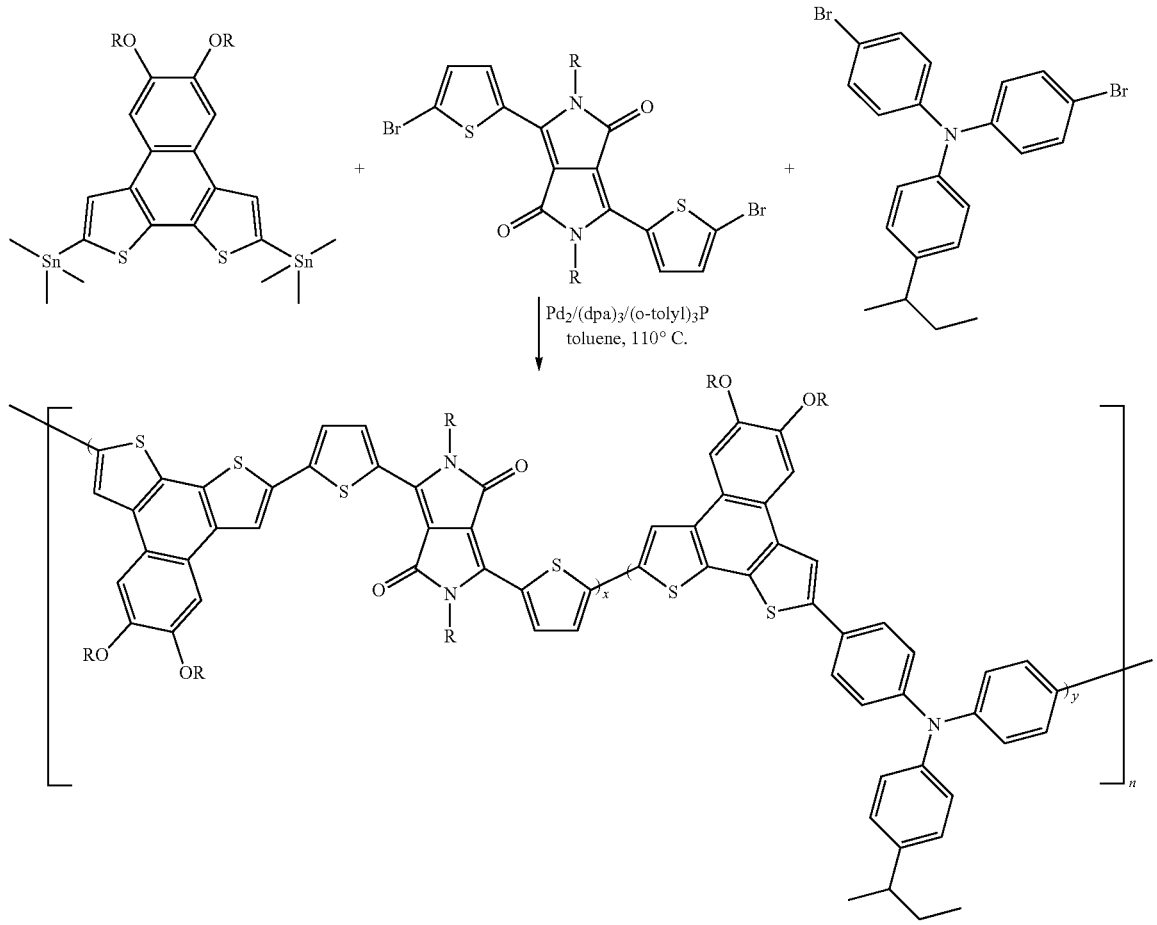

R: ethylhexyl syringe. The mixture was evacuated and refilled with argon five times. The reaction flask was immersed into a preheated to 110° C. oil bath and was left stirring under an argon stream for 12 hours. The polymerization was quenched with 0.3 mL of 2-iodothiophene and stirred at 110° C. for additional two hours. The oil bath was removed and after cooling to room temperature, 40 mL of methanol were added to the reaction mixture under vigorous stirring to induce precipitation. The final mixture was poured into 200 mL of methanol and the polymer was collected via filtration. The polymer was purified by consecutive Soxhlet extractions in sequence with methanol, acetone, hexane, and chloroform. The chloroform fraction was passed through celite, to remove catalyst residuals, and solvent was removed under vacuum to yield a brown colored polymer (0.94 g, 50%). Molecular weight was deter- In a glove box, 8,9-bis(2-ethylhexyloxy)-2,5-bis(trimethylstannyl)nahtho[2,1-b:3,4-b']dithiophene (1.2 g, 1.46 mmol), 2,5-diethylhexyl-3,6-bis(5-bromothiophen-2-yl)pyrrolo[3,4-c]-pyrrole-1,4-dione (0.68 g, 1.00 mmol), N-(4-sec-butylphenyl)-4-bromo-N-(4-bromophenyl)aniline (0.15 g, 0.33 mmol), tris(dibenzylideneacetone)dipalladium(0) (0.033 g, 0.037 mmol) and tris(o-tolyl)phosphine (0.044 g, 0.146 mmol) were charged into a flame dried 50 mL Schlenk flask. The reaction flask was removed from the glove box and 15 mL of deoxygenated toluene were added via syringe. The mixture was evacuated and refilled with argon five times. The reaction flask was immersed into a preheated to 110° C. oil bath and left stirring under an argon stream for 12 hours. The polymerization was quenched with 0.3 mL of 2-iodothiophene and stirred at 110° C. for additional two hours. The oil bath was removed and after cooling to room temperature, 15 mL of methanol were added to the reaction mixture under vigorous stirring to induce precipitation. The final mixture was poured into 200 mL of methanol, and polymer was collected via filtration. The polymer was purified by consecutive Soxhlet extractions in sequence with methanol, acetone, hexane, and chloroform. The chloroform fraction was passed through celite, to remove catalyst residuals, and solvent was removed under vacuum to yield dark green powder (1.2 g, 45%). Chloroform fraction was concentrated, re-precipitated in methanol, isolated via filtration, and molecular weight was determined by GPC in 1,3,5-trichlorobenzene (1 mL/min at 150° C.) vs. polystyrene standards: $M_n$=11,000, $M_w$=19,750, PDI=1.8.

Example 5

Synthesis of poly {2,5'-8,9-bis(2-ethylhexyloxy)-naphtho[2,1-b:3,4-b]dithiophene-alt-5-diethylhexyl-3,6-dithiophen-2-ylpyrrolo[3,4-c]pyrrole-1,4-dione}

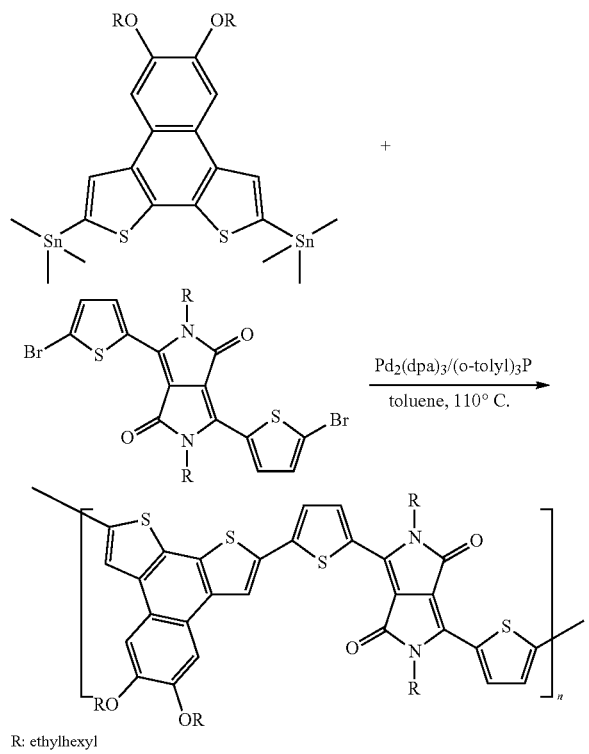

R: ethylhexyl

In a glove box, 8,9-Bis(2-ethylhexyloxy)-2,5-Bis(trimethylstannyl)nahtho[2,1-b:3,4-b']dithiophene (0.76 g, 0.92 mmol), 2,5-diethylhexyl-3,6-bis(5-bromothiophen-2-yl)pyrrolo[3,4-c]-pyrrole-1,4-dione (0.631 g, 0.92 mmol), tris(dibenzylideneacetone)dipalladium(0) (0.021 g, 0.023 mmol) and tris(o-tolyl)phosphine (0.028 g, 0.092 mmol) were charged into a flame dried 50 mL Schlenk flask. The reaction flask was removed from the glove box and 9 mL of deoxygenated toluene were added via syringe. The mixture was evacuated and refilled with argon five times. The reaction flask was immersed into a preheated to 110° C. oil bath. The polymerization was completed within 8 minutes at which point the solution became very viscous. The mixture was diluted with toluene (5 mL), quenched with 0.3 mL of 2-iodothiophene, and stirred at 110° C. for additional two hours. The oil bath was removed and after cooling to room temperature, 15 mL of methanol were added to the reaction mixture under vigorous stirring. The final mixture was poured into 200 mL of methanol, and polymer was collected via filtration. The polymer was purified by consecutive Soxhlet extractions in sequence with methanol, acetone, hexane, and chloroform. The chloroform fraction was passed through celite, to remove catalyst residuals, and solvent was removed by rotary evaporation to yield polymer. The chloroform fraction was redissolved in a minimum amount of chloroform, re-precipitated in a methanol/IPA/water mixture, isolated via filtration to yield a black solid (80%). Molecular weight was determined by GPC in 1,3,5-trichlorobenzene (1 mL/min at 150° C.) vs. polystyrene standards: $M_n$=6,100, $M_w$=9,900, PDI=1.6.

Fabrication of Solar Cell Devices Using Polymers and Fullerene Acceptors

Indium tin oxide ("ITO") coated glass substrates were purchased from Thin Film Devices ("TFD", Anaheim, Calif.). These substrates were cleaned in a Class 10,000 clean room by sonicating for 20 min in a soap solution, followed by 20 min of sonication in water, 20 min of sonication in acetone and 20 min of sonication in IPA. Finally the substrates were exposed to UV ozone (300 W) for 10 min. After cleaning, each substrate was then coated with a ~30 nm thick layer of Baytron AI4083 (H. C Stark) by spin coating for 5 seconds at 400 rpm in air, followed by a 1 minute at 6000 rpm. The devices were then transferred to a $N_2$ atmosphere glovebox and annealed on a hot plate at 175° C. for 30 min.

The active layer was then spin-coated on top of the PEDOT:PSS layer on a Headway spinner at spin speeds ranging from 100-1000 rpm to obtain the required active layer thickness. The active layer films were either allowed to dry in the glovebox or were annealed on the hot plate to dry. (See Table I for treatment conditions for each sample.) Finally, after annealing, the cathode was vapor deposited from a base pressure of $\sim 7 \times 10^{-7}$. In all of the following working examples, the cathode for the devices was a bilayer of Ca (25 nm) and Al (200 nm). The Ca and Al were deposited at rates of 0.3 A/s and 4 A/s, respectively. The devices were then encapsulated via a glass cover slip (blanket) encapsulation sealed with EPO-TEK OG112-4 UV curable glue. The encapsulated device was cured under UV irradiation (80 mW/cm$^2$) for 4 minutes and tested as follows.

The photovoltaic characteristics of devices under white light exposure (Air Mass 1.5 Global Filter) were measured using a system equipped with a Keithley 2400 source meter and an Oriel 300 W Solar Simulator based on a Xe lamp with output intensity of 100 mW/cm$^2$ (AM1.5 G). The light intensity was set using an NREL-certified Si-KG5 silicon photodiode.

Power Conversion Efficiency Determinations

Devices prepared as described above were tested using an Oriel Solar Simulator and the voltage was swept from reverse to forward bias. From the resulting current that was measured, the power conversion efficiency of each device was determined. Data for each device as well as relevant processing parameters for each device are summarized in Tables 1-3.

TABLE 1

| Polymer | | 3 |
|---|---|---|
| N-type | | C70 PCBM |
| p/n ratio | | 1:1 |
| solvent | (volume solids) | o-xylene (0.011) |
| Drying Conditions | T° C./Time/Atmosphere | No anneal |
| Avg. $J_{SC}$ | mA/cm$^2$ | 7.62 |
| Avg $V_{OC}$ | V | 0.68 |

TABLE 1-continued

| | | |
|---|---|---|
| Avg FF | | 0.57 |
| Avg PCE | % | 2.92 |

TABLE 2

| | | |
|---|---|---|
| Polymer | | 4 |
| N-type | | C70 PCBM |
| p/n ratio | | 1:3 |
| solvent | (volume solids) | o-xylene (0.011) |
| Drying Conditions | T° C./Time/Atmosphere | 85/18 min/nitrogen |
| Avg. $J_{SC}$ | mA/cm$^2$ | 9.47 |
| Avg $V_{OC}$ | V | 0.63 |
| Avg FF | | 0.58 |
| Avg PCE | % | 3.43 |

TABLE 3

| | | |
|---|---|---|
| Polymer | | 5 |
| N-type | | PCBM |
| p/n ratio | | 1:4 |
| solvent | (volume solids) | Chlorobenzene (0.0075) |
| Drying Conditions | T° C./Time/Atmosphere | 30/20 min/nitrogen |
| Avg. $J_{SC}$ | mA/cm$^2$ | 6.68 |
| Avg $V_{OC}$ | V | 0.65 |
| Avg FF | | 0.49 |
| Avg PCE | % | 2.11 |

Power conversion efficiencies of greater than 2%, and greater than 3% were achieved. Additional data are provided below:

| p-type | n-type* | p/n ratio | Conc/solvent | spin rpm/t/atm | Anneal T/t/atm | $J_{SC}$ mA/cm$^2$ | $V_{OC}$ (V) | FF | η (%) |
|---|---|---|---|---|---|---|---|---|---|
| Example 3 | C60-PCBM | 1:1 | 0.011CB | 400/300/260 | None | 6.71 | 0.65 | 0.45 | 1.94 |
| Comparative Example 1 | C60-PCBM | 1:1 | 0.011CB | 600/300/GB | None | 1.66 | 0.73 | 0.30 | 0.36 |
| Example 4 | C70-PCBM | 1:3 | 0.011OX | 100/300/260 | 85/18 | 9.47 | 0.63 | 0.58 | 3.43 |
| Comparative Example 2 | C70-PCBM | 1:3 | 0.011OX | 100/300/GB | 85/18/GB | 4.54 | 0.11 | 0.24 | 0.12 |

In comparative examples 1 and 2, the benzo[2,1-b:3,4-b'] dithiophene moieties were replaced with benzo[2,1-b:4,5-b'] dithiophene moieties.

Comments:
Solvents—CB [chlorobenzene]; OX [o-xylene]
The data showed that power conversion efficiency could be increased with use of the benzo[2,1-b:3,4-b']dithiophene benzo[2,1-b:4,5-b']dithiophene by more than five fold or more than 30 fold.

Sixty-Six Embodiments from Priority Provisional Application Ser. No. 61/222,053 Filed Jun. 30, 2009

Embodiment 1

A composition comprising at least one copolymer, said at least one copolymer comprising at least one first bithiophene repeat unit represented by:

wherein $R_1$, $R_2$ and R' are solubilizing groups.

Embodiment 2

The composition according to embodiment 1, wherein $R_1$ and $R_2$ each comprise one or more optionally substituted aryl, optionally substituted heteroaryl, optionally substituted cycloalkyl moieties.

Embodiment 3

The composition according to embodiment 1, wherein said at least one bithiophene repeat unit is represented by:

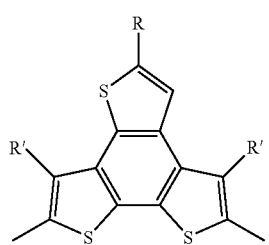

and further wherein R and R' are solubilizing groups.

Embodiment 4

The composition according to embodiment 1, wherein said at least one bithiophene repeat unit is represented by:

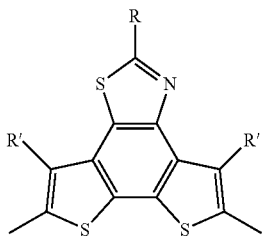

and further wherein R and R' are solubilizing groups.

Embodiment 5

The composition according to embodiment 1, wherein said at least one bithiophene repeat unit is represented by:

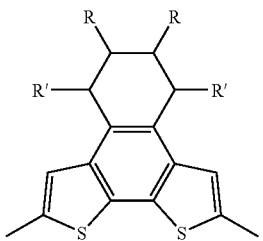

and further wherein R and R' are solubilizing groups.

Embodiment 6

The composition according to embodiment 1, wherein at least one bithiophene repeat unit is represented by:

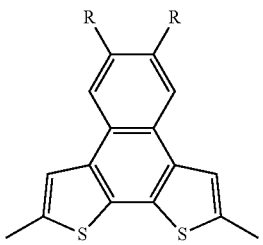

and further wherein R are solubilizing groups.

Embodiment 7

The composition according to embodiment 1, wherein said at least one bithiophene repeat unit is represented by:

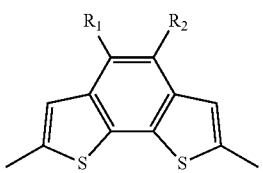

and further wherein $R_1$ and $R_2$ comprise branched alkyl groups.

Embodiment 8

The composition according to embodiment 1, wherein said at least one bithiophene repeat unit is represented by:

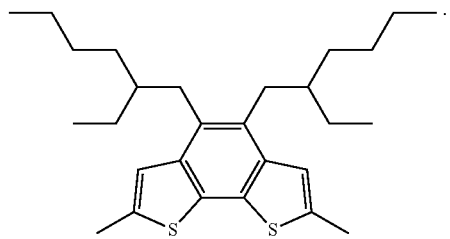

Embodiment 9

The composition according to embodiment 1, wherein said at least one bithiophene repeat unit is represented by:

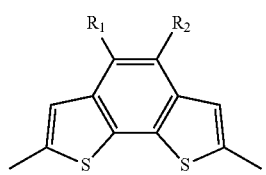

and further wherein $R_1$ and $R_2$ comprise alkyleneoxy groups.

Embodiment 10

The composition according to embodiment 1, wherein said at least one bithiophene repeat unit is represented by:

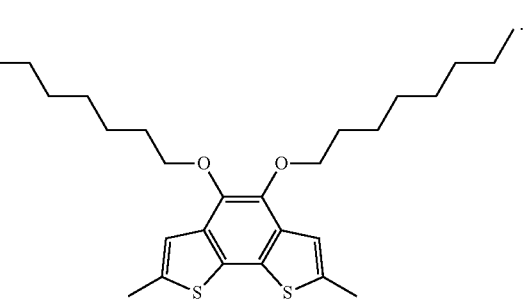

Embodiment 11

The composition according to embodiment 1, wherein said at least one bithiophene repeat unit is represented by at least one of the following:

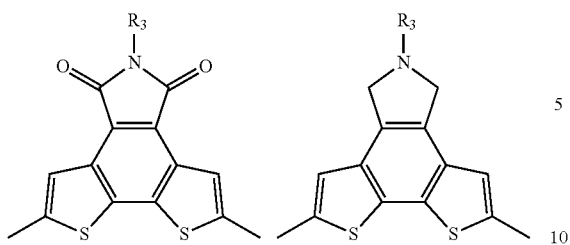

wherein R₃ is a solubilizing group.

Embodiment 12

The composition according to embodiment 1, wherein said at least one copolymer is an alternating copolymer.

Embodiment 13

The composition according to embodiment 1, wherein said at least one copolymer comprises repeating dimer units, said repeating dimer units comprising said at least one first bithiophene repeat unit and a second repeat unit.

Embodiment 14

The composition according to embodiment 1, wherein said at least one copolymer comprises repeating dimer units, said repeating dimer units comprising said at least one first bithiophene repeat unit and a second repeat unit, said second repeat unit comprising at least one ring structure.

Embodiment 15

The composition according to embodiment 1, wherein said at least one copolymer comprises repeating dimer units, said dimer units comprising said at least one first bithiophene repeat unit and a second repeat unit, said second repeat unit comprising at least one fused ring structure.

Embodiment 16

The composition according to embodiment 1, wherein said at least one copolymer comprises repeating dimer units, said dimer units comprising said at least one first bithiophene repeat unit and a second repeat unit, said second repeat unit comprising at least one aromatic ring structure.

Embodiment 17

The composition according to embodiment 1, wherein said at least one copolymer comprises repeating dimer units, said dimer units comprising said at least one first planarized bithiophene repeat unit and a second repeat unit, said second repeat unit comprising at least one thiophene ring structure.

Embodiment 18

The composition according to embodiment 1, wherein said at least one copolymer comprises repeating dimer units, said dimer units comprising said at least one first bithiophene repeat unit and a second repeat unit, said second repeat unit being represented by at least one of the following:

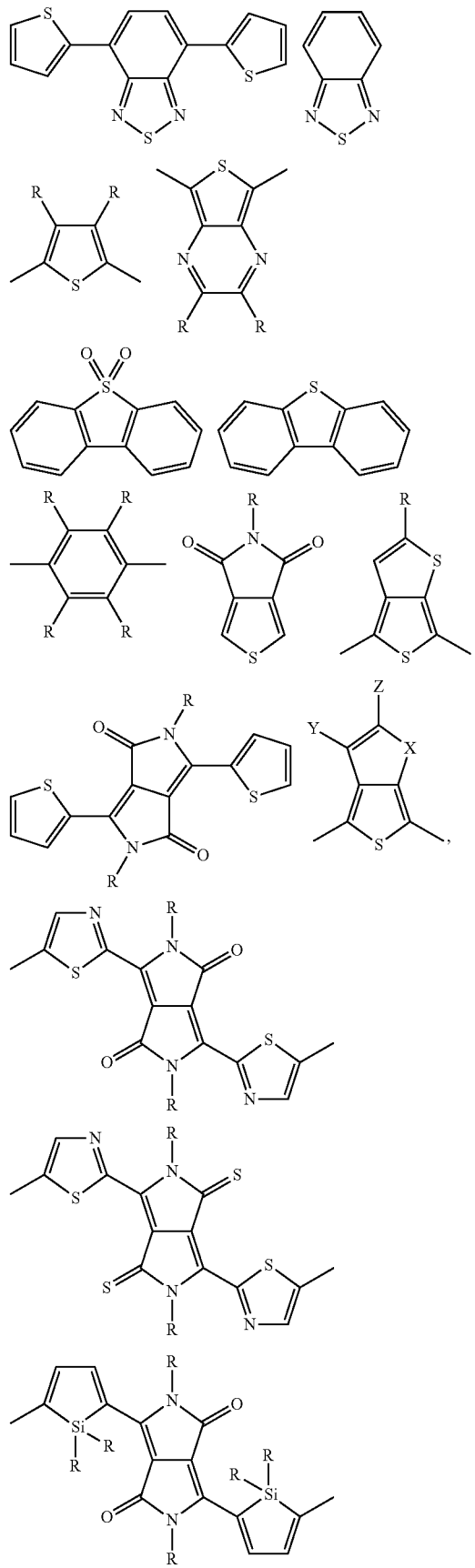

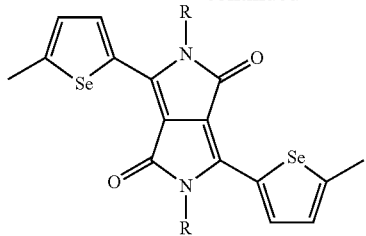

wherein R are solubilizing groups, X is sulfur, oxygen, or nitrogen, or selenium. Y is a halogen or hydrogen, and Z is alkyl or branched alkyl.

Embodiment 19

The composition according to embodiment 1, wherein said at least one copolymer comprises repeating dimer units, said dimer unit comprising said at least one first bithiophene repeat unit and a second repeat unit, said second repeat unit being represented by at least one of the following:

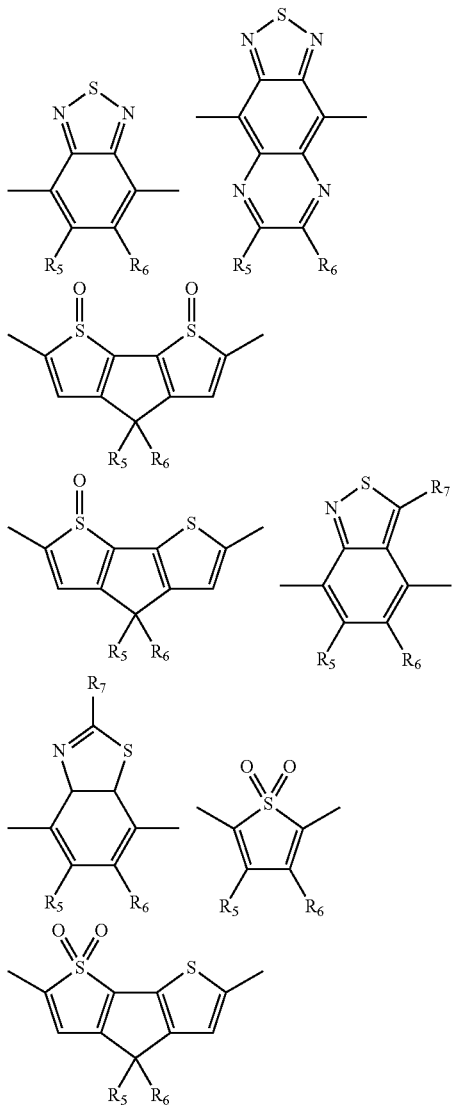

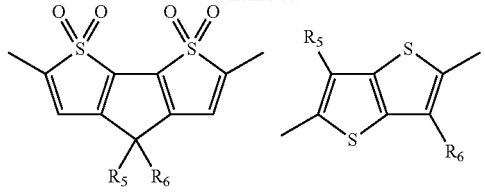

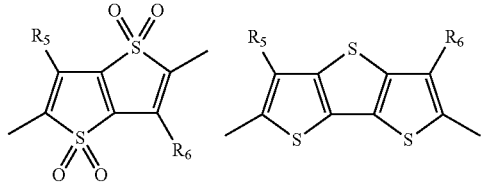

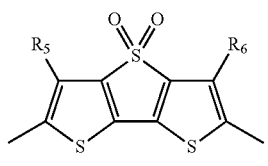

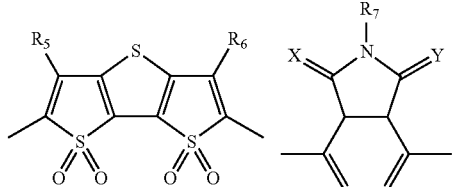

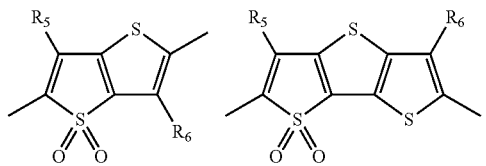

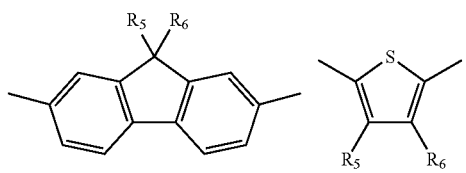

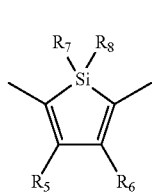

wherein $R_5$, $R_6$, $R_7$, and $R_8$ are solubilizing groups and X and Y are independently $CH_2$, O, or S.

Embodiment 20

The composition according to embodiment 1, wherein said at least one copolymer comprises repeating dimer units, said dimer units comprising at least one first bithiophene repeat unit and a second repeat unit, said second repeat unit being represented by at least one of the following:

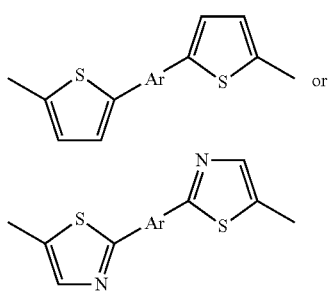

wherein Ar is represented by:

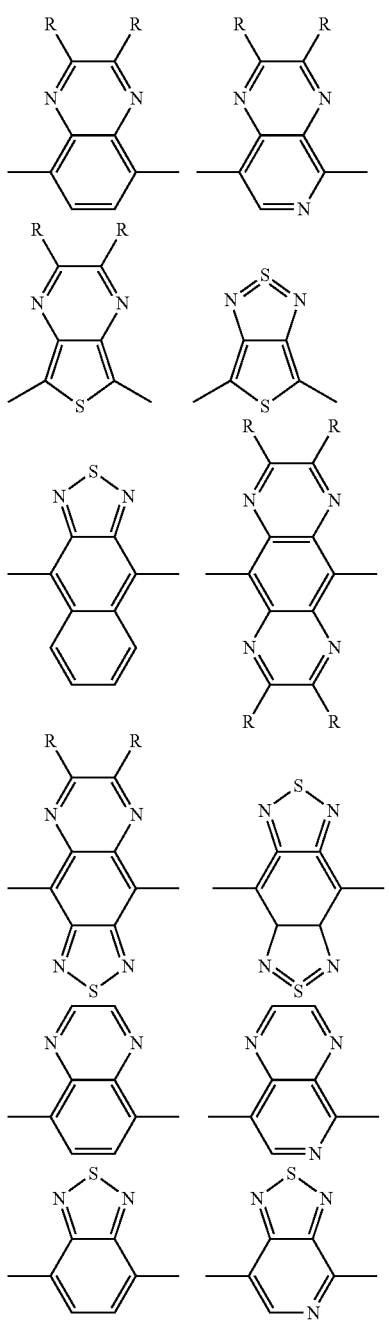

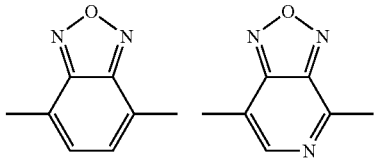

and further wherein R are solubilizing groups.

Embodiment 21

The composition according to embodiment 1, wherein said at least one copolymer further comprises a silole moiety.

Embodiment 22

The composition according to embodiment 1, wherein said at least one copolymer further comprises a moiety represented by:

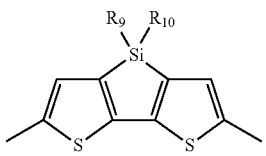

wherein $R_9$ and $R_{10}$ are independently optionally substituted alkyl, optionally substituted aryl or heteroaryl, optionally substituted alkenyl, or optionally substituted alkynyl.

Embodiment 23

The composition according to embodiment 22, wherein at least one of $R_9$ or $R_{10}$ is a branched alkyl.

Embodiment 24

The composition according to embodiment 22, wherein $R_9$ and $R_{10}$ are branched alkyls.

Embodiment 25

The composition according to embodiment 1, wherein said at least one copolymer further comprises at least one second planarized repeat unit represented by:

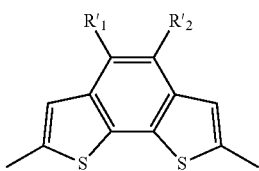

wherein $R_1'$ and $R_2'$ are solubilizing groups, and further wherein said at least one first bithiophene repeat unit and said at least one second bithiophene repeat unit are not identical.

Embodiment 26

The composition according to embodiment 1, wherein said at least one copolymer is resistant to oxidation in air.

Embodiment 27

A composition comprising at least one copolymer, said at least one copolymer comprising at least one first bithiophene repeat unit represented by:

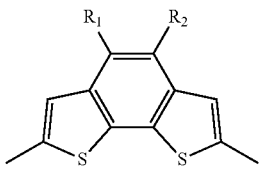

wherein $R_1$ and $R_2$ are solubilizing groups, further wherein said at least one copolymer does not comprise poly[2,6-(4,4-dioctyl-4H-cyclopenta[2,1-b:3,4-b']dithiophene)-alt-2,7-(4,5-dioctylbenzo[2,1-b:3,4-b']dithiophene)], poly[2,6-(4,4-dioctyl-4H-cyclopenta[2,1-b:3,4-b']dithiophene)-alt-2,9-(5,6-dioctylnaphtho[2,1-b:3,4-b']dithiophene)], or poly[2,6-(4,4-dioctyl-4H-cyclopenta[2,1-b:3,4-b']dithiophene)-alt-6,9-(2,3-bis((S)-2,6-dimethylheptyl)ditheno[3,2-f:2',3'-h]quinoxaline].

Embodiment 28

A composition comprising a mixture comprising: (i) at least one p-type material, (ii) at least one n-type material, wherein the at least one p-type material comprises at least one copolymer, said at least one copolymer comprising at least one first bithiophene repeat unit represented by:

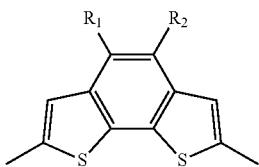

wherein $R_1$ and $R_2$ are solubilizing groups.

Embodiment 29

The composition according to embodiment 28, wherein the at least one n-type material comprises at least one fullerene derivative comprising at least [6,6] fullerene bonding site wherein both carbon atoms of the [6,6] bonding site are covalently bonded to a group R.

Embodiment 30

The composition according to embodiment 29, wherein the group R comprises optionally substituted indene.

Embodiment 31

The composition according to embodiment 28, wherein the at least one n-type material comprises a $C_{60}$-indene adduct.

Embodiment 32

The composition according to embodiment 28, wherein the at least one n-type material comprises PCBM.

Embodiment 33

The composition according to embodiment 28, wherein the at least one copolymer is resistant to oxidation in air.

Embodiment 34

A composition comprising a mixture comprising: (i) at least one p-type material, (ii) at least one n-type material, wherein the at least one p-type material comprises at least one copolymer, said at least one copolymer comprising at least one first bithiophene repeat unit represented by:

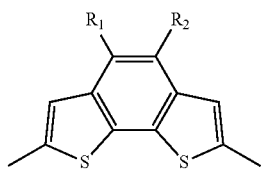

wherein $R_1$ and $R_2$ are solubilizing groups, further wherein said at least one copolymer does not comprise poly[2,6-(4,4-dioctyl-4H-cyclopenta[2,1-b:3,4-b']dithiophene)-alt-2,7-(4,5-dioctylbenzo[2,1-b:3,4-b']dithiophene)], poly[2,6-(4,4-dioctyl-4H-cyclopenta[2, 1-b: 3,4-b']dithiophene)-alt-2,9-(5,6-dioctylnaphtho[2,1-b:3,4-b']dithiophene)], or poly[2,6-(4,4-dioctyl-4H-cyclopenta[2,1-b:3,4-b']dithiophene)-alt-6,9-(2,3-bis((S)-2,6-dimethylheptyl)ditheno[3,2-f:2',3'-h]quinoxaline].

Embodiment 35

A composition comprising at least one dimer, said at least one dimer comprising at least one first structure represented by:

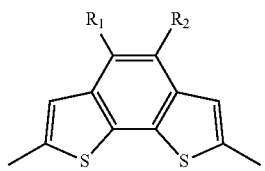

wherein $R_1$ and $R_2$ are solubilizing groups.

Embodiment 36

The composition according to embodiment 35, wherein $R_1$ and $R_2$ each comprise one or more optionally substituted aryl, optionally substituted heteroaryl, optionally substituted cycloalkyl moieties.

Embodiment 37

The composition according to embodiment 35, wherein said at least first structure is represented by:

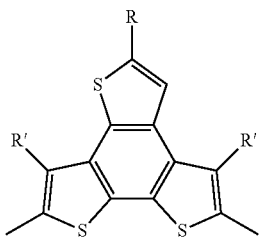

and further wherein R and R' are solubilizing groups.

Embodiment 38

The composition according to embodiment 35, wherein said at least one first structure is represented by:

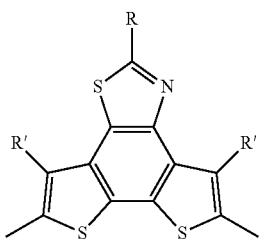

and further wherein R and R' are solubilizing groups.

Embodiment 39

The composition according to embodiment 35, wherein said at least one first structure is represented by:

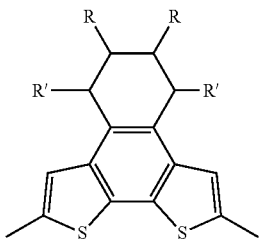

and further wherein R and R' are solubilizing groups.

Embodiment 40

The composition according to embodiment 35, wherein said at least one first structure is represented by:

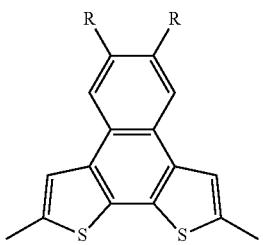

and further wherein R are solubilizing groups.

Embodiment 41

The composition according to embodiment 35, wherein said at least one first structure is represented by:

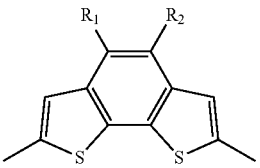

and further wherein $R_1$ and $R_2$ comprise branched alkyl groups.

Embodiment 42

The composition according to embodiment 35, wherein said at least first structure is represented by:

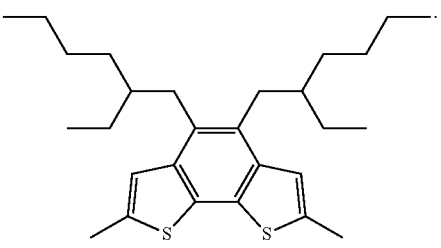 [SMILES: CCCCC(CC)Cc1c(CC(CC)CCCC)c2cc(C)sc2c2sc(C)cc12]

Embodiment 43

The composition according to embodiment 35, wherein said at least one first structure is represented by:

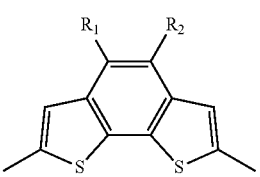

and further wherein $R_1$ and $R_2$ comprise alkyleneoxy groups.

Embodiment 44

The composition according to embodiment 35, wherein said at least one first structure is represented by:

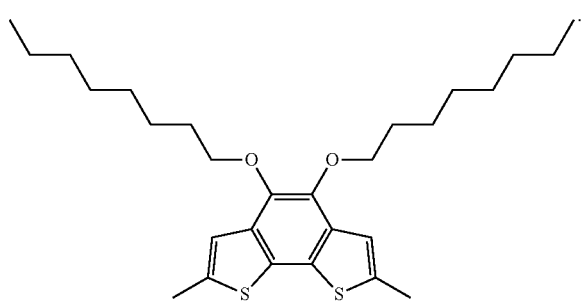 [SMILES: CCCCCCCCOc1c(OCCCCCCCC)c2cc(C)sc2c2sc(C)cc12]

Embodiment 45

The composition according to embodiment 35, wherein said at least one first structure is represented by at least one of the following:

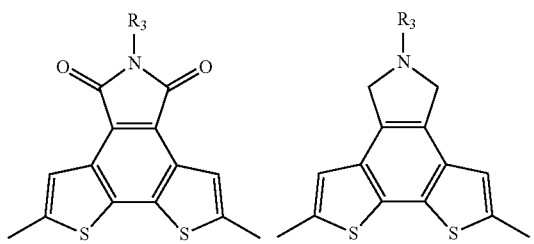

wherein $R_3$ is a solubilizing group.

Embodiment 46

The composition according to embodiment 35, wherein said at least one dimer further comprises at least one second structure, said at least one second structure comprising at least one ring structure.

Embodiment 47

The composition according to embodiment 35, wherein said at least one dimer further comprises at least one second structure, said at least one second structure comprising at least one fused ring structure.

Embodiment 48

The composition according to embodiment 35, wherein said at least one dimer further comprises at least one second structure, said at least one second structure comprising at least one aromatic ring structure.

Embodiment 49

The composition according to embodiment 35, wherein said at least one dimer further comprises at least one second structure, said at least one second structure comprising a silole moiety.

Embodiment 50

The composition according to embodiment 35, wherein said at least one dimer further comprises at least one second structure represented by:

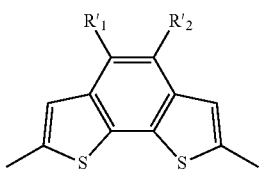

wherein $R_1'$ and $R_2'$ are solubilizing groups, and further wherein said at least one first structure unit and said at least one second structure are not identical.

Embodiment 51

A composition comprising at least one homopolymer, the at least one homopolymer comprising at least one first bithiophene repeat unit represented by:

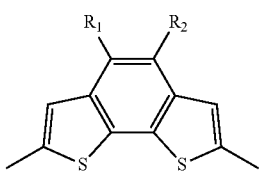

wherein $R_1$ and $R_2$ are solubilizing groups.

Embodiment 52

A method comprising: providing a first thiophene compound, said first thiophene compound comprising a first thiophene ring, said first thiophene ring having a first halogen attached to its 2-position and a first carbon attached to its 3-position; providing a second thiophene compound, said second thiophene comprising a second thiophene ring, said second thiophene ring having a second halogen attached to its 2-position and a second carbon attached to its 3-position; forming a first bond between said first carbon and said second carbon; and dehalogenating said first halogen and said second halogen to form a second bond between said first thiophene ring and said second thiophene ring, thereby forming a product comprising said first thiophene ring and said second thiophene ring.

Embodiment 53

The method according to embodiment 52, wherein one of said first thiophene compound and said second thiophene compound is an ylide.

Embodiment 54

The method according to embodiment 52, wherein one of said first thiophene compound and said second thiophene compound is an aldehyde.

Embodiment 55

The method according to embodiment 52, wherein said first bond comprises a carbon-carbon double bond.

Embodiment 56

The product produced according to the method of embodiment 52.

Embodiment 57

A method comprising: providing the product according to embodiment 56, halogenating said product to form a dihalogenated comonomer.

Embodiment 58

A product comprising the dihalogenated comonomer produced according to the method of embodiment 57.

Embodiment 59

A method comprising: providing the product according to embodiment 56 or embodiment 58, and subjecting said product to an organometallic mediated coupling reaction to form a homopolymer or a copolymer.

Embodiment 60

A product comprising the homopolymer or copolymer produced by the method according to embodiment 59.

Embodiment 61

An electronic device comprising the composition of embodiment 1 or embodiment 27 or embodiment 28 or embodiment 34 or embodiment 35 or embodiment 51.

Embodiment 62

The electronic device of embodiment 61, wherein the device is a photovoltaic cell.

Embodiment 63

The electronic device of embodiment 61, wherein the device is a photovoltaic cell comprising an active layer, said active layer comprising the composition of embodiment 1 or embodiment 27 or embodiment 28 or embodiment 34 or embodiment 35 or embodiment 51.

Embodiment 64

The electronic device of embodiment 61, wherein the device is a light-emitting diode.

Embodiment 65

The electronic device of embodiment 61, wherein the device is a field effect transistor.

Embodiment 66

An ink comprising the composition of embodiment 1 or embodiment 27 or embodiment 28 or embodiment 34 or embodiment 35 or embodiment 51.

This concludes the 66 embodiments from the priority provisional application.

What is claimed:

1. A composition comprising at least one donor acceptor copolymer, said at least one copolymer comprising at least one first bithiophene repeat unit represented by (I):

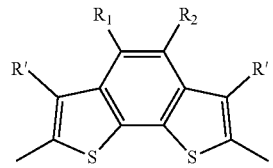

(I)

wherein $R_1$, $R_2$ and R' are solubilizing groups or hydrogen, and wherein $R_1$ and $R_2$ form an optionally substituted ring.

2. The composition of claim 1, wherein R' are each hydrogen.

3. The composition of claim 1, wherein $R_1$ and $R_2$ are solubilizing groups.

4. The composition of claim 1, wherein R' are each hydrogen and $R_1$ and $R_2$ are each solubilizing groups.

5. The composition of claim 1, wherein $R_1$ and $R_2$ form an aromatic ring.

6. The composition of claim 1, wherein $R_1$ and $R_2$ form a benzene ring.

7. The composition of claim 1, wherein $R_1$ and $R_2$ form a heterocyclic ring.

8. The composition according to claim 1, wherein said at least one bithiophene repeat unit is represented by:

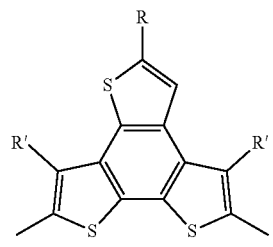

and further wherein R and R' are solubilizing groups or hydrogen.

9. The composition according to claim 1, wherein said at least one bithiophene repeat unit is represented by:

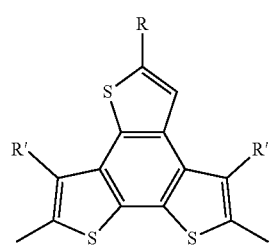

and further wherein R' is hydrogen and R is a solubilizing group.

10. The composition according to claim 1, wherein said at least one bithiophene repeat unit is represented by:

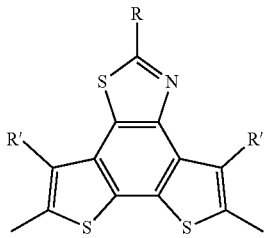

and further wherein R and R' are solubilizing groups or hydrogen.

11. The composition according to claim 1, wherein said at least one bithiophene repeat unit is represented by:

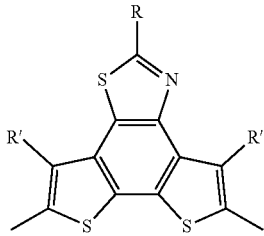

and further wherein R is a solubilizing group and R' is hydrogen.

12. The composition according to claim 1, wherein said at least one bithiophene repeat unit is represented by:

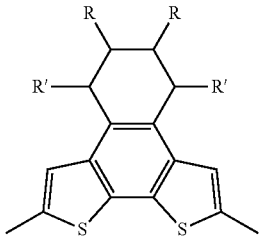

and further wherein R and R' are solubilizing groups or hydrogen.

13. The composition according to claim 1, wherein at least one bithiophene repeat unit is represented by (III):

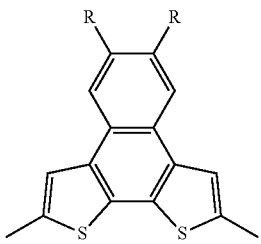

(III)

and further wherein R are solubilizing groups or hydrogen.

14. The composition according to claim 1, wherein at least one bithiophene repeat unit is represented by:

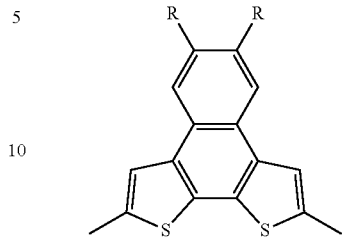

and further wherein R are solubilizing groups.

15. The composition according to claim 1, wherein said at east one bithiophene repeat unit is represented by at least one of the following:

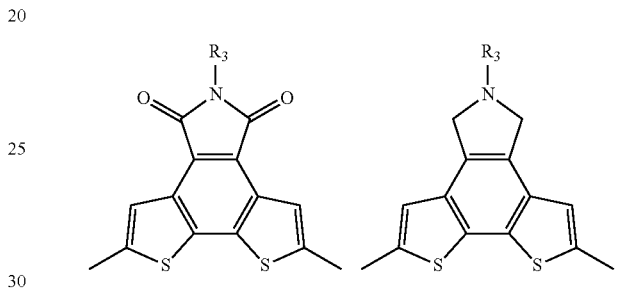

wherein $R_3$ is a solubilizing group.

16. The composition of claim 1, wherein the structure (I) provides a donor to the donor acceptor copolymer.

17. The composition according to claim 1, wherein said at least one copolymer is an alternating copolymer.

18. The composition according to claim 1, wherein said at least one copolymer comprises repeating dimer units, said repeating dimer units comprising said at least one first bithiophene repeat unit (I) and a second repeat unit.

19. The composition according to claim 1, wherein said at least one copolymer comprises repeating dimer units, said repeating dimer units comprising said at least one first bithiophene repeat unit (I) and a second repeat unit, said second repeat unit comprising at least one ring structure.

20. The composition according to claim 1, wherein said at least one copolymer comprises repeating dimer units, said dimer units comprising said at least one first bithiophene repeat unit (I) and a second repeat unit, said second repeat unit comprising at least one fused ring structure.

21. The composition according to claim 1, wherein said at least one copolymer comprises repeating dimer units, said dimer units comprising said at least one first bithiophene repeat unit (I) and a second repeat unit, said second repeat unit comprising at least one aromatic ring structure.

22. The composition according to claim 1, wherein said at least one copolymer comprises repeating dimer units, said dimer units comprising said at least one first planarized bithiophene repeat unit (I) and a second repeat unit, said second repeat unit comprising at least one thiophene ring structure.

23. The composition according to claim 1, wherein said at least one copolymer comprises repeating dimer units, said dimer units comprising said at least one first bithiophene repeat unit (I) and a second repeat unit, said second repeat unit being represented by at least one of the following:

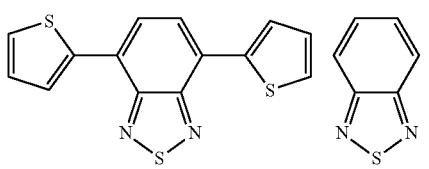
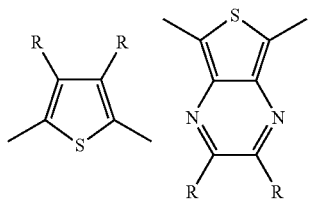
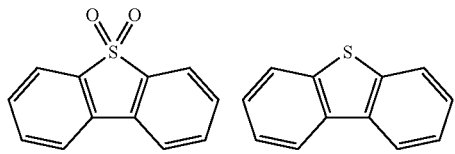
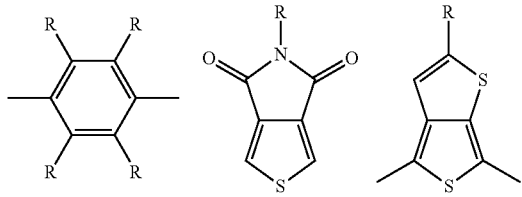
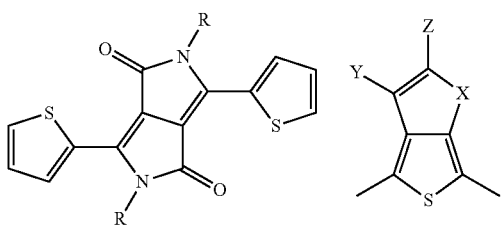
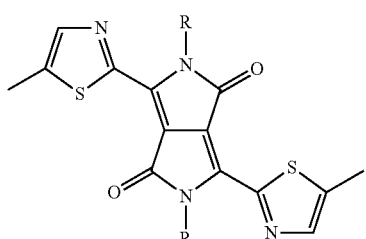
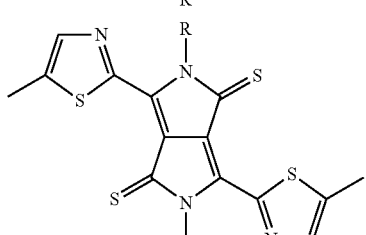
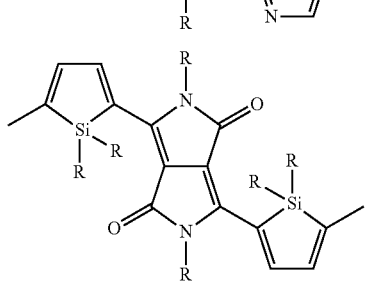

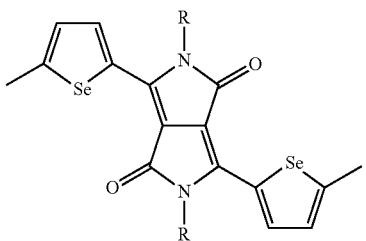

wherein R are solubilizing groups, X is sulfur, oxygen, or nitrogen, or selenium, Y is a halogen or hydrogen, and Z is alkyl or branched alkyl.

24. The composition according to claim 1, wherein said at least one copolymer comprises repeating dimer units, said dimer unit comprising said at least one first bithiophene repeat unit (I) and a second repeat unit, said second repeat unit being represented by at least one of the following:

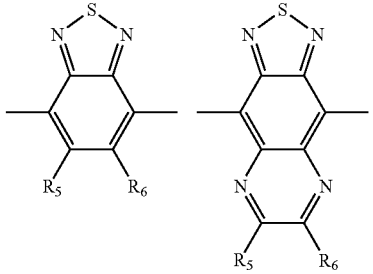
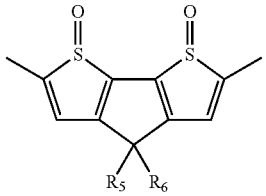
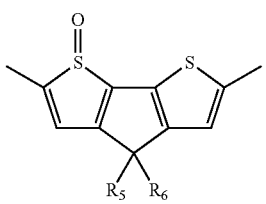
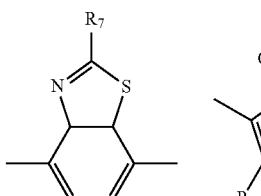
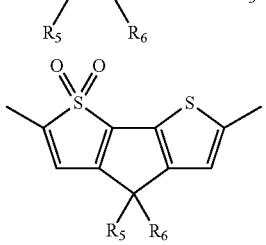

-continued

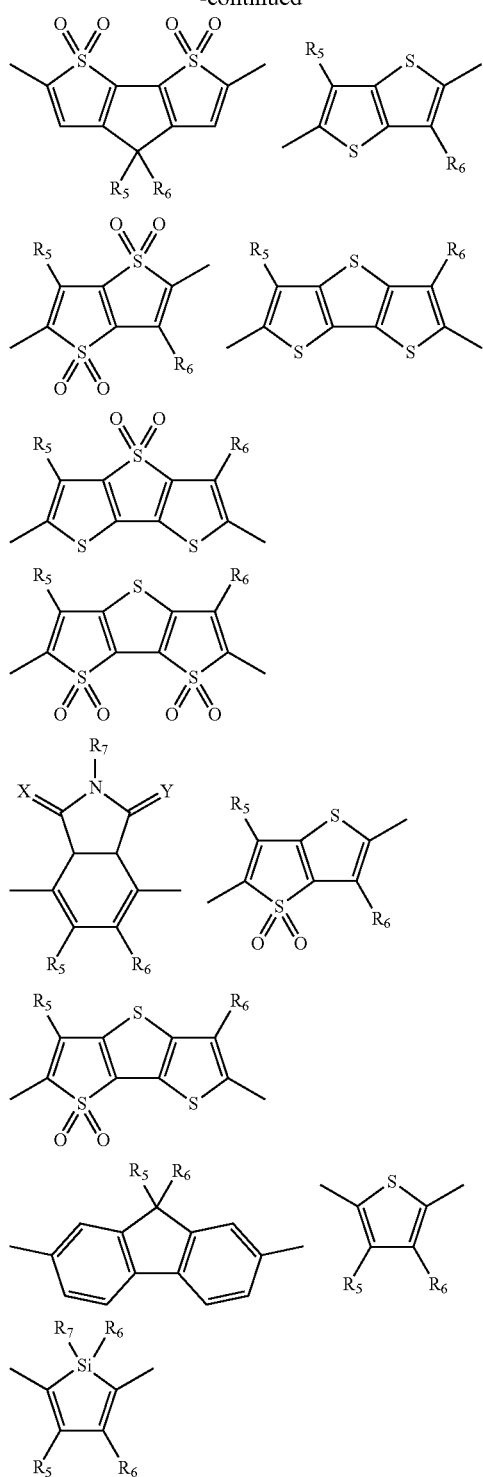

wherein $R_5$, $R_6$, $R_7$, and $R_8$ are solubilizing groups and X and Y are independently $CH_2$, O, or S.

25. The composition according to claim 1, wherein said at least one copolymer comprises repeating dimer units, said dimer units comprising at least one first bithiophene repeat unit (I) and a second repeat unit, said second repeat unit being represented by at least one of the following:

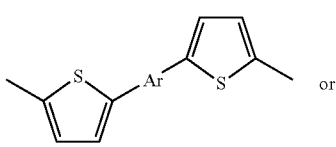

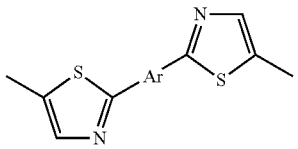

wherein Ar is represented by:

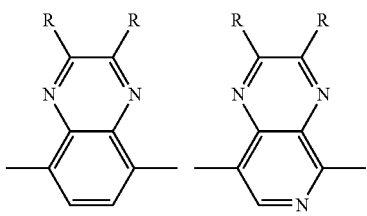

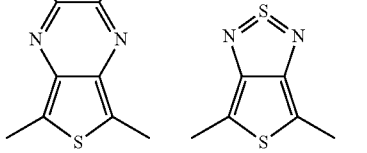

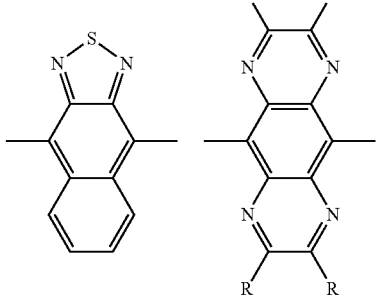

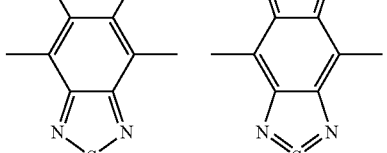

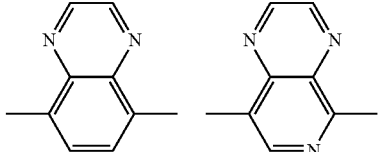

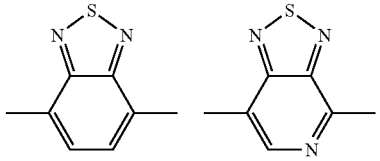

-continued

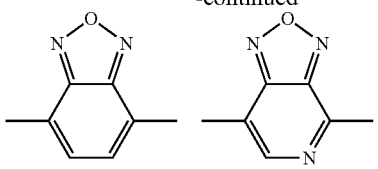

and further wherein R are solubilizing groups.

26. The composition according to claim 1, wherein the copolymer has a degree of polymerization of 5 to 100,000.

27. The composition according to claim 1, wherein the copolymer has a degree of polymerization of 10 to 10,000.

28. The composition according to claim 1, wherein the copolymer comprises at least two different donors, or the copolymer comprises at least two different acceptors.

29. The composition according to claim 1, wherein the copolymer is prepared by an alternating copolymerization of at least two monomers.

30. A composition comprising at least one donor acceptor copolymer, said at least one copolymer comprising at least one first bithiophene repeat unit represented by:

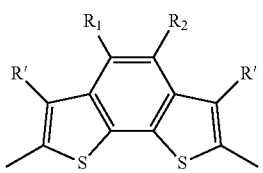

wherein $R_1$ and $R_2$ and R' are solubilizing groups or hydrogen, further wherein $R_1$ and $R_2$ form an optionally substituted ring, and further wherein said at least one copolymer does not comprise poly[2,6-(4,4-dioctyl-4H-cyclopenta[2,1-b:3,4-b']dithiophene)-alt-2,7-(4,5-dioctylbenzo[2,1-b:3,4-b']dithiophene)], poly[2,6-(4,4-dioctyl-4H-cyclopenta[2,1-b:3,4-b']dithiophene)-alt-2,9-(5,6-dioctylnaphtho[2,1-b:3,4-b']dithiophene)], or poly[2,6-(4,4-dioctyl-4H-cyclopenta[2,1-b:3,4-b']dithiophene)-ah-6,9-(2,3-bis((S)-2,6-dimethylheptyl)ditheno[3,2-f:2',3'-h]quinoxaline].

31. A composition comprising at least one donor acceptor copolymer, said at least one copolymer comprising at least one repeat unit represented by (II):

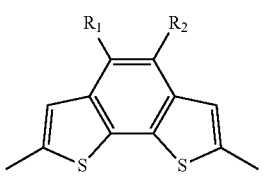

(II)

wherein $R_1$ and $R_2$ form an optionally substituted ring.

32. The composition of claim 31, wherein $R_1$ and $R_2$ form an optionally substituted benzene ring.

33. The composition of claim 31, wherein $R_1$ and $R_2$ form an optionally substituted heterocyclic ring.

34. The composition of claim 31, wherein the donor acceptor copolymer comprises at least one first donor, at least one first acceptor, and at least one additional second donor or second acceptor different from the first.

35. The composition of claim 31, wherein the donor acceptor copolymer comprises at least one first donor, at least one first acceptor, and at least one second acceptor different from the first.

36. The composition according to claim 31, wherein at least one bithiophene repeat unit is represented by (III):

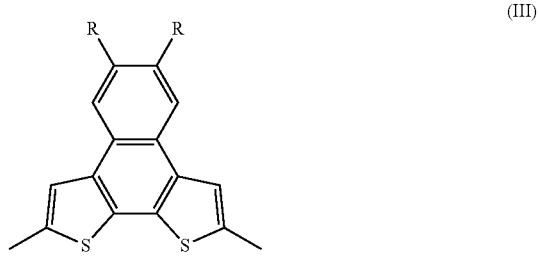

(III)

and further wherein R are solubilizing groups or hydrogen.

37. The composition according to claim 31, wherein at least one bithiophene repeat unit is represented by:

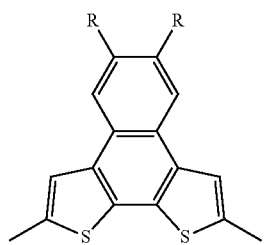

and further wherein R are solubilizing groups.

38. The composition according to claim 31, wherein the structure (II) provides a donor to the donor acceptor copolymer.

39. The composition according to claim 31, wherein said at least one copolymer is an alternating copolymer.

40. The composition according to claim 31, wherein the acceptor comprises

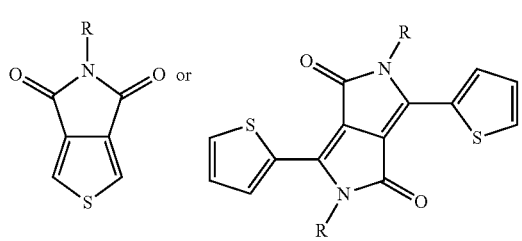

wherein R comprises a solubilizing group.

41. A composition comprising at least one donor acceptor copolymer, said at least one copolymer comprising as donor at least one first bithiophene repeat unit represented by (I):

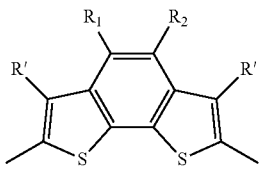
(I)

wherein $R_1$, $R_2$ and R' are solubilizing groups or hydrogen, wherein $R_1$ and $R_2$ form an optionally substituted ring, wherein the copolymer further comprises at least one repeat moiety represented by:

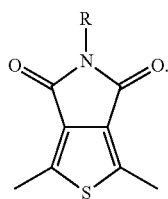

42. A composition comprising a mixture comprising: (i) at least one p-type material, (ii) at least one n-type material, wherein the at least one p-type material comprises at least one donor acceptor copolymer, said at least one copolymer comprising as donor at least one first bithiophene repeat unit represented by (I):

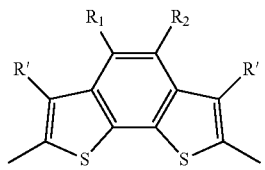
(I)

wherein $R_1$, $R_2$, and R' are solubilizing groups or hydrogen and wherein $R_1$ and $R_2$ form an optionally substituted ring.

43. The composition of claim 42, wherein the R' groups are hydrogen and the $R_1$ and $R_2$ groups are solubilizing groups which optionally can form a ring.

44. The composition of claim 42, wherein the n-type material is a fullerene derivative.

45. The composition according to claim 42, wherein the at least one n-type material comprises a $C_{60}$-indene adduct.

46. The composition according to claim 42, wherein the at least one n-type material comprises PCBM.

47. The composition according to claim 42, the composition further comprising a solvent.

48. An ink composition comprising the composition of claim 1.

49. An electronic device comprising the composition of claim 1.

50. A photovoltaic cell comprising an active layer comprising the composition of claim 1.

51. The composition according to claim 46, wherein the PCBM is C60-PCBM or C70-PCBM.

52. The composition of claim 1, wherein the copolymer comprises at least one repeat unit that is not a planarized bithiophene repeat unit.

* * * * *